US012290332B2

(12) United States Patent
Rackers et al.

(10) Patent No.: US 12,290,332 B2
(45) Date of Patent: May 6, 2025

(54) AIR GAP DETECTORS IN HEATING SYSTEM FOR DRAPED BASIN

(71) Applicant: WEG Surgical Solutions, LLC, Cary, NC (US)

(72) Inventors: Kevin Joseph Rackers, Summerfield, NC (US); Thomas J. Wanbaugh, Cary, NC (US); Paul Grozier, Libertyville, IL (US)

(73) Assignee: WEG Surgical Solutions, LLC, Greensboro, NC (US)

( * ) Notice: Subject to any disclaimer, the term of this patent is extended or adjusted under 35 U.S.C. 154(b) by 1059 days.

(21) Appl. No.: 17/229,813

(22) Filed: Apr. 13, 2021

(65) Prior Publication Data

US 2021/0236223 A1    Aug. 5, 2021

Related U.S. Application Data

(63) Continuation-in-part of application No. 16/240,387, filed on Jan. 4, 2019, now Pat. No. 10,973,601.

(Continued)

(51) Int. Cl.
*A61B 46/00*     (2016.01)
*A61F 7/00*      (2006.01)

(52) U.S. Cl.
CPC ............ *A61B 46/00* (2016.02); *A61F 7/0053* (2013.01); *A61F 7/007* (2013.01)

(58) Field of Classification Search
CPC . A61B 46/00; A61B 46/10; A61F 2007/0093; A61F 2007/0096; A61F 7/0053; A61F 7/007; A61F 7/0085

(Continued)

(56) References Cited

U.S. PATENT DOCUMENTS 1,791,254 A    2/1931  Von
1,797,963 A    3/1931  Neller
(Continued)

FOREIGN PATENT DOCUMENTS

WO    WO-03039387 A1 *  5/2003  ............. A61B 46/10
WO    2005096916 A1    10/2005

OTHER PUBLICATIONS

Han, Inho, Patent Cooperation Treaty—International Search Report for International Application No. PCT/US2019/061842 (same patent application family as the present application), Mar. 17, 2020, 3 pages, International Application Division of Korean Intellectual Property Office, Daejeon, South Korea.

(Continued)

*Primary Examiner* — Steven W Crabb
*Assistant Examiner* — Ket D Dang
(74) *Attorney, Agent, or Firm* — Kevin E Flynn; FLYNN IP LAW

(57) ABSTRACT

A heating system for providing heat to a draped basin containing liquid above the drape. In addition to having at least one temperature sensor that controls a flow of electricity to the heating element, the system has at least one air gap detector in thermal contact with the heating element. Each air gap detector responding to a temperature above a high setpoint temperature for that air gap detector by interrupting the flow of electricity until detecting that the temperature has fallen below a reset setpoint temperature for that air gap detector so that an air gap in proximity to the one of the air gap detectors is prevented from causing a severe temperature excursion in a portion of the draped basin. Thus, the drape is protected from a local temperature excursion.

23 Claims, 36 Drawing Sheets

Related U.S. Application Data

(60) Provisional application No. 62/768,721, filed on Nov. 16, 2018.

(58) Field of Classification Search
USPC .......................................................... 219/201
See application file for complete search history.

(56) References Cited

U.S. PATENT DOCUMENTS

| | | |
|---|---|---|
| 1,811,896 A | 6/1931 | Ross |
| 2,546,104 A | 3/1951 | James |
| 2,682,602 A | 6/1954 | Huck |
| 2,892,066 A | 6/1959 | Springer |
| 2,898,439 A | 8/1959 | Clarence |
| 2,994,761 A | 8/1961 | Deryl |
| 3,031,565 A | 4/1962 | Appleton |
| 3,134,007 A | 5/1964 | Niblo |
| 3,299,883 A | 1/1967 | Rubens |
| 3,374,936 A | 3/1968 | Colato |
| 3,698,594 A | 10/1972 | Boehlert |
| 3,751,629 A | 8/1973 | Eisler |
| 3,767,898 A | 10/1973 | Wells et al. |
| 3,892,945 A | 7/1975 | Lerner |
| 3,974,358 A | 8/1976 | Goltsos |
| 4,064,886 A | 12/1977 | Heckele |
| 4,164,644 A | 8/1979 | Remsnyder et al. |
| 4,288,882 A | 9/1981 | Takeuchi |
| 4,419,568 A | 12/1983 | van Overloop |
| 4,700,050 A | 10/1987 | Hennuy et al. |
| D298,452 S | 11/1988 | Carter |
| 4,934,152 A | 6/1990 | Templeton |
| 4,967,057 A | 10/1990 | Bayless et al. |
| 4,967,061 A | 10/1990 | Weber, Jr. et al. |
| 5,129,033 A | 7/1992 | Ferrara et al. |
| 5,174,306 A | 12/1992 | Marshall |
| 5,207,213 A | 5/1993 | Auhll et al. |
| 5,271,085 A | 12/1993 | Carballo |
| 5,294,779 A | 3/1994 | Miquelot |
| 5,309,895 A | 5/1994 | Yabe |
| 5,331,820 A | 7/1994 | Faries, Jr. et al. |
| 5,333,326 A | 8/1994 | Faries, Jr. |
| 5,381,729 A * | 1/1995 | Hennessy ................ H05B 3/82 |
| | | 126/369 |
| 5,392,766 A | 2/1995 | Masterson et al. |
| 5,400,616 A | 3/1995 | Faries, Jr. et al. |
| 5,402,644 A | 4/1995 | Faries, Jr. |
| 5,415,180 A | 5/1995 | Horan |
| 5,435,322 A | 7/1995 | Marshall |
| 5,451,747 A | 9/1995 | Sullivan et al. |
| 5,457,962 A | 10/1995 | Faries, Jr. |
| 5,464,008 A | 11/1995 | Kim |
| 5,487,376 A | 1/1996 | Yabe et al. |
| 5,511,568 A | 4/1996 | Bowman et al. |
| 5,518,146 A | 5/1996 | Mattei |
| 5,522,095 A | 6/1996 | Faries, Jr. |
| 5,524,643 A | 6/1996 | Faries, Jr. |
| 5,549,543 A | 8/1996 | Kim |
| 5,551,240 A | 9/1996 | Faries, Jr. et al. |
| 5,569,163 A | 10/1996 | Francis et al. |
| 5,615,423 A | 4/1997 | Faries, Jr. et al. |
| 5,647,840 A | 7/1997 | DAmelio et al. |
| 5,651,757 A | 7/1997 | Meckstroth |
| 5,653,938 A | 8/1997 | Faries, Jr. et al. |
| 5,718,124 A | 2/1998 | Senecal |
| 5,729,653 A | 3/1998 | Magliochetti et al. |
| 5,785,644 A | 7/1998 | Grabover et al. |
| 5,816,252 A | 10/1998 | Faries, Jr. |
| 5,857,467 A | 1/1999 | Faries, Jr. |
| 5,862,672 A | 1/1999 | Faries, Jr. et al. |
| 5,863,287 A | 1/1999 | Segawa |
| 5,879,621 A | 3/1999 | Faries, Jr. et al. |
| 5,910,106 A | 6/1999 | Morgan et al. |
| 6,003,328 A | 12/1999 | Faries, Jr. |
| 6,035,855 A | 3/2000 | Faries, Jr. |
| 6,087,636 A | 7/2000 | Faries, Jr. et al. |
| 6,091,058 A | 7/2000 | Faries, Jr. et al. |
| 6,140,615 A * | 10/2000 | Matsumoto ............. H05B 3/80 |
| | | 392/444 |
| 6,167,296 A | 12/2000 | Shahidi |
| 6,234,635 B1 | 5/2001 | Seitzinger et al. |
| 6,255,627 B1 | 7/2001 | Faries, Jr. et al. |
| 6,259,067 B1 | 7/2001 | Faries, Jr. et al. |
| 6,268,591 B1 | 7/2001 | Thevenin |
| 6,274,847 B1 | 8/2001 | Hlava et al. |
| 6,294,762 B1 | 9/2001 | Faries, Jr. et al. |
| 6,342,691 B1 | 1/2002 | Johnsgard et al. |
| 6,354,992 B1 | 3/2002 | Kato |
| 6,371,121 B1 | 4/2002 | Faries, Jr. et al. |
| 6,384,380 B1 | 5/2002 | Faries, Jr. et al. |
| 6,392,206 B1 | 5/2002 | Von Arx et al. |
| 6,401,602 B1 | 6/2002 | Lin |
| 6,417,498 B1 | 7/2002 | Shields et al. |
| 6,433,317 B1 | 8/2002 | Arx et al. |
| 6,457,601 B1 | 10/2002 | Chappell |
| 6,547,724 B1 | 4/2003 | Soble et al. |
| 6,591,130 B2 | 7/2003 | Shahidi |
| 6,593,552 B1 | 7/2003 | Li |
| 6,660,974 B2 | 12/2003 | Faries, Jr. et al. |
| 6,711,989 B1 | 3/2004 | Sarnoff |
| 6,712,479 B1 | 3/2004 | Seitzinger et al. |
| 6,768,085 B2 | 7/2004 | Faries, Jr. et al. |
| 6,810,881 B2 | 11/2004 | Faries, Jr. |
| 6,860,271 B2 | 3/2005 | Faries, Jr. et al. |
| 6,864,462 B2 | 3/2005 | Sanoner et al. |
| 6,884,970 B2 | 4/2005 | Lehman |
| 6,910,485 B2 | 6/2005 | Faries, Jr. et al. |
| 6,918,395 B2 | 7/2005 | Faries, Jr. et al. |
| 6,927,365 B2 | 8/2005 | Li |
| 7,128,275 B2 | 10/2006 | Kammer et al. |
| 7,176,030 B2 | 2/2007 | Faries, Jr. et al. |
| D546,943 S | 7/2007 | Kammer et al. |
| D546,944 S | 7/2007 | Kammer et al. |
| D547,444 S | 7/2007 | Kammer et al. |
| 7,279,660 B2 | 10/2007 | Long et al. |
| 7,311,660 B2 | 12/2007 | Gomez |
| 7,347,210 B2 * | 3/2008 | Faries, Jr. .............. A61B 46/10 |
| | | 128/849 |
| D568,989 S | 5/2008 | Kammer et al. |
| D569,970 S | 5/2008 | Kammer et al. |
| 7,417,205 B2 | 8/2008 | Faries, Jr. |
| 7,418,966 B2 | 9/2008 | Faries, Jr. |
| 7,441,714 B2 | 10/2008 | Kammer |
| 7,459,657 B2 | 12/2008 | Kammer |
| 7,560,667 B2 | 7/2009 | Kammer |
| 7,589,299 B2 | 9/2009 | Fisher et al. |
| 7,671,302 B1 | 3/2010 | Faries, Jr. et al. |
| 7,728,262 B1 | 6/2010 | Faries, Jr. et al. |
| 7,745,759 B2 | 6/2010 | Long et al. |
| 7,854,387 B2 | 12/2010 | Kammer et al. |
| 7,903,957 B2 | 3/2011 | Kammer et al. |
| 7,959,860 B2 | 6/2011 | Faries, Jr. |
| 8,138,454 B2 | 3/2012 | Kammer et al. |
| 8,148,666 B2 | 4/2012 | Faries, Jr. |
| 8,308,074 B2 | 11/2012 | Kammer et al. |
| 8,309,891 B2 * | 11/2012 | Kammer ............. A61M 3/0245 |
| | | 219/432 |
| 8,313,462 B2 * | 11/2012 | Faries, Jr. ........... A61M 5/1483 |
| | | 604/114 |
| 8,523,082 B2 | 9/2013 | Kammer et al. |
| 8,789,534 B2 | 7/2014 | Faries, Jr. |
| 9,114,218 B2 | 8/2015 | Kammer et al. |
| 9,326,667 B2 | 5/2016 | Kammer et al. |
| 10,224,630 B2 | 3/2019 | Iellci |
| 10,973,601 B2 | 4/2021 | Rackers |
| 2001/0045188 A1 | 11/2001 | Tsengas |
| 2002/0043260 A1 | 4/2002 | Layer et al. |
| 2002/0188259 A1 | 12/2002 | Hickle et al. |
| 2003/0000939 A1 | 1/2003 | Durward, Jr. et al. |
| 2003/0230588 A1 | 12/2003 | Zepter |
| 2004/0065314 A1 | 4/2004 | Layer et al. |
| 2005/0234301 A1 | 10/2005 | Gomez |
| 2005/0242086 A1 | 11/2005 | Imura |
| 2005/0267425 A1 | 12/2005 | Castora et al. |
| 2006/0011608 A1 | 1/2006 | Lehman |

(56) References Cited

U.S. PATENT DOCUMENTS

| | | |
|---|---|---|
| 2006/0065276 A1 | 3/2006 | Kammer et al. |
| 2006/0086361 A1 | 4/2006 | Kammer et al. |
| 2008/0216668 A1 | 9/2008 | Fraij et al. |
| 2011/0114629 A1 | 5/2011 | Kammer et al. |
| 2011/0224630 A1 | 9/2011 | Simmons |
| 2012/0020182 A1 | 1/2012 | Gammons |
| 2012/0244327 A1 | 9/2012 | Hernandez |
| 2013/0183465 A1 | 7/2013 | Liang |
| 2017/0274157 A1 | 9/2017 | Hendrix et al. |
| 2018/0098903 A1* | 4/2018 | Vergara ................. A61F 7/0085 |
| 2019/0090972 A1 | 3/2019 | Hendrix |

OTHER PUBLICATIONS

Han, Inho, Patent Cooperation Treaty—Written Opinion of the International Searching Authority for International Application No. PCT/US2019/061842 (same patent application family as the present application), Mar. 17, 2020, 5 pages, International Application Division of Korean Intellectual Property Office, Daejeon, South Korea.

* cited by examiner

200

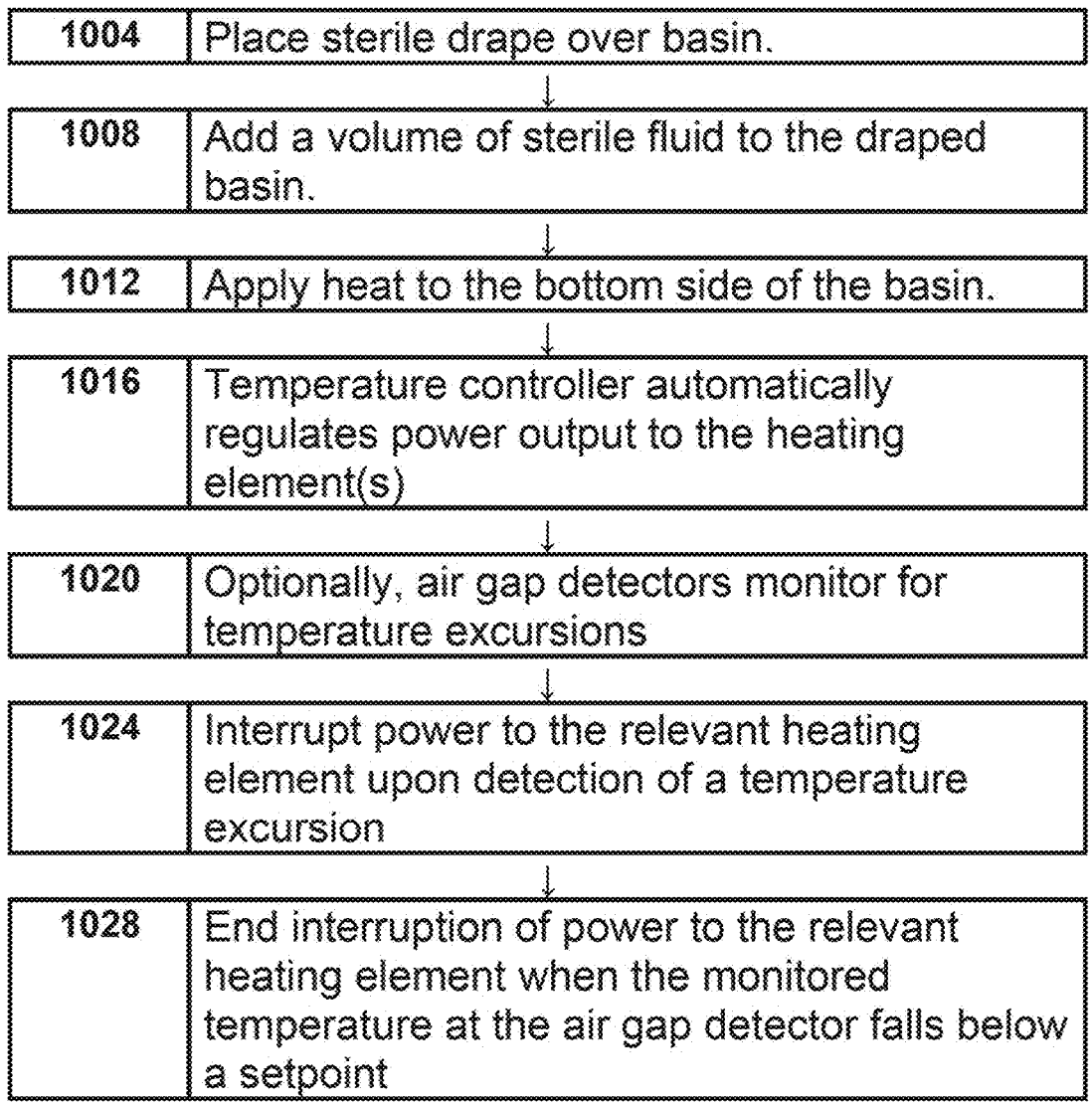

450

400

470

600

700

610

610

610

610

610

610

610

610

700

710

710

710

710

710

710

710

AIR GAP DETECTORS IN HEATING SYSTEM FOR DRAPED BASIN

This application claims priority to earlier filed and co-pending application Ser. No. 16/240,387 for Sterile Solution Warming System with Self-Locating Sterile Drape, through the '387 application, this application claims the benefit of earlier filed U.S. Provisional Application No. 62/768,721 filed on Nov. 16, 2018 for Sterile Solution Warming System with Self-Locating Sterile Drape. Both of these applications are incorporated herein by reference. Modifications made to the '387 application during prosecution that were deemed as not adding new matter have be replicated herein. As this application adds material not found in the '387 application, this is technically a Continuation-in-Part application although some or all of the issued claims may be entitled to the original priority dates.

BACKGROUND

Field of the Disclosure

This disclosure relates generally to fluid warming for sterile fluids such as sterile saline used in surgical procedures. The fluid warming process uses a sterile drape to separate the sterile fluid from the equipment used to provide heat and to hold the drape and sterile fluid.

Related Art

The concept for heating sterile liquid is not new. The process was certainly known as far back as 1993 when the application leading to U.S. Pat. No. 5,333,326 was filed for a Method and Apparatus for Producing Surgical Slush and Heated Sterile Liquid. The '326 taught a piece of equipment with a heating unit having a warming basin which provided a recessed cavity with an open top. A sterile drape covered the heating basin so that sterile fluid placed in the drape could be maintained as sterile as long as the drape was not ruptured during use. Heat was transferred from a heating element below the basin, through the basin, and ultimately through the drape adjacent to the basin to the sterile liquid.

Problems with Prior Art Designs

Basin Hot Spots from Air Gaps.

Turning to FIG. 1, a basin 102 is represented in cross section above a set of one or more heating element 104 and a temperature sensor 108. The heating element 104 may be an annular heating element (as is the case here) or a series of several separate heating elements that are provided with power to add heat when the temperature sensor 108 indicates a temperature below the target temperature (often the temperature corresponding to a slight increase above the core temperature of a patient). Those of skill in the art will recognize that a temperature controller (not shown) may be an intermediary between the temperature sensor 108 and the heating element 104. While the heating element 104 and temperature sensor 108 are shown slightly offset from the basin 102 in order to highlight the differences between components, those of skill in the art will appreciate that the heating element 104 and temperature sensor 108 would be in thermal connection with the metal basin 102.

FIG. 2 is an enlarged representation of a portion of FIG. 1. For purposes of this introduction, no drape is present. The basin 102 is shown with walls having a thickness. The temperature of the heating element 104 will be elevated until the temperature 166 of the temperature sensor 108 reaches a target temperature. Those of skill in the art will appreciate that while the temperature 154 of the basin just above the heating element 104 may be close to the temperature 150 of the heating element 104, there will be a drop-off in temperature moving along the basin 102. So there may be zones on either side of the heating element 104 at slightly reduced temperature 158 and then further away from the heating element 104 the temperature may be still further reduced to temperature 162. Sufficiently far from the heating element 104, the temperature 170 of the basin 102 will be close to the temperature 174 of the ambient air in the room.

FIG. 3 shows FIG. 2 with liquid 120 added. Assuming the same amount of power delivered to heating element 104, the temperature 172 of heating element 104 would be less as the liquid 120 does a better job conducting heat than does air. Thus, the gradient of the bands of temperature drops off faster than shown in FIG. 2. The temperature 176 would be less than temperature 172 and would drop off through temperatures 178 and 182. Eventually the temperature of liquid 120 away from the heating element 104 may be temperature 186 which would be close to the temperature 190 sensed at the temperature sensor 108.

FIG. 4 shows FIG. 3 with a flexible drape 124 lining the basin 102 and containing liquid 120. The heating element 104 would be sized and powered to quickly bring the typical volume of liquid 120 perhaps 1.5 liters or more from ambient temperature around 70° F. to a target temperature 190 as measured at the temperature sensor 108 in the range of 104° F. One of skill in the art will appreciate that the temperature of the volume of liquid will not be uniform. The temperature may vary in the range of plus or minus 2 degrees Fahrenheit in the fluid away from the boundary condition of the heated basin.

FIG. 5 shows the basin 102 with a flexible drape 124 and the liquid 120. Notice that in FIG. 5, there is a sizable gap between the flexible drape 124 and the vertical wall of the basin 102. An air gap 128 remains even after the addition of the liquid 120. FIG. 6 shows a close up of the air gap area of FIG. 5.

The difference in heat conduction between the air gap 128 and the fluid filled flexible drape 124 is significant. This causes temperature gradients throughout the system. Within the heating element 104 there will be a temperature gradient from a higher temperature 130 down through temperatures 132 and 134 to cooler temperature 138 as that side of the heating element 104 gives off heat more rapidly to the flexible drape 124 filled with liquid 120 than the other side of the heating element 104. There will be a temperature gradient across the flexible drape 124. The temperature of the flexible drape 124 will be highest near the heating element 104 and will drop further away from the heating element 104. So the temperatures may range from a high of temperature 140 through temperatures 142, 144, and 148. Likewise the temperature of the liquid 120 above the flexible drape 124 will have a gradient from a high of temperature 150 down through temperatures 152, 156 and 158.

In the air gap 128, the basin 102 will reflect the higher temperature end of heating element 104 but will have some drop-off in temperature from a high of temperature 160 downward through temperatures 161, 162, 163, and 164.

Just as putting a pot of water half on and half off an electric burner will cause the portions of the electric burner not under the pot to glow red, the portion of the heating element 104 under the air gap 128 may get significantly hotter than the portion of the heating element 104 under the flexible drape 124 and liquid 120. As the control system is providing a lot of power to rapidly take the liquid 120 from 70° F. to over 100° F., the portion of the heating element 104 under the air gap may approach 400° F. as the temperature sensor 108 is indicating that the liquid 120 needs substantially more heat.

While it is a severe problem if the air gap extends all the way out to the temperature sensor 108 there is a problem even with a smaller air gap that does not extend all the way to the temperature sensor. The controller for the heating system applies power to the heater in response to the temperature measured at the temperature sensor 108. This power is applied to the heating element 104. If there the heat from the heater is not flowing into the liquid 120 as intended, there can be a local hot spot on the basin 102 above the heating element 104. This local hot spot could pose a risk to the flexible drape 124 if the temperature of the basin 102 above the heating element 104 exceeds the softening temperature of the flexible drape 124 and the flexible drape 124 is suddenly put into contact with the hot portion of the basin 102 to allow the flexible drape 124 to be heated above the softening temperature for the flexible drape 124, thus increasing the risk of a puncture of the flexible drape 124.

The flexible drape 124 may be made of polyurethane with a softening temperature of 300 degrees to 330° F. Placement of an instrument into the liquid 120 in the flexible drape 124 may move a portion of the flexible drape 124 to make contact with the basin 102 adjacent to the air gap 128 which would subject that portion of the flexible drape 124 to a temperature excursion as that portion of the flexible drape 124 contacts the hot metal basin 102. A temperature excursion that takes any portion of the flexible drape 124 above the softening point for the flexible drape 124 produces a risk that the flexible drape may develop a leak as the instrument pushes against softened drape material. While liquid 120 that leaks out of the flexible drape 124 will be contained in the basin 102, the breach in the flexible drape 124 will mean the non-sterile surface of the basin 102 will be exposed to the liquid 120 and thus pose risks for any patient exposed to non-sterile liquid erroneously believed to be sterile and suitable for use in a surgical procedure or to rinsed surgical instruments to be reused within that surgical procedure.

This risk is elevated given that many instruments used in surgical procedures are metallic and have sharp surfaces.

Note that while the air gap 128 was shown close to one vertical wall of the basin 102, the air gap 128 could be away from the perimeter of the basin 102 as an excess of flexible drape 124 may initially exist in the interior portion of the basin 102. If this excess is not removed by stretching out the flexible drape 124 an elongated wrinkle in the flexible drape 124 may be held in place after the addition of liquid 120. To the extent that the elongated wrinkle passes over or adjacent to a heating element 104, there is a risk that the temperature of the basin 102 between the heating element 104 and the air gap 128 in the wrinkle may go much higher than the temperature of the basin 102 between the heating element 104 and the portions of the flexible drape 124 without any air gap 128. This could lead to the same risk of softening a portion of the flexible drape 124 by the unusually hot portion of the basin 102. Those of skill in the art will appreciate that the risk of an unusually hot portion of the basin 102 will increase when the air gap 128 is larger than a small air gap caused by a wrinkle.

Efforts by the surgical staff to maintain placement of the flexible drape 124 within the basin 102 without air gaps or other wrinkles of the flexible drape 124 have led some staff members to hold the flexible drape 124 flat while pouring a first container of liquid 120 into the drape. While this extra effort by the surgical staff is commendable, the problems with the prior art solution that encourage staff to make extra efforts are not desirable. The surgical staff may also place a heavy object on the flexible drape 124 to hold the surgical drape 124 in place, however, a heavy object like a metal pitcher of liquid can give artificially low temperature readings at the temperature sensor 108 if the pitcher is placed over the temperature sensor 108. An incorrect low reading by the temperature sensor 108 could cause additional problems if there are air gaps because the controller will drive more power to the heaters and thus more heat into the system.

For context, it is useful to note that while many hospitals may use warmed containers of sterile saline at approximately 85° F. to reduce the time to heat the saline to 104° F., hospitals will want the heater system to be able to quickly warm a bottle of saline at operating room ambient temperature (possibly 67° F.). Thus, the heater systems are capable of providing a significant amount of energy to heat cool liquids quickly to 104° F.

Contaminated Drapes From Initial Misalignment of Flexible Drape.

A second failure of a flexible drape is the failure to center the flexible drape over the recessed basin 102. When a flexible drape is delivered for use, the flexible drape is initially sterile on both sides of the flexible drape. As the flexible drape is unfolded, the drape is positioned to cover a top surface of the heating device, including the recessed basin 102. The flexible drape 124 also extends downward along the sides of the heating device but only a portion of the way from the top surfaces of the heating device towards the floor.

One of the purposes of the flexible drape 124 is to cover the non-sterile surfaces of the heating device around the basin. To the extent that the flexible drape 124 is not centered upon the heating device, then non-sterile portions of the side of the heating device may be uncovered and pose a risk of contamination to the medical staff moving in proximity to the heating device. In an extreme case, the flexible drape 124 may touch the floor which is non-sterile but this would be an extreme case.

To the extent that the flexible drape 124 is initially unfolded so that the intended upper side of the flexible drape 124 is placed upside down so that the intended upper side of the flexible drape 124 touches the non-sterile heating device, then the flexible drape 124 cannot be safely turned over and must be used outside of the intended orientation or discarded. If the topside of the flexible drape 124 touches a non-sterile surface the flexible drape 124 should be disposed of and a new flexible drape 124 applied. The flexible drape 124 application technique is therefore critical, and the accurate initial placement of the flexible drape to the basin 102 is an important part of the procedure.

Punctures of Flexible Drape from Rough Treatment.

Given the focus of the surgical team on the patient, it is possible that instruments may be placed in the basin 102 covered by the flexible drape without total focus on the placement from time to time. Dropping a surgical instrument even a short distance into the basin 102 covered with flexible drape 124 may lead to a puncture or other damage to the flexible drape 124, even if there is not an air gap 128 causing a hot spot on the basin 102. One solution is to control the temperature to ensure the flexible drape 124 does not approach the softening temperature; another solution is to have a second layer of flexible drape for the portion of the flexible drape that is within the basin. While this solution reduces the risk of a breach of the flexible drape, this solution heightens the need to align the flexible drape with some precision relative to the inner perimeter of the basin 102.

Vocabulary.

Unless explicit to the contrary, the word "or" should be interpreted as an inclusive or rather than an exclusive or. Thus, the default meaning of or should be the same as the more awkward and/or.

Unless explicit to the contrary, the word "set" should be interpreted as a group of one or more items.

Frequently, when describing an industrial process, it is useful to note that a given parameter is substantially met. Examples may be substantially parallel, substantially perpendicular, substantially uniform, and substantially flat. In this context, substantially X means that for purposes of this industrial process it is X. So something that may not be absolutely parallel but is for all practical purposes parallel is substantially parallel. Likewise, mixed air that has substantially uniform temperature would have temperature deviations that were inconsequential for that industrial process.

As recognized in C. E. Equipment Co. v. United States, 13 U.S.P.Q.2d 1363, 1368 (Cl. Ct. 1989), the word "substantially" in patent claims gives rise to some definitional leeway-thus the word "substantially" may prevent avoidance of infringement by minor changes that do not affect the results sought to be accomplished.

SUMMARY OF THE DISCLOSURE

Aspects of the teachings contained within this disclosure are addressed in the claims submitted with this application upon filing. Rather than adding redundant restatements of the contents of all of the claims, these claims should be considered incorporated by reference into this summary.

Some aspects of the teachings of the present disclosure may be expressed as a drape for covering an interior of a basin and at least a top of a fluid heating device. The fluid heating device basin having an upper side defining a cavity for receipt of a fluid to be heated. The upper side of the basin having a basin bottom and a set of basin sidewalls running from the basin bottom to the top of the fluid heating device. The drape having a basin layer. The basin layer sized sufficiently to cover at least the basin bottom. The drape also having a device layer sized sufficiently to cover the top of the fluid heating device and extend downward around a perimeter of the fluid heating device while a portion of the device layer is in proximity to the basin. The drape also having a set of at least one positioning component trapped between the basin layer and the device layer by a set of bonds between the basin layer and the device layer. The set of at least one positioning component sized and located to fit within a perimeter defined by the set of basin sidewalls to substantially center the basin layer on the basin bottom. The set of bonds between the basin layer and the device layer arranged to allow egress of air from between the basin layer and device layer so a volume of air between the basin layer and the device layer is reduced when liquid is placed onto the drape after the drape is positioned to cover the basin and the fluid heating device.

The drape may be created with the basin layer having a lower coefficient of film-to-film kinetic friction than does the device layer so that the basin layer may slip into position within the basin and the device layer tends to limit unintended lateral movement of the drape relative to the fluid heating device.

Some aspects of the teachings of the present disclosure may be expressed as a single layer drape with a set of at least one positioning component sized and located to fit within a perimeter defined by the set of basin sidewalls to substantially center the basin portion on the basin bottom.

Some aspects of the teachings of the present disclosure may be expressed as a method of covering a fluid heating device with a cavity defined by a basin. The method including placing a drape over top of a fluid heating device while inserting a set of at least one positioning component into an interior of the basin onto a bottom of the basin. The set of at least one positioning component connected to the drape and sized relative to a perimeter of the bottom of the basin to substantially limit a range of possible locations for the drape when the set of at least one positioning component is placed within the perimeter of the basin. The method further including adding a volume of a fluid to the basin so that the fluid rests on the drape without making contact with the basin. As the drape is adapted to allow air located below an upper surface of the drape and above the bottom of the basin to move during an addition of a liquid to reduce an amount of air located below the upper surface of the drape and above the bottom of the basin, adding the volume of fluid causes movement of air. The method further including adding heat to the bottom of the basin to allow heat to pass through the drape and into the liquid. The method further including monitoring at least one temperature of the basin and controlling the heat added to the basin based upon the at least one temperature of the basin to maintain the liquid within a desired range of a selected target temperature.

Some aspects of the teachings of the present disclosure may be expressed as a drape for covering an interior of a basin and at least a top of a fluid heating device. The basin having an upper side defining a cavity for receipt of a fluid to be heated. The upper side of the basin having a basin bottom and a set of basin sidewalls running from the basin bottom to the top of the fluid heating device. The drape having a basin layer sized sufficiently to cover at least the basin bottom. The basin layer having a coefficient of film-to-film kinetic friction of less than 0.20 to allow the drape to slip into place on the basin bottom. The drape has a device layer sized sufficiently to cover the top of the fluid heating device and extend downward around a perimeter of the fluid heating device while a portion of the device layer is in proximity to the basin. In contrast to the basin layer, the device layer having a coefficient of film-to-film kinetic friction of more than 0.50 to help prevent unintended movement of the drape relative to the fluid heating device.

Some aspects of the teachings of the present disclosure may be expressed as a drape for covering an interior of a basin and at least a top of a fluid heating device. The basin having an upper side defining a cavity for receipt of a fluid to be heated. The upper side of the basin having a basin bottom and a set of basin sidewalls running from the basin bottom to the top of the fluid heating device. The drape having a sterile vented barrier sized sufficiently to cover the upper side of the basin. The drape also having a device layer sized sufficiently to cover the top of the fluid heating device and extend downward around a perimeter of the fluid heating device while a portion of the device layer is in proximity to the basin. The device layer having a basin opening so that fluids may be poured through the basin opening into a portion of the sterile vented barrier located below the device layer and above the basin. The sterile vented barrier connected to the device layer so that the drape may be used to cover the basin and the top of the fluid heating device. The sterile vented barrier having a set of at least one vent to allow air from within the basin to pass through the vent and out of the basin above the fluid heating device and below the drape as the sterile vented barrier is inserted into the basin.

Some aspects of the teachings of the present disclosure may be expressed as a heating system for applying power to a draped basin containing liquid above a drape. The heating system having at least a first heating element in thermal contact with an underside of a basin. The heating system having at least one temperature sensor monitored by a controller that regulates a flow of electricity sent to the first heating element for use in creating heat. The heating system having at least a first air gap detector located on at the first heating element. The first air gap detector monitoring heat on a portion of the underside of the basin in proximity to the first air gap detector. The first air gap detector responding to a temperature above a first high setpoint temperature by interrupting the flow of electricity sent to the first heating element. The first air gap detector continuing the interruption of the flow of electricity sent to the first heating element until detecting a temperature below a first reset setpoint temperature which is less than the first high setpoint temperature. The heating system responding when there is an air gap in proximity to the first air gap detector. The action by the heating system protects from a severe temperature excursion by the interruption of the flow of electricity sent to the first heating element.

Some aspects of the teachings of the present disclosure may be expressed as a method for preventing a temperature excursion on a portion of a draped basin containing a liquid above a drape covering a basin. The method including adding a liquid to a draped basin. The method including using an output from a temperature sensor to determine an amount of electricity provided to a heating element in thermal connection with at least a portion of an underside of the draped basin. The method also including causing an interruption of the electricity provided to the heating element when a temperature sensed at an air gap detector exceeds a high temperature setpoint.

Some aspects of the teachings of the present disclosure may be expressed as a heating system for providing heat to a draped basin containing liquid above the drape. In addition to having at least one temperature sensor that controls a flow of electricity to the heating element, the system has at least one air gap detector in thermal contact with the heating element. Each air gap detector responding to a temperature above a high setpoint temperature for that air gap detector by interrupting the flow of electricity until detecting that the temperature has fallen below a reset setpoint temperature for that air gap detector so that an air gap in proximity to the one of the air gap detectors is prevented from causing a severe temperature excursion in a portion of the basin. Thus, the drape is protected from a local temperature excursion.

The set of air gap detectors on a heating element may be connected in series so that a single air gap detector stops the flow of electricity to the entire heating element until the temperature drops below the reset setpoint for the air gap detector that caused the interruption.

The air gap may be between the basin and the drape. The air gap may be above the drape as may happen when a cup or pitcher with a rimmed bottom traps air below the cup or pitcher. The air gap does not have to be directly above any one of the air gap detectors. The ability of air gap detectors to respond to air gaps that are not directly above the air gap detector may be enhanced by adding a heat dispersion plate of a material with elevated thermal conductivity. The heat dispersion plate may be placed between the air gap detectors and the heating element.

They system may have more than one heating element, with each heating element having one or more air gap detectors.

This summary is meant to provide an introduction to the concepts that are disclosed within the specification without being an exhaustive list of the many teachings and variations upon those teachings that are provided in the extended discussion within this disclosure. Thus, the contents of this summary should not be used to limit the scope of the claims that follow.

Inventive concepts are illustrated in a series of examples, some examples showing more than one inventive concept. Individual inventive concepts can be implemented without implementing all details provided in a particular example. It is not necessary to provide examples of every possible combination of the inventive concepts provided below as one of skill in the art will recognize that inventive concepts illustrated in various examples can be combined together in order to address a specific application.

Other systems, methods, features and advantages of the disclosed teachings will be immediately apparent or will become apparent to one with skill in the art upon examination of the following figures and detailed description. It is intended that all such additional systems, methods, features and advantages be included within the scope of and be protected by the accompanying claims.

BRIEF DESCRIPTION OF THE FIGURES

The disclosure can be better understood with reference to the following figures. The components in the figures are not necessarily to scale, emphasis instead being placed upon illustrating the principles of the disclosure. Moreover, in the figures, like reference numerals designate corresponding parts throughout the different views.

FIG. 17 is a flowchart of a process 1000 for using a drape 300 in a basin 202 in a fluid heating device 200.

DETAILED DESCRIPTION

The presently disclosed subject matter is described with specificity to meet statutory requirements. However, the description itself is not intended to limit the scope of this patent. Rather, the inventors have contemplated that the claimed subject matter might also be embodied in other ways, to include different steps or elements similar to the ones described in this document, in conjunction with other present or future technologies. Moreover, although the term "step" may be used herein to connote different aspects of methods employed, the term should not be interpreted as implying any particular order among or between various steps herein disclosed unless and except when the order of individual steps is explicitly described.

Figure 7:
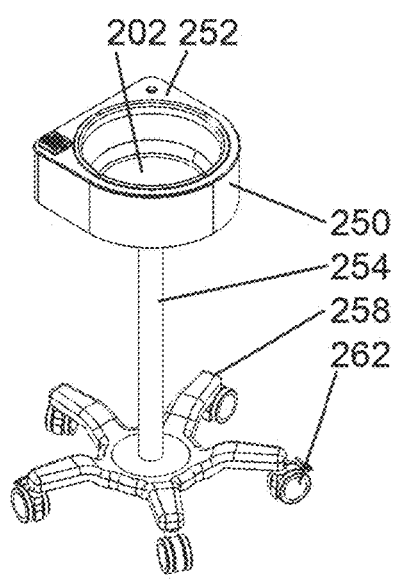
FIG. 7 introduces a new fluid heating device 200 seen here in a top and side perspective view with basin 202 recessed in a cavity in the upper portion 250 of the fluid heating device 200.

FIG. 7 introduces a new fluid heating device 200 seen here in a top and side perspective view with basin 202 recessed in a cavity in the upper portion 250 of the fluid heating device 200. An intermediate portion 254 such as a pole connects the upper portion 250 to the lower base 258 which may have a set of wheel assemblies 262 to allow for movement of the fluid heating device 200.

Figure 8:
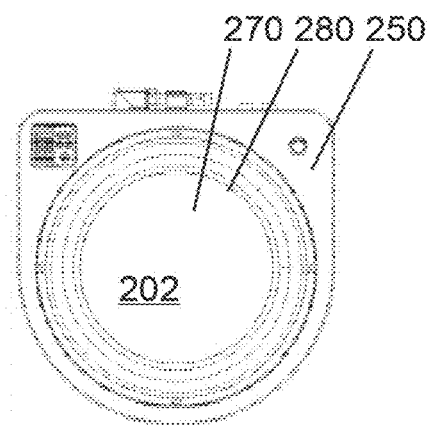
FIG. 8 is a top view of the upper portion 250 of the fluid heating device 200 showing the top view of the basin 202.

FIG. 8 is a top view of the upper portion 250 of the fluid heating device 200 showing the top view of the basin 202. The inner perimeter 280 of the basin bottom 270 is visible in FIG. 8.

Figure 9:
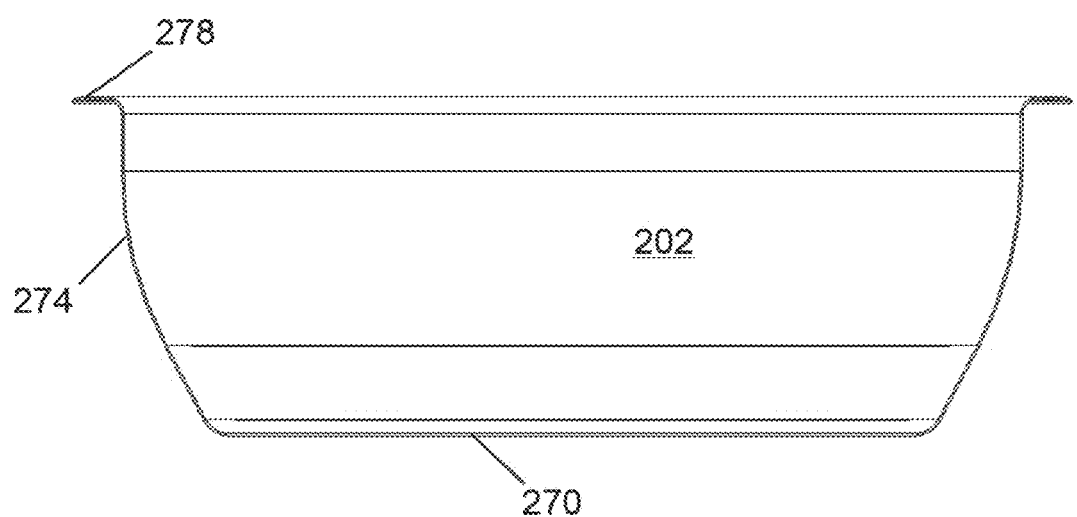
FIG. 9 is a cross section of the basin 202.

FIG. 9 is a cross section of the basin 202. The basin bottom 270, basin sidewalls 274, and flared basin rim 278 are visible in this view. The flared basin rim 278 would extend onto the top surface of the upper portion 250 beyond the cavity in the upper portion 250 that holds the basin 202. The basin 202 may be affixed to the upper portion 250 and not intended for removal by end users.

Dual Layer Drape with Centering Frame.

Figure 10:
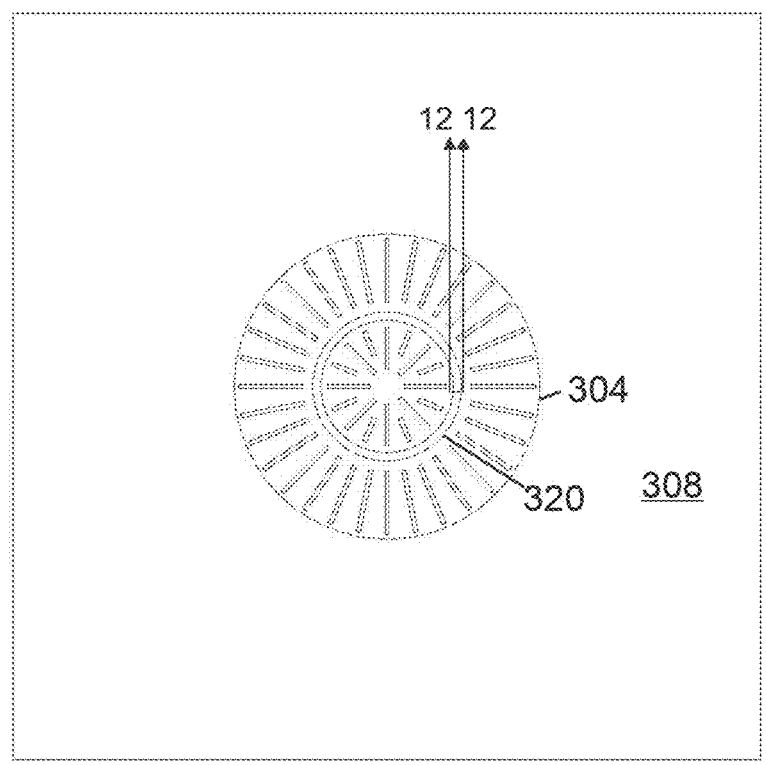
FIG. 10 is a top view of drape 300.
Figure 11:
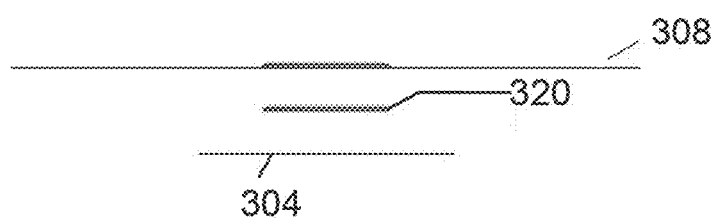
FIG. 11 shows the various layers that form drape 300.

FIG. 10 is a top view of drape 300. FIG. 11 shows the various layers that form drape 300. The drape 300 is formed of a bottom layer 304 that is sized to line the basin 202 including basin bottom 270 and at least most of the basin sidewalls 274. The bottom layer 304 may optionally extend to cover the flared basin rim 278 and a small portion of the top of the fluid heating device 200.

Above the bottom layer 304 is a perimeter frame 320 sized to fit on the basin bottom 270 and within the perimeter defined by the connection of the basin sidewalls 274 to the basin bottom 270. The perimeter frame 320 provides several benefits.

The perimeter frame 320 ensures correct alignment of the drape 300 to the basin 102 and thus to the fluid heating device 200.

The perimeter frame 320 not only assists in initial alignment but serves to maintain the proper position of the drape 300 relative to the basin 102 and fluid heating device 200 as small forces on the drape 300 are not able to force the perimeter frame 320 from the proper position within the perimeter of the bottom surface of the basin 102.

The perimeter frame 320 also ensures that effective heat transfer takes place without large air pockets developing to inhibit heat transfer from the basin 102 to the drape 300.

A second consequence of not having air pockets is the avoidance of hot spots on the surface of the basin 102 which could lead to a thermal excursion of drape material above the softening temperature if the drape material above an air pocket suddenly is repositioned to make contact with a hot spot on the basin 102.

Above the perimeter frame 320 is a top layer 308 which is sized to cover not only the basin 202 but also the top surface 252 of the upper portion 250 of the fluid heating device 200 including the sides of the upper portion 250. The top layer 308 may be sized so that the top layer extends down approximately eighteen inches below the top surface 252 of the upper portion 250.

Figure 12:
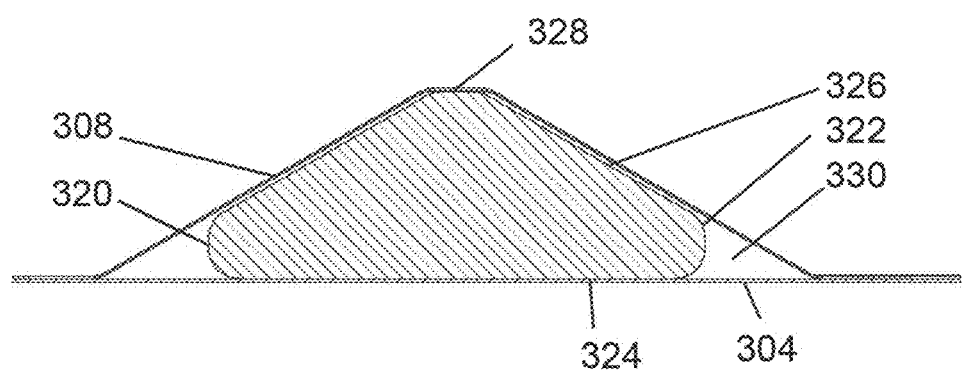
FIG. 12 is an enlarged cross section of the perimeter frame shown in FIG. 10.

A cross section of FIG. 10 is shown in FIG. 12. In FIG. 12 an enlarged cross section of a portion of the perimeter frame 320 is shown above bottom layer 304 and below top layer 308. The bottom side 324 of the perimeter frame 320 is flat to help the perimeter frame 320 and bottom layer 304 lay flat on the basin bottom 270. The perimeter frame 320 is shown here with rounded corners 322, with sloped faces 326 leading to a flat top 328. Other cross sections are possible such as replacing the flat top 328 with a rounded surface.

Note that the image in FIG. 12 is enlarged so the air gap 330 defined by the rounded corner 332 of the perimeter frame 320 and the bottom layer 304 and top layer 308 are enlarged. As there are bonding locations 340 joining the bottom layer 304 to the top layer 308 both inside and outside of the perimeter frame 320, there is not relative motion of the top layer 308 relative to the bottom layer 304, thus the air gap 330 does not collapse under weight of the liquid 120. It is important to note that the size of this air gap 330 is relatively small, perhaps not more than 70 thousandths of an inch of maximum height. Having less of a rounded edge to the perimeter frame 320 could further reduce the size of the air gap 330 but the perimeter frame 320 may serve as a thermal insulator so expanding the footprint of the perimeter frame 320 to decrease the air gap may not improve thermal performance.

The perimeter frame 320 may be made of a suitable polymer such as polypropylene, ABS, or polycarbonate. The perimeter frame 320 would be sterilized, most likely during the sterilization of the drape assembly. Ideally the surfaces of the perimeter frame 320 would have sufficient texture so that air may pass between the perimeter frame 320 and the top layer 308 and between the perimeter frame 320 and the bottom layer 304 to allow air to pass from between the bottom layer 304 and top layer 308 when liquid 120 is added to the draped basin 202. If necessary, the perimeter frame 320 may be made with ribs to promote the passage of air between the perimeter frame 320 and the bottom layer 304 and between the perimeter frame 320 and top layer 308. Through holes in the perimeter frame 320 to allow venting would be another option although this may prolong the sterilization process.

Differences in Drape Layer Textures.

Figure 13:
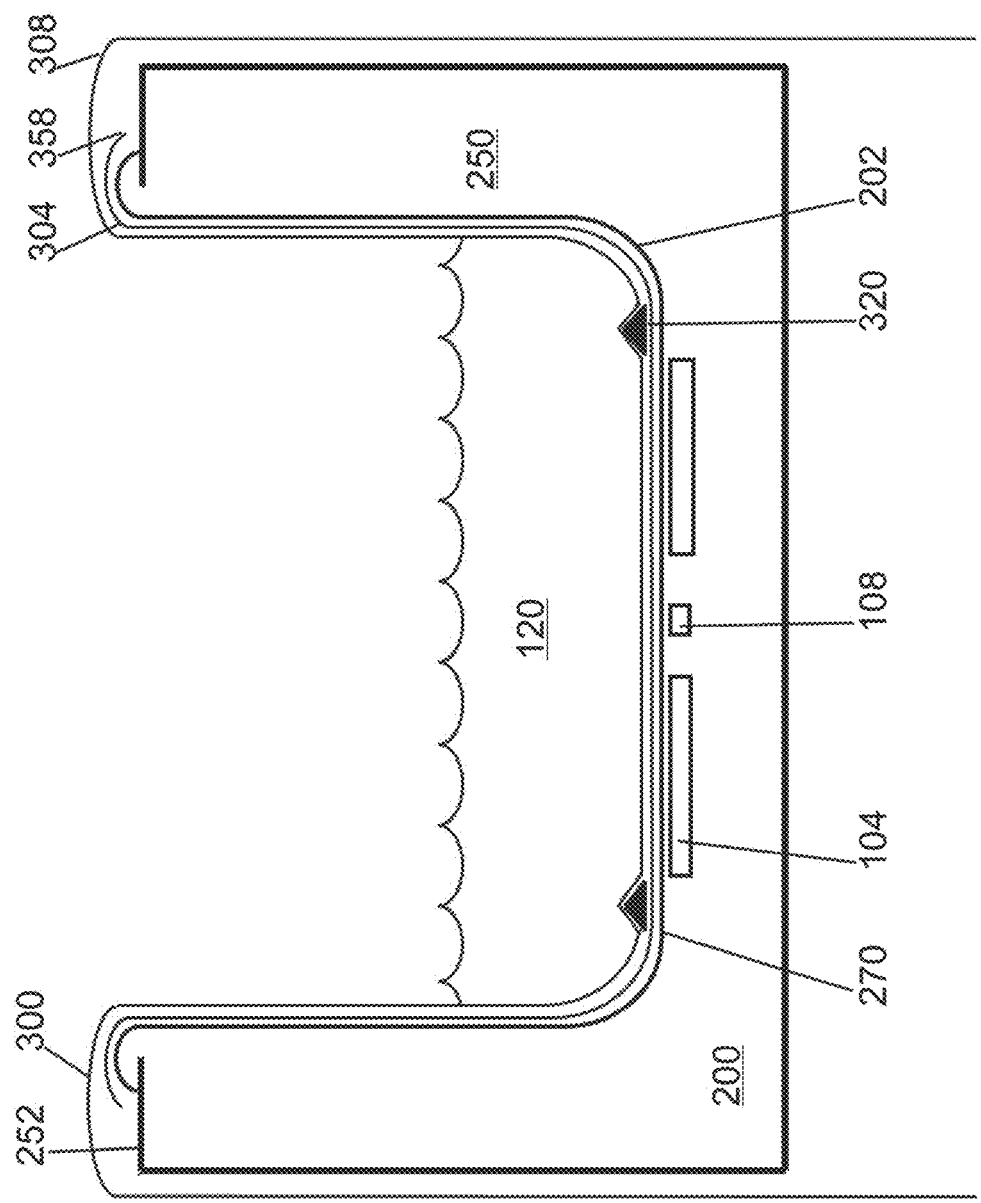
FIG. 13 is a cross section of a fluid heating device 200 that has been covered by a drape 300 with a perimeter frame 320.

FIG. 13 is a cross section of a fluid heating device 200 that has been covered by a drape 300 with a perimeter frame 320. Visible in FIG. 13 are a basin 202 which is in proximity to two heating elements 104 (possibly an annular shaped heating element) with a temperature sensor 108. A drape 300 with a bottom layer 304 and a top layer 308 has a perimeter frame 320 trapped in place by a set of bonding locations 340 (not shown here). The top layer 308 spills out over the top surface 252 of the fluid heating device 200. The bottom layer 304 is smaller than the top layer 308 and thus defines an overlapped portion 358. In order to show the top layer 308 as distinct from the bottom layer 304, the drawing includes gaps between the two layers which would not be present after the addition of liquid 120 as air would move outward as the bonding locations 340 are in a pattern that does not block the movement of air away from the basin bottom 270.

The bottom layer 304 of the drape 300 may be slick so that the bottom layer 304 slides into proper position within the basin 202 with minimal resistance and reduced risk of wrinkles on the basin bottom 270. Conversely, the bottom side of the top layer 308 of the drape 300 may be non-slick so that the drape 300 once positioned on the basin 202 and fluid heating device 200 has additional resistance to movement out of position due to the interaction between the bottom side of the top layer 308 and the top surface 252 of the upper portion 250 of the fluid heating device 200. The non-slick property of the top layer 308 may be a property of the drape material and not the product of an added layer of low tack adhesive.

Bottom layer 304 is sized so that once the bottom layer 304 is in place the bottom layer 304 extends slightly over the top of the metal basin 202 but not over much of the top surface 252 of the upper portion 250 of the fluid heating device 200. When the drape 300 is initially flat and at the top of the fluid heating device 200 (i.e. not yet pressed into the basin 202) the slick bottom layer 304 extends out over the top of the fluid heating device 200 and slides easily while the drape 300 is pressed downward into the basin 202. The sliding is easy up until the point the drape 300 is almost fully seated. Just before seating, the slick bottom layer 304 has passed the perimeter of the top surface 252 of the upper portion 250 of the fluid heating device 200 and the non-slick top layer 308 is now contacting the top surface 252 of the upper portion 250 of the fluid heating device 200 and prevents uncontrolled or unintended movement of the whole drape 300.

High-Slip vs. Non-Slip Films.

Those of skill in the art recognize that the dry kinetic coefficient of friction of a film in contact with itself (film-to-film) is a useful parameter for selecting films for a particular purpose. Kinetic friction is a dimensionless parameter measured after initial motion has started as opposed to static friction. A film-to-film coefficient of kinetic friction of less than 0.20 is considered to be a low-slip film. In contrast, a film-to-film coefficient of kinetic friction of more than 0.50 is considered to be a non-slip surface. See https://web.archive.org/web/20180430160133/http://www-.polyprint.com/flexographic-friction.htm (spaces added to prevent a live link).

A film found suitable for the bottom layer 304 to slip into place on the basin was tested by an external lab and the kinetic coefficient of friction measured in accordance with ASTM D-1894 ranged from 0.13 to 0.16 with a mean of 0.14. This would be a low-slip film.

In contrast, a film found suitable for the top layer 308 to contact the top surface 252 of the upper portion 250 of the fluid heating device 200 and prevent uncontrolled or unintended movement of the whole drape 300 was tested by an external lab and the kinetic coefficient of friction measured in accordance with ASTM D-1894 ranged from 0.79 to 0.91 with a mean of 0.86. This would be a non-slip surface.

Thus a preferred embodiment would use a low-slip film for the basin contact area of the drape and a non-slip film for at least a portion of the drape beyond the basin.

Figure 14:
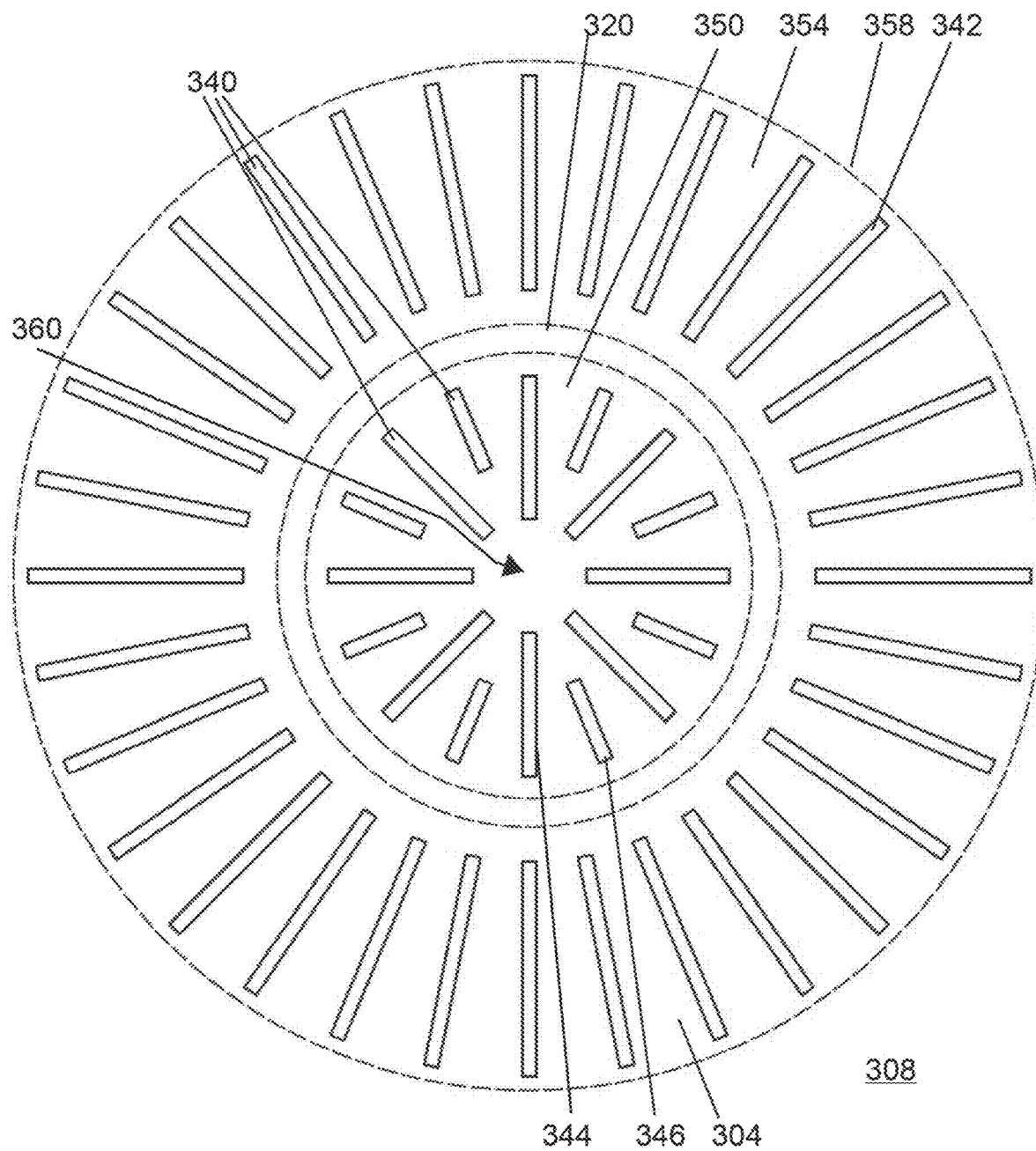
FIG. 14 shows an enlarged portion of the drape 300.

FIG. 14 shows an enlarged portion of the drape 300. In FIG. 14 the outer perimeter of bottom layer 304 is shown surrounded by top layer 308. The outline of perimeter frame 320 is shown. A series of bonding locations 340 are shown. In this particular drape 300, there are three different sets of bonding locations 340. There are radial sidewall bonds 342, radial bottom bonds 344 and radial short bonds 346 between pairs of the radial bottom bonds 344.

This pattern of bonding locations 340 allows air initially present between the top layer 308 and the bottom layer 304 in the basin bottom portion 350 of the drape 300 to move outward past the perimeter frame 320 and up the basin sidewall portion 354 of the drape 300 and out of the overlapped portion 358 of the top layer 308 and bottom layer 304. The bonding locations 340 are substantially radial relative to a center point 360 of the basin bottom portion 350 of the drape 300.

While a radial orientation is logical, those of skill in the art will appreciate that the bonding locations 340 could be arranged to be other than radial as long as the deviation from radial is not sufficient to allow air to be blocked from easy exit from the overlapped portion 358 of the drape 300. Thus, a set of parallel bonding locations would be sub-optimal although viable as this may impede some air from rising up the basin sidewall for at least a portion of the basin perimeter.

The bottom layer 304 and the top layer 308 may be made from polyurethane material. As noted above, the bottom layer 304 may differ from the top layer 308 in slip characteristics to promote fit and function. The bonding locations may be formed by heat seals as is known in the art. The heat seals may be approximately one quarter of an inch wide but this may be adjusted during the manufacturing process to select a heat seal that is sufficient to bond the bottom layer 304 to the top layer 308 and trap the perimeter frame 320 without damaging the drape 300. Note that a solid bond forming a continuous perimeter is not present including in the vicinity of the perimeter frame 320 or the outer boundary of the overlapped portion 358.

A preferred method for creating drape 300 is to place the bottom side 324 of the perimeter frame 320 on the bottom layer 304 and then place the top layer 308 over the perimeter frame 320 so that there is sufficient extra material for the top layer 308 so that the bottom layer 304 does not have any wrinkles which would capture air and impede heat transfer from the basin bottom 270 through bottom layer 304 of the drape 300.

Ideally, the locations for the perimeter frame 320 after drape placement and the placement of the heating elements 104 and temperature sensor 108 are selected so that a properly placed drape 300 does not have a perimeter frame over a heating element 104 or a temperature sensor 108. As the outer perimeter of the perimeter frame 320 may be slightly less than the perimeter of the basin bottom 270 defined by the interiors of the set of basin sidewalls 274, the perimeter frame 320 will have some small range of possible positions. It is possible in some designs that a perimeter frame 320 at an extreme allowed position may overlap a heating element by less than an inch. Small overlaps may be tolerable as the heat conduction of liquid and of the round basin 202 near that small overlap will avoid having the heat form an elevated temperature under the perimeter frame anywhere close to the softening temperature of the drape material.

Optionally, the bottom layer 304 may be a different thickness than the top layer 308. For example, the top layer 308 may be 5 mil polyurethane and the smaller bottom layer 304 may be 2 mil polyurethane to provide additional protection against breach of the drape 300 within the basin 202. The bottom layer 304 also serves to hold the perimeter frame 320 in location and may be used to provide a slick surface for positioning the drape 300 in the round basin 202.

Alternatively, the large top layer 308 may be thinner than the smaller bottom layer 304. This may provide an opportunity for cost savings.

Air Gap Detector s.

While prior art heating devices had a secondary temperature sensor located in proximity to temperature sensor 108 to serve as a backup to avoid a runaway application of energy to the heating elements 104 if primary temperature sensor 108 failed, the present disclosure provides an improvement.

The present disclosure provides a set of temperature sensors close to the perimeter of the basin 102. These temperature sensors will also serve to prevent a runaway application of energy should the primary temperature sensor 108 fail, but more importantly these temperature sensors will cause all or at least a portion of the heating elements to cease applying heat if the perimeter temperature sensors detect an elevated temperature as might be found when an air gap is causing a portion of the basin 102 to get hot as the air gap 128 is limiting the transfer of thermal energy to the sterile liquid 120.

The air gap detectors may be set to disable the heater element or a fraction of the heater elements when reaching an elevated temperature such as 300 degrees Fahrenheit. The hot temperature may be selected to avoid temperature excursions in excess of the softening temperature of the drape material. Once the air gap detector has noted a temperature excursion the air gap detector may stop power flow to a heater or a subset of heaters until the temperature drops a significant amount.

For context, the deadband may be 30 degrees Centigrade (86 degrees Fahrenheit) so that the temperature sensed by the air gap detector would need to drop to 214° F. before additional energy is provided to the heater or subset of heaters.

Figure 1:
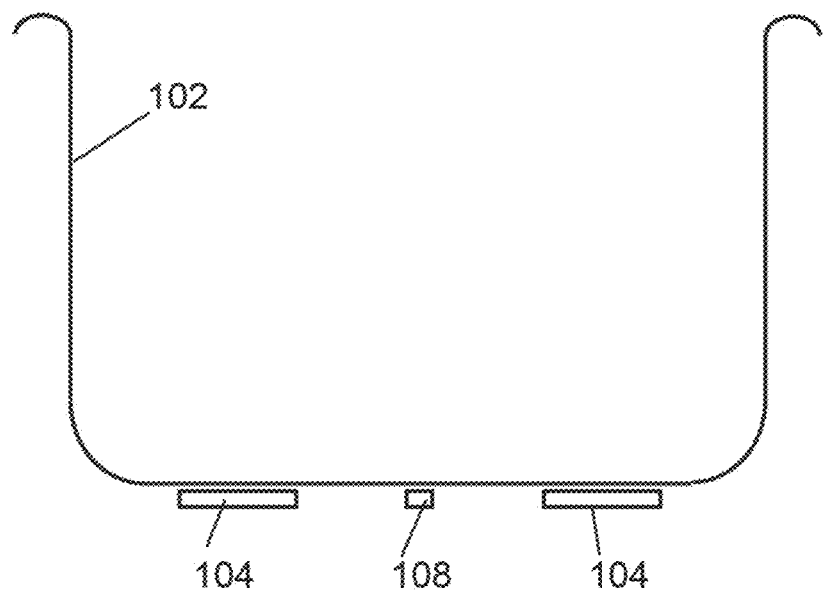
FIG. 1 shows a cross section of a prior art fluid heating device.
Figure 2:
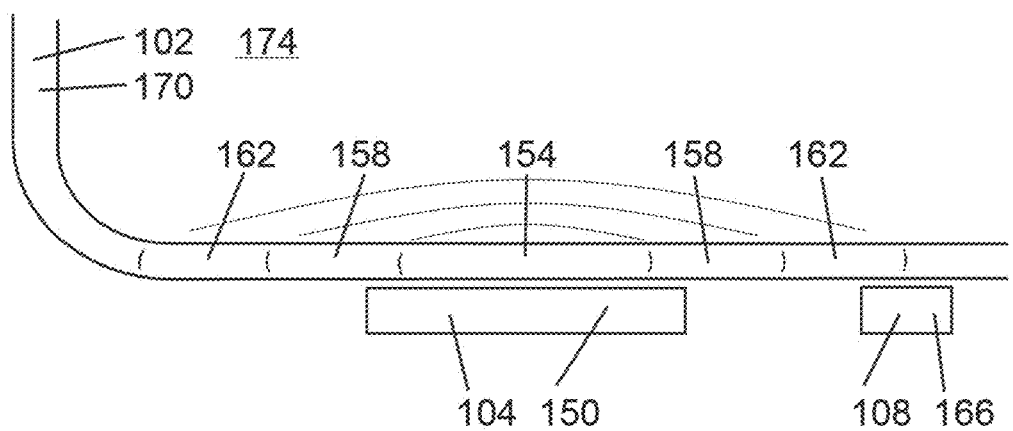
FIG. 2 is an enlarged representation of a portion of FIG. 1.
Figure 3:
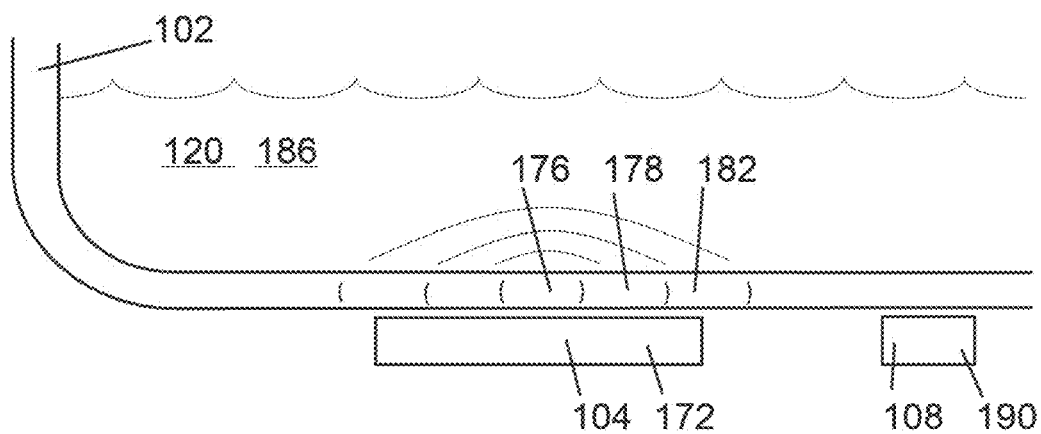
FIG. 3 shows FIG. 2 with liquid added.
Figure 4:
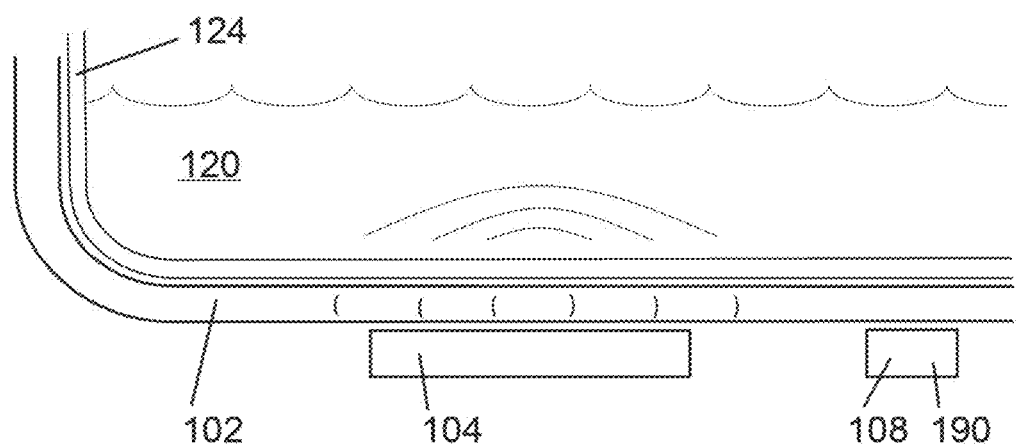
FIG. 4 shows FIG. 3 with a flexible drape lining the basin and containing liquid.
Figure 5:
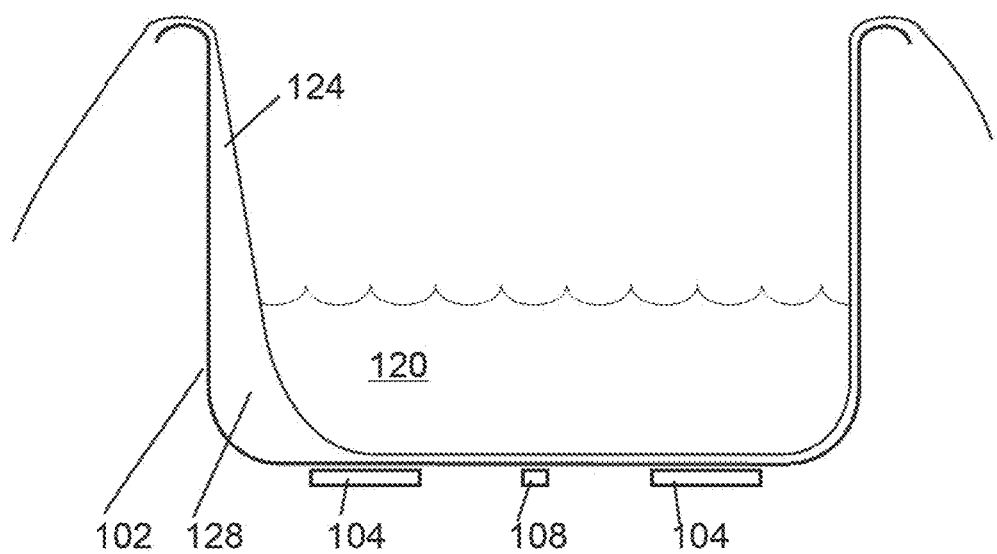
FIG. 5 shows the basin with a flexible drape and the liquid and an air gap.
Figure 6:
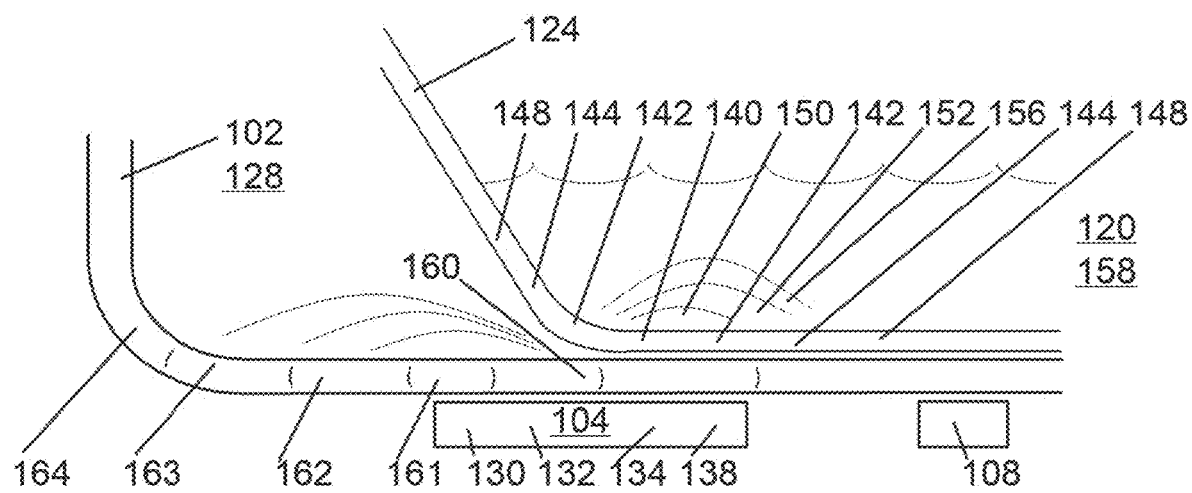
FIG. 6 shows a close up of the air gap area of FIG. 5.
Figure 15:
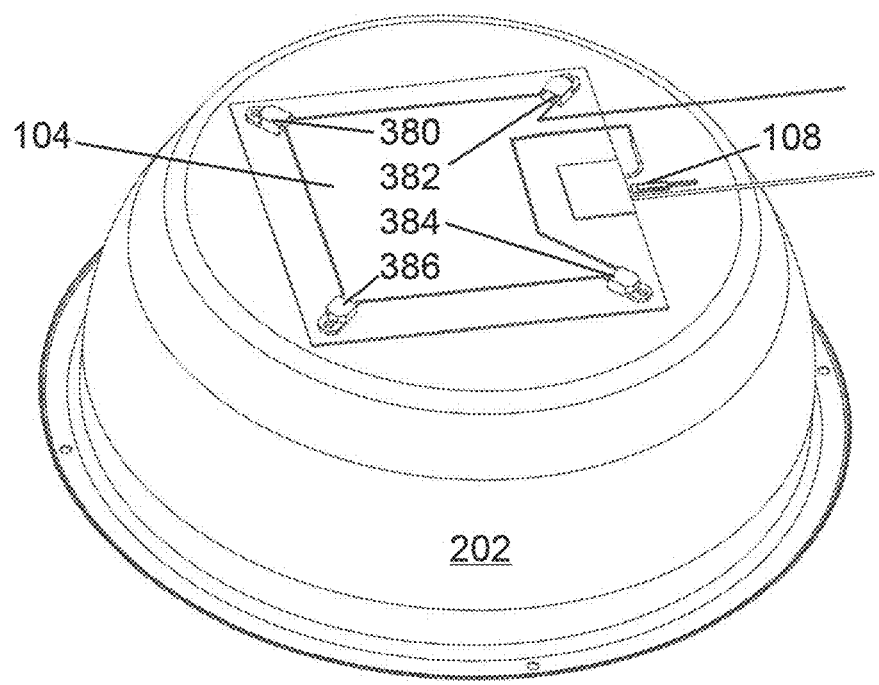
FIG. 15 shows a bottom perspective view of basin 202.

FIG. 15 shows a bottom perspective view of basin 202. In FIG. 15 there is a first arrangement of air gap detectors 380, 382, 384, and 386 positioned below heating element 104. These air gap detectors 380, 382, 384, and 386 are in series. If any one of these air gap detectors 380, 382, 384, and 386 senses a temperature in excess of the interrupt setpoint, the air gap detector will open the circuit and stop the flow of energy to the heating element 104. Thus, the air gap detectors 380, 382, 384, and 386 provide redundancy to temperature sensor 108 but also interrupt power to the heating element in the event that the drape 300 (not shown here) is not positioned in a manner that avoids an air gap (128 in FIG. 6). The use of the air gap detectors 380, 382, 384, and 386 provides a system that will periodically interrupt the flow of power to the heating element 104 so that the temperature of the basin 202 below the air gap will not rise to temperatures that are above the melting temperature for the drape 300.

Figure 16:
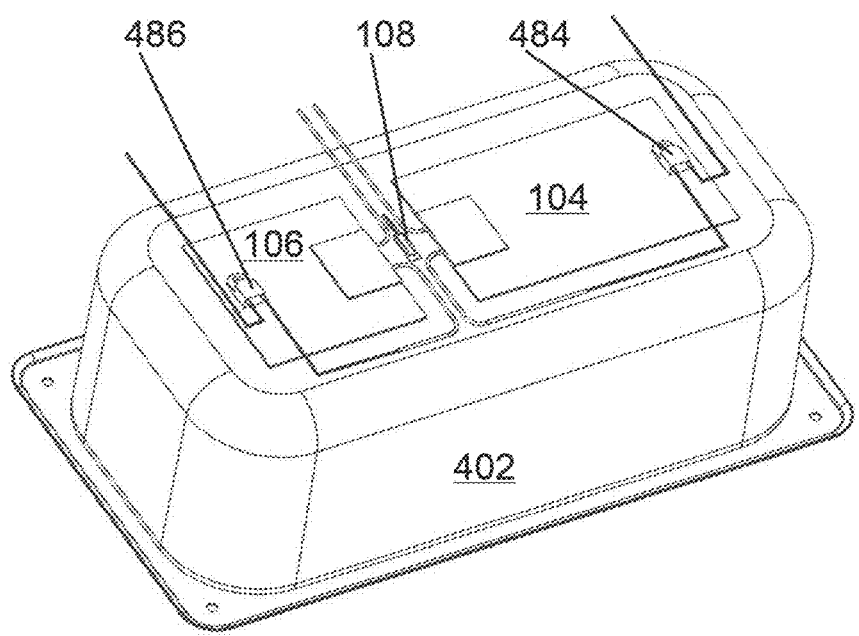
FIG. 16 shows a bottom perspective view of rectangular basin 402.

FIG. 16 shows a bottom perspective view of rectangular basin 402. Visible in FIG. 16 are two heating elements 104 and 106. Each heating element 104 and 106 has an air gap detector 484 and 486. Thus, if temperature sensor 108 fails, eventually air gap detectors 484 and 486 will interrupt power to heating elements 104 and 106 although the interruptions may not begin or end at the exact same time. More importantly, if drape 450 is positioned in such a way as to leave an air gap near either end of the rectangular basin 402, the relevant air gap detector 484 or 486 will periodically interrupt the flow of power to the relevant heating element 104 or 106 so that the temperature of the rectangular basin 402 below the air gap will not rise to temperatures that are above the melting temperature for the drape.

Those of skill in the art will appreciate that using off-the-shelf heating elements is more cost effective than using custom-made heating elements. Thus heating elements 104 and 106 are not the same size in order to use off-the-shelf heating elements.

Those of skill in the art may take the teachings from FIG. 15 and FIG. 16 to create basins with different numbers of heating elements and air gap detectors. A basin heating system may have several heating elements with at least one of the heating elements having more than one air gap detector. There is a trade-off between having a high number of heating elements, each with one or more air gap detectors, and the simplicity of having one heating element and several air gap detectors connected in series. Different designers with different priorities may choose to use one heating element or many heating elements while staying within the teachings of the present disclosure.

One can imagine an array of eight pie-piece heating elements placed beneath a round basin 202 and around a central temperature sensor 108. Each pie-piece heating element may have an air gap detector at each distal corner so that an air gap that causes a local rise in basin temperature may cause only one or two pie-shaped heating elements to stop heating.

Likewise, one could imagine a set of small heating elements for a rectangular or square basin that would have one or more air gap detectors per heating element so that air gaps that would cause local hot spots are not overheated while quickly applying heat to other portions of the basin without an air gap.

Those of skill in the art will be able to select a suitable air gap detector based upon the softening temperature of the drape material and other criteria. An example of an air gap detector that will be suitable for some applications is Dig-Key part number 317-1580-ND manufactured by Cantherm with Cantherm Part Number F20A15005DCFB06E with a switching temperature of 150 degrees Centigrade and a reset temperature of 120 degrees Centigrade.

A system may use a first air gap detector set to interrupt power at a first temperature and a second air gap detector set to interrupt power at a second temperature different than the first temperature. For example, an air gap detector located in the center of the basin may be set to operate to interrupt power at a different temperature than an air gap detector located near a perimeter of the basin bottom. A system may use at least one air gap detector without a sizable gap between the trigger temperature to interrupt power and the reset temperature. Thus rather than having a 30-degree Centigrade gap between the trigger temperature and the reset temperature, the system could have a gap of just one degree Centigrade so that the system applies as much heat as possible to the basin without exceeding the trigger temperature.

The use of air gap detectors to interrupt power to a heating element can be used in systems that vary the amount of power provided to the heating element by varying the current provided, varying the voltage provided, or varying a duty cycle for the energy provided to the heating element.

The air gap detectors may be placed in direct contact with a heating device as shown in FIG. 15 and FIG. 16 but this is not required. The air gap detectors could be placed upon the underside of the basin (202 or 402) or a sidewall of the basin (202 or 402) but wired to the nearby heating element to interrupt power provided to that heating element upon detection of an elevated temperature. One of skill in the art can determine an appropriate high temperature setpoint depending on the proximity of the air gap detector to the heating element and other geometry.

Process for Using Drape.

A process 1000 for using a drape 300 in a basin 202 in a fluid heating device 200 is set forth in FIG. 17.

Step 1004-Place sterile drape 300 over the upper portion 250 of a fluid heating device 200 with an emphasis on placing the flat bottom side 324 of the perimeter frame 320 within the inner perimeter (FIG. 8) of the basin bottom 270 (FIG. 8). This placement will place the bottom layer 304 within the basin 202 so that the basin 202 has two layers of drape material and will position the top layer 308 in the intended position to hang down over the sides of the upper portion 250 of the fluid heating device 200.

Step 1008-Add a volume of sterile fluid to the draped basin 202. The minimum volume of liquid to be used with a particular fluid heating device may be specified to ensure that the basin has an adequate amount of sterile fluid. As the bottom layer 304 is bonded to the top layer 308 and stretched by the perimeter frame 320 captured between the bottom layer 304 and the top layer 308, the bottom layer 304 is free of wrinkles within the area defined by the perimeter frame 320 and thus will make good contact with the basin bottom 270. As the volume of sterile fluid is added to the draped basin 202 the liquid forces any air between the top layer 308 and the bottom layer 304 to move from within the area defined by the perimeter frame 320, past the perimeter frame 320 and up the basin sidewalls 274 (FIG. 9) between the top layer 308 and the bottom layer 304 to exit the overlapped portion 358 of the top layer 308 and bottom layer 304.

Step 1012-Apply heat to the bottom side of the basin 202, through the basin 202, through the bottom layer 304, and through the top layer 308 to heat the volume of sterile liquid in the basin 202.

Step 1016-Temperature controller monitors fluid temperature as indicated by temperature sensor 108 and automatically regulates power output to the one or more heating elements to heat the sterile fluid to a desired temperature setpoint.

Step 1020-Optionally, air gap detectors monitor for temperature excursions that may indicate an air gap above the air gap detector. One or more air gap detectors are located near the edges of the basin on the one or more heating elements.

Step 1024-Interrupt power to the relevant heating element upon detection of a temperature excursion close to the softening temperature for the drape.

Step 1028-End interruption of power to the relevant heating element when the monitored temperature at the air gap detector falls below a setpoint.

Material Choices.

The drapes may be made from aromatic polyester polyurethane films such as the DUREFLEX® PS7000 family as they have relatively high softening temperatures and other desirable qualities. The drape material can be obtained in 5 mil thickness, 2 mil thickness, and other thicknesses as desired. The films can be modified to have the degree of slip or tack desired for the customer application.

Alternatives and Variations

Rectangular Basin.

Figure 19:
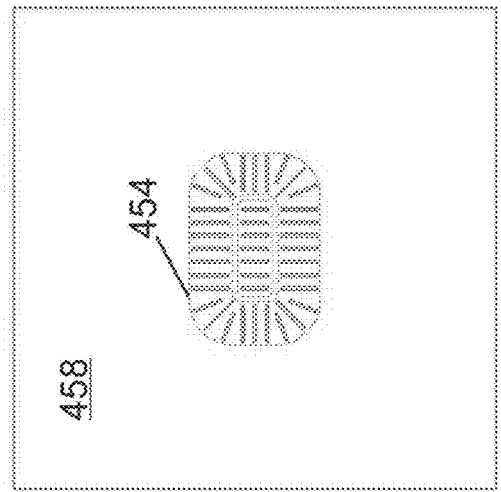
FIG. 19 is a top view of a drape 450 for use with fluid heating device 400.
Figure 20:
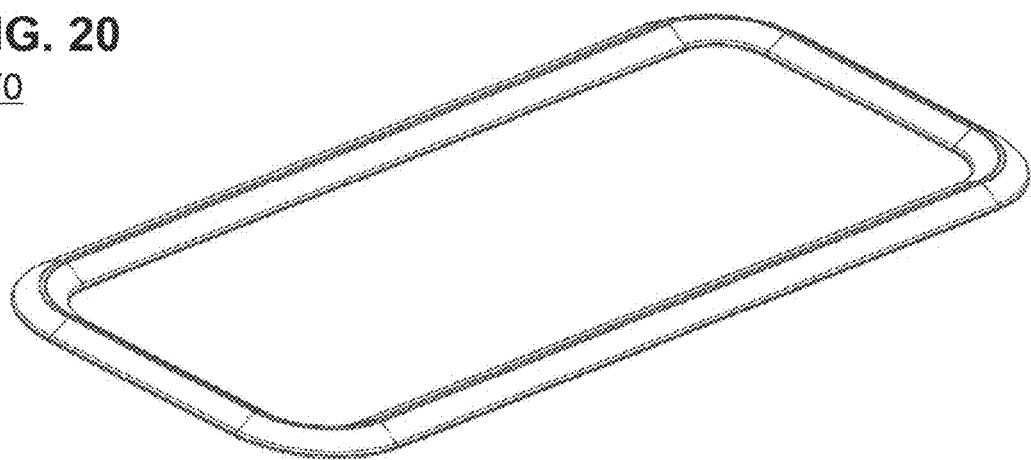
FIG. 20 shows a perimeter frame 470 shaped to fit within the perimeter of the basin bottom 404 and position the drape 450 with respect to the rectangular basin 402.

While the round basin 202 shown above is one common basin shape, FIG. 18 shows a top and side perspective view of fluid heating device 400 with a rectangular basin 402 in top portion 410 which is connected by intermediate portion 254 to base 258. FIG. 19 is a top view of a drape 450 for use with fluid heating device 400. Drape 450 has a top layer 458 sized to cover the top portion 410 and extend downward. A bottom layer 454 is sized to substantially cover both the basin bottom 404 and basin sidewall 406 possibly extending outward a short distance onto the flat top of the top portion 410. FIG. 20 shows a perimeter frame 470 shaped to fit within the perimeter of the basin bottom 404 and position the drape 450 with respect to the rectangular basin 402.

Figure 21:
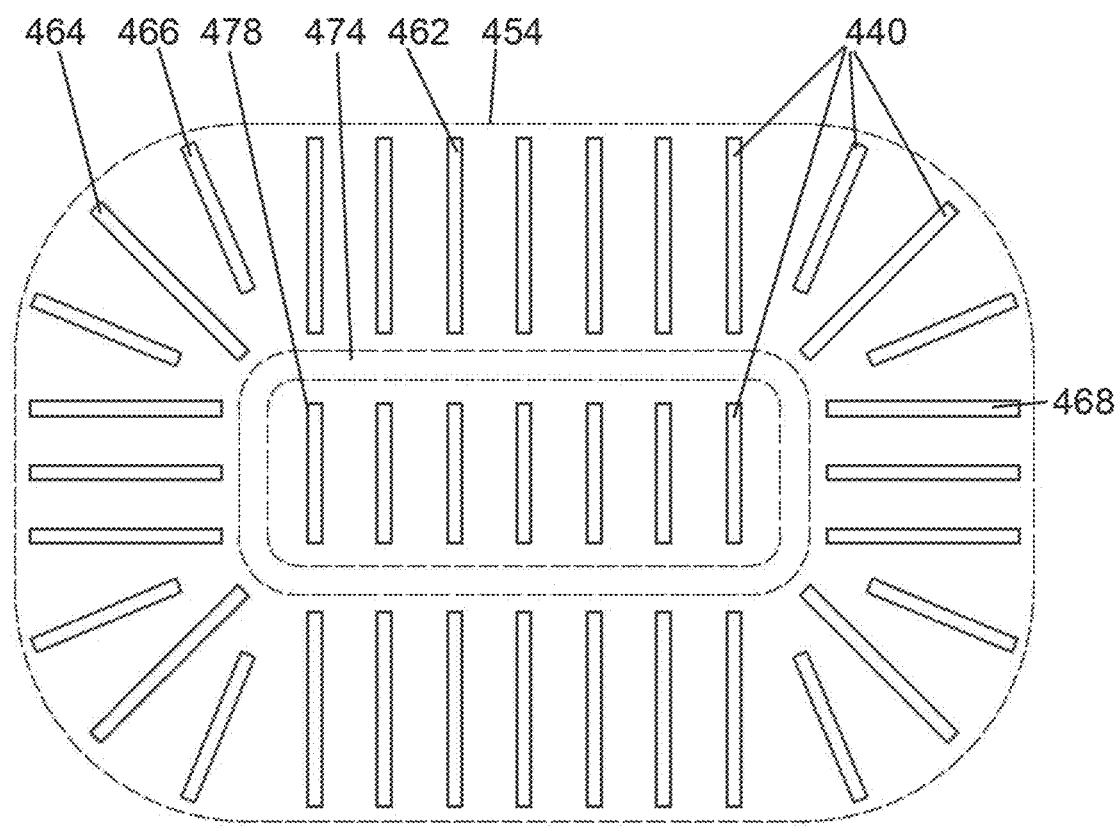
FIG. 21 is an enlarged view of a portion of drape 450.

FIG. 21 is an enlarged view of a portion of drape 450. A set of bonding locations 440 connects the top layer 458 to the bottom layer 454 and captures the perimeter frame 470 in frame zone 474. The set of bonding locations 440 are again selected to allow air to move from inside the frame zone 474 to the outer perimeter of bottom layer 454 so that air does not impede heat transfer from the rectangular basin 402 through the drape 450 to the liquid (not shown here) above the drape 450. With this elongated rectangular shape of the rectangular basin 402, one efficient pattern for the set of bonding locations 440 uses a set of parallel bonds 478 inside the frame zone 474. Long wall bonds 462 extend up the long walls 412 (FIG. 14) of the rectangular basin 402 and likewise short wall bonds 468 extend up the short walls 414 (FIG. 14) of the rectangular basin 402. Long corner bonds 464 and short corner bonds 466 are in the four rounded corners 416 (FIG. 18) of the rectangular basin 402.

Those of skill in the art recognize that the set of parallel bonds 478 inside the frame zone 474 could be oriented parallel to the long walls 412 rather than the short walls 414 of the rectangular basin 402. Or they could be at some other angle with respect to the long walls 412. The goal is to avoid forming a perimeter with the bonds that would trap air.

Other than the differences to accommodate the rectangular basin 402 as opposed to the round basin 202, drape 450 may be identical to the drape 300 discussed above.

Smaller Second Layer as Top Layer.

As shown in FIG. 11 the bottom layer 304 is the smaller basin sized layer that is sized to provide additional protection against puncture for the basin bottom 270, and at least a portion of the basin sidewalls 274, and possibly extend to cover the basin rim 278. As an alternative embodiment, the basin sized layer could be the top layer. Using the basin sized layer as the top layer may require a slightly larger basin sized layer so that the seam between the basin sized layer and the larger drape layer is moved outward from the edge of the basin rim 278 so that there is less opportunity for movement of items into the basin 202 to catch the seam or cause fluids to enter any gaps in the seam to then be between the two layers of the drape. A complete seal around the entire perimeter of the basin sized drape may lead to some air being trapped between drape layers. So there are reasons to have gaps in the sealing bonds between the two layers of drape. But this option is viable and may have appeal to end users to have the thicker basin sized drape to be the first drape layer to receive contact from the items placed into the basin 202.

Bonds.

While heat seals between layers of polyurethane are one appropriate solution for creating a set of bonding locations, the teachings of the present disclosure are not limited to this choice. Those of skill in the art will appreciate that other bonding techniques including use of adhesives, ultrasonic welding, and other techniques known to those of skill in the art may be used with appropriate materials.

One Layer Drape.

An alternative embodiment that provides some but not all the advantages of the dual layer drapes discussed above is a single layer drape. The flat bottom side 324 of the perimeter frame 320 (for a round perimeter frame as shown in FIG. 12) would be directly adhered to a top surface of the single layer. The single layer would be analogous to top layer 308 (FIG. 11) in that the single layer would be sized to cover the upper portion 250 (FIG. 7). The perimeter frame 320 would serve the purpose of allowing the user to know the top side of the drape from the bottom side of the drape and would allow the drape to quickly be positioned appropriately as the perimeter frame 320 placed inside the basin 202 would locate and maintain the drape in the proper position relative to the basin 202 and upper portion 250. As there would not be a second layer to fortify the drape within the basin 202, the thickness of the single layer may be increased.

Note that the single layer drape could be created to work with a rectangular basin. Both frame configurations could be utilized.

The perimeter frame 320 could be bonded to either the top side of the single layer drape or to the bottom side of the single layer drape, although this choice will impact the cross section of the perimeter frame 320 so that you have a flat surface for the bonding side. If the perimeter frame 320 is bonded to the bottom side of the single layer drape, it may be useful to have some additional slack in the drape so that the drape can easily reach the basin bottom close to the perimeter frame. This problem is not present if you bond the perimeter frame 320 to the top surface of the single layer drape.

In all cases the bonding of the single layer to the perimeter frame would ensure that the portion of the drape within the perimeter defined by the perimeter frame would be wrinkle-free (if the single layer drape was wrinkle-free when bonded to the perimeter frame). This wrinkle-free portion of the single layer drape would be efficient in allowing heat transfer through the single layer drape.

The bonding methods could be heat seal between the perimeter frame (which may be made of polycarbonate) and the drape material that may be made of polyurethane. Adhesives and ultrasonic welding may be used instead of heat seals.

Basin Shapes.

This disclosure gave examples using round basin 202 and rectangular basin 402. As it would be unnecessary to inform one of skill in the art, not every comment made about uses of a drape with a round basin 202 was repeated when discussing rectangular basin 402. Likewise, not every comment made about uses of a drape with a rectangular basin 402 was repeated when discussing round basin 202. Those of skill in the art can take any teaching illustrated when discussing one basin shape and apply that teaching to another basin shape. Further, the teachings of the present disclosure are not limited to drapes that fit a round basin or a rectangular basin. Other basin shapes may be used such as square or oval. A basin may have one wall that is not shaped the same as the other walls. For example, one wall of a rectangular basin could be curved outward. A basin may have a bottom that is not flat but is sloped or has a deeper portion which may be called a well. These basins may be adapted to received laparoscopes or other medical devices.

Choices of basin shapes may impact the placement of heating elements and air gap detectors and the shape of a perimeter frame or non-perimeter positioning device such as a reticle but these variations would be within the skill of the art after reviewing the teachings of this disclosure. Teachings of the present disclosure could be used for basins with sloped bottom surfaces such as for scope heating.

Dual-Use Drapes.

Figure 18:
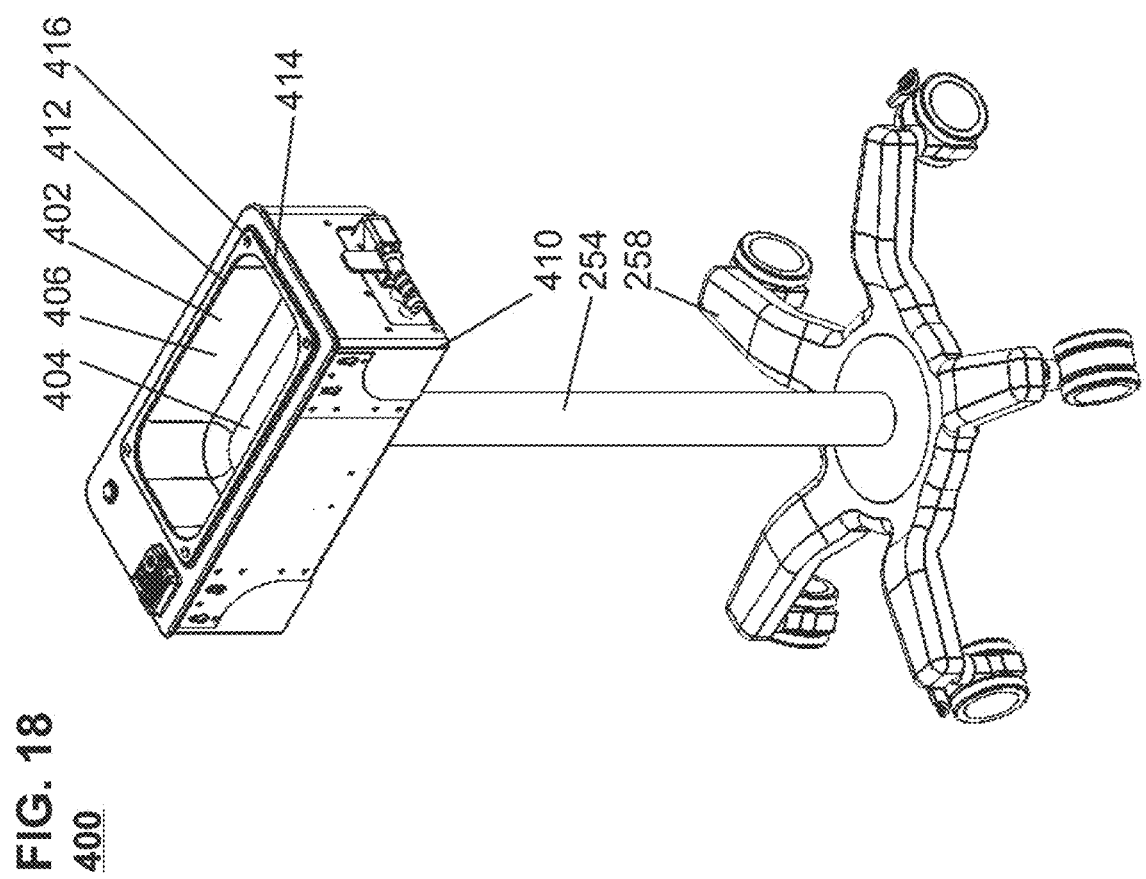
FIG. 18 shows a top and side perspective view of fluid heating device 400 with a rectangular basin 402 in top portion 410 which is connected by intermediate portion 254 to base 258.
Figure 22:
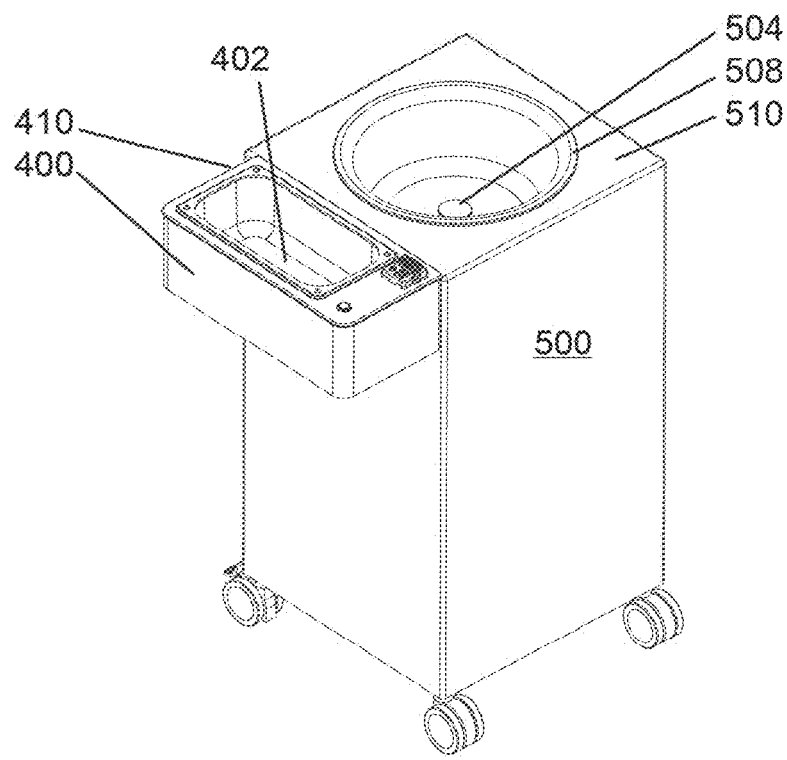
FIG. 22 shows that the top portion 410 of a fluid heating device 400 such as shown in FIG. 18 could be side mounted to a slush-making device 500.

Those of skill in the art will appreciate that the top portion 410 of a fluid heating device 400 such as shown in FIG. 18 could be side mounted to a slush-making device 500 as shown in FIG. 22. Slush-making device 500 is a prior art slush-making machine with a center disc 504 in basin 508. The center disc 504 pushes a drape disc 554 as this type of slush-making device 500 agitates the slush that forms in the drape where the drape contacts the chilled surfaces of the basin 508. Having a center disc 504 rise and fall reduces the amount of effort from the surgical staff to release frozen material from the drape's walls of the basin 508.

Figure 23:
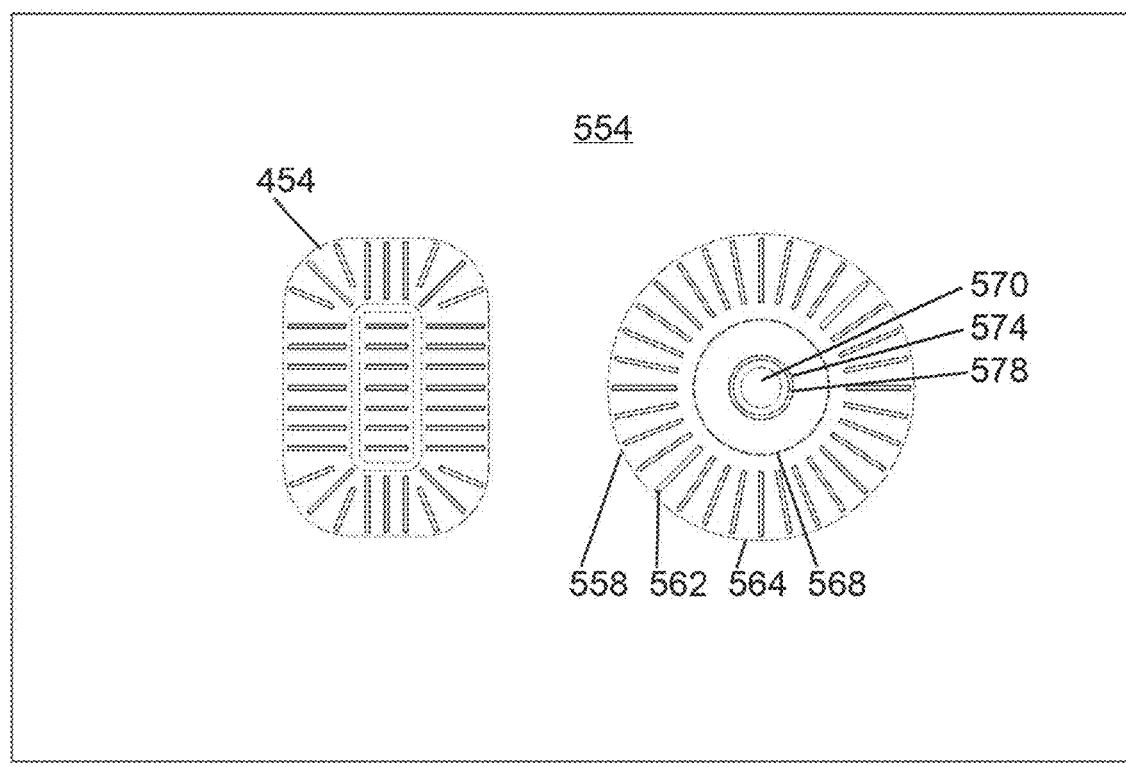
FIG. 23 shows a top view of a dual-use drape 550 for use with the device of FIG. 22.

FIG. 23 shows a top view of a dual-use drape 550 that has an upper layer 554 which is larger than the top layers 308 or 458 discussed above. One side of dual-use drape 550 will cover the rectangular fluid heating device 400 and may have a bottom layer 454 as described in connection with FIG. 21. The other side of dual-use drape 550 is adapted to cover the basin 508 and top surface 510 of slush-making device 500.

As labeled in FIG. 23, a basin layer 558 may be bonded to the upper layer 554 by a series of radial bonds 562. The edge of the overlap of the two layers is shown by edge 564.

Cap 570 with downward facing rim 574 is adapted to snap onto the center disc 504 of the slush-making device 500 so that the dual-use drape 550 moves with the movement of the center disc 504. The specifics of the friction fit or other way of attaching the cap 570 to the center disc 504 are not germane to the present disclosure and one of skill in the art can quickly think of several viable alternatives. The upper side of the cap 570 is bonded to the lower side of the dual-use drape 550 at bonding locations 578. The outer boundary of cap 570 is indicated at dashed line 568.

The lower side of the dual-use drape 550 may be the lower side of the basin layer 558 for a two-layer drape. The bonding locations 578 may be thermal bonds, adhesive bonds, ultrasonic welding or other bonding techniques known to those of skill in the art and appropriate for the chosen materials. Note the temperature for creating thermal bonds between two layers of polyurethane drape such as basin layer 558 and upper layer 554 is likely to be different than a suitable temperature for creating thermal bonds between basin layer 558 and cap 570 as the cap 570 may be made from polycarbonate.

For the dual-use drape 550, the upper layer 554 may be 5 mil polyurethane and the smaller bottom layer 454 and basin layer 558 may be 2 mil polyurethane to provide additional protection against breach of the dual-use drape 550 within the basins 402 and 508.

As an alternative, the dual-use drape may be created without a second layer over the slush basin. The cap 570 would be bonded to the upper layer 554 at bonding locations 578. The dual-use drape 550 may be created using a thermal formed rectangular basin portion 710 as discussed below.

Perimeter Frame.

Figure 49:
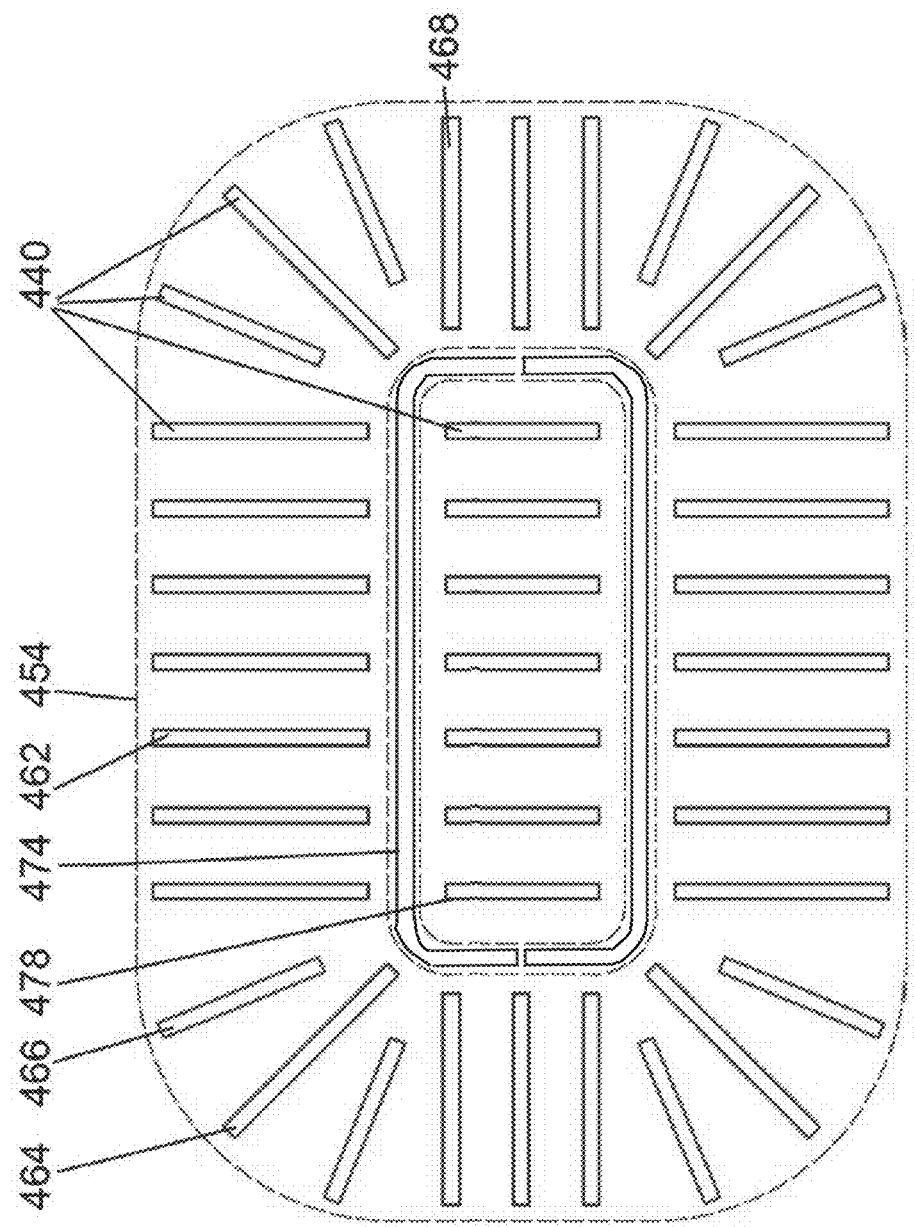
FIG. 49 provides an illustration of a rectangular perimeter frame 1470 with gaps 1472 and 1474 so that rectangular perimeter frame 1470 has piece 1476 and piece 1478.

The perimeter frame 320 may be made of one piece as shown in this disclosure. Those of skill in the art will recognize that the perimeter frame 320 could alternatively be made of a set of two or more pieces with small gaps in the perimeter. Having two or more pieces to be formed, placed, and enveloped with bonds between drape layers or bonded to a single layer drape may add processing steps but would otherwise provide the benefits set forth in this disclosure. FIG. 49 provides an illustration of a rectangular perimeter frame 1470 with gaps 1472 and 1474 so that rectangular perimeter frame 1470 has piece 1476 and piece 1478.

Non-Perimeter Positioning Devices.

While a useful way to align and maintain the position of the drape relative to the basin bottom is a perimeter frame as discussed above, other positioning devices could be employed by one of skill in the art. For example, a reticle (also known as crosshair) made of the same type of materials discussed in connection with the perimeter frame could be used to position the drape within the basin if the reticle was sized so that the radially distal portions of the reticle would only fit within the basin bottom if the center of the reticle was in the desired center location of the basin.

If the non-perimeter positioning device is over a portion of the basin where a heating element is attached, heat input may need to be limited to avoid overheating of the drape because the frame may inhibit heat transfer to the fluid. Otherwise, care may need to be taken to choose locations for the reticle or other non-perimeter positioning devices to avoid placement above any heating element or temperature sensors. Alternatively, the layout of the heating devices and temperature sensors may be selected based upon knowledge of the shape and orientation for the reticle or other non-perimeter positioning devices. An alignment marker may be helpful on fluid heating devices 200 that use a round basin 202 so that the reticle or other non-perimeter positioning devices are placed in a predictable way relative to the alignment marker.

Use of a non-perimeter positioning device such as a reticle that is highly conductive such as a metallic non-perimeter positioning device will allow a non-perimeter positioning device to be placed directly over a heating element as the highly conductive non-perimeter positioning device would distribute heat without the formation of a severe hot spot.

Figure 24:
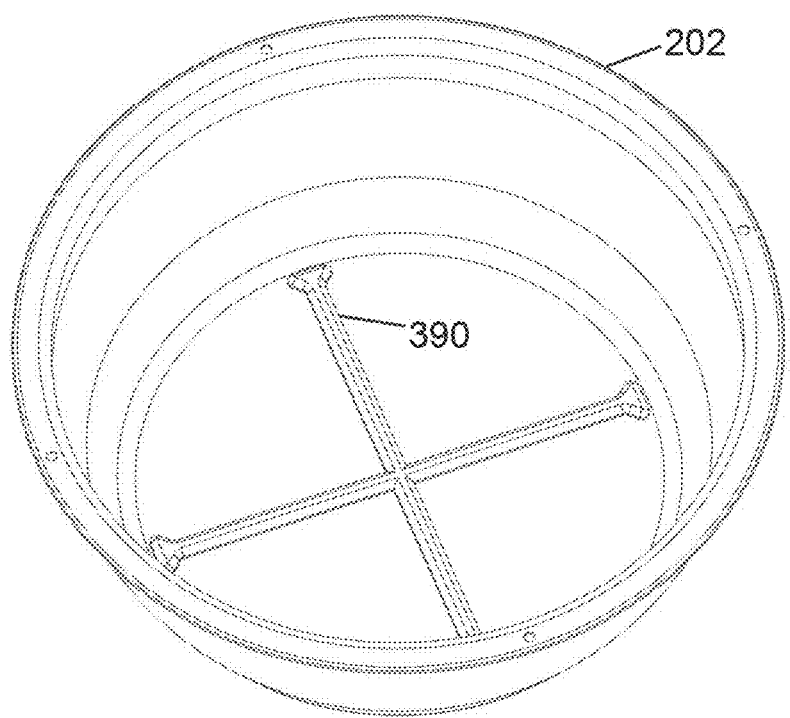
FIG. 24 shows top perspective view of a basin 202 and a round basin reticle 390 that would be placed in a drape 300 to use as a non-perimeter positioning device to help position the drape 300 within the basin 202.

FIG. 24 shows top perspective view of a basin 202 and a round basin reticle 390 that would be placed in a drape 300 to use as a non-perimeter positioning device to help position the drape 300 within the basin 202.

Figure 25:
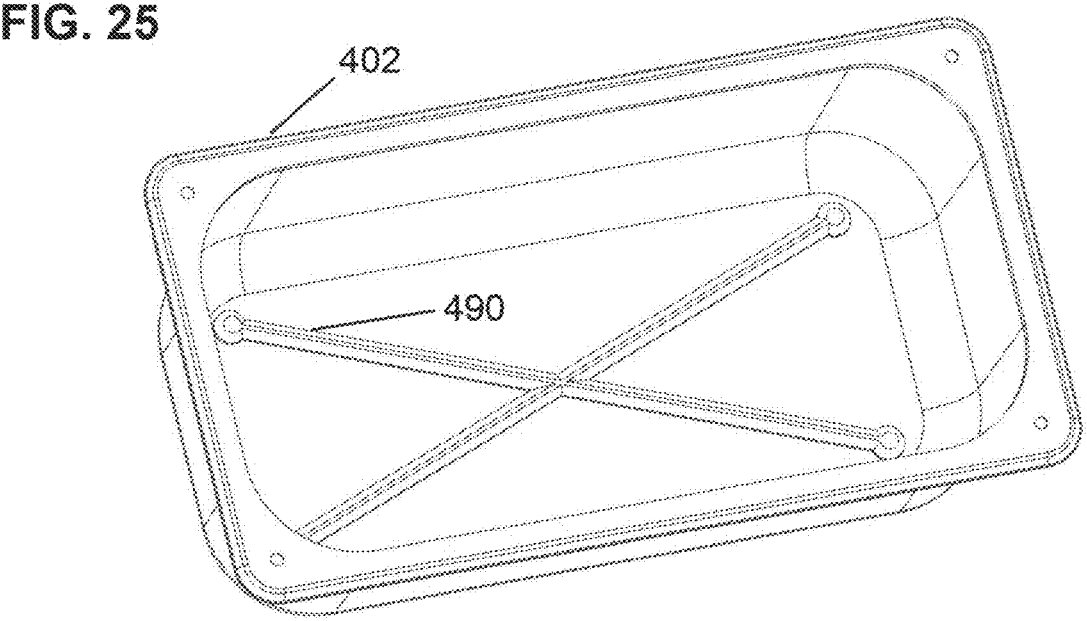
FIG. 25 shows a top perspective view of a rectangular basin 402 with a rectangular basin reticle 490 that would be placed in a drape 450 to use as a non-perimeter positioning device to help position the drape 450 within the rectangular basin 402.

FIG. 25 shows a top perspective view of a rectangular basin 402 with a rectangular basin reticle 490 that would be placed in a drape 450 to use as a non-perimeter positioning device to help position the drape 450 within the rectangular basin 402.

Reticles are but one well-known pattern that could be used to position the drape. An asterisk, star, pound sign ("#"), or tic tac toe lattice could be used. For a rectangular shaped basin bottom, the shape could be a series of parallel bars running parallel to the long sides of the rectangle or running parallel to the short sides of the rectangle. The choices are unlimited although some choices may be easier to implement, especially with respect to avoiding covering the heating elements or heat sensors.

Sterilization.

The drapes made in accordance with the teachings of the present disclosure are to be delivered to the end user in a sterilized condition. Those of skill in the art will recognize that there are various options for sterilizing items of this sort, including the use of ethylene oxide. It is expected that the drapes will be single use items.

Basin Shape Impressed into Drape.

Figure 26:
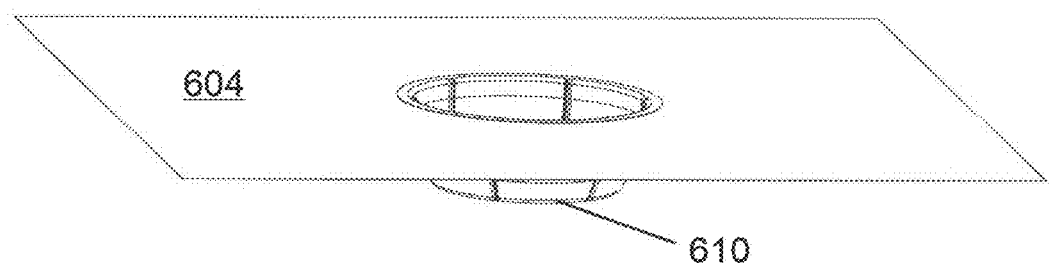
FIG. 26 shows an alternative drape 600 for use in round basin 202 instead of drape 300 discussed above.

FIG. 26 shows an alternative drape 600 for use in round basin 202 instead of drape 300 discussed above. Drape 600 has a flat portion 604 and a round basin portion 610 that is thermal formed. The round basin portion 610 forms a sterile vented barrier for use in covering the basin. Both the flat portion 604 and the round basin portion 610 may be made of polyurethane. Those of skill in the art will appreciate that the thickness of the drape material needs to be sufficient to allow the thermal forming of the round basin portion 610.

Figure 27:
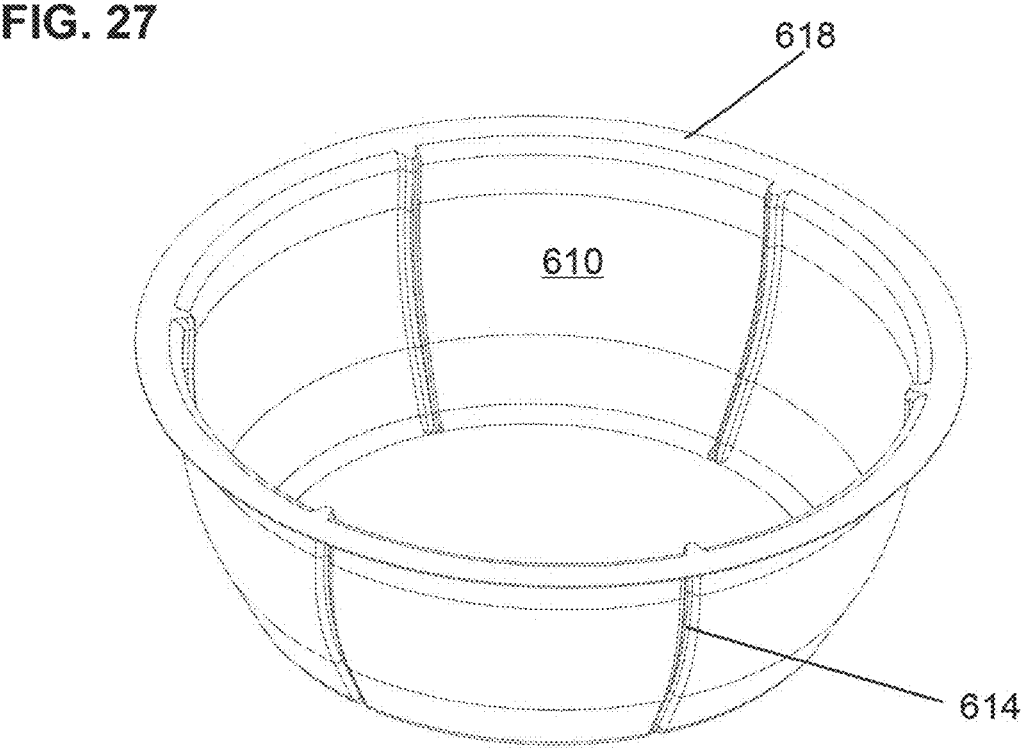
FIG. 27 shows a top perspective view of just the round basin portion 610 from FIG. 26.

FIG. 27 shows a top perspective view of just the round basin portion 610. In FIG. 27 the basin vents 614 are visible. These basin vents 614 allow air to flow up from the basin 202 to above the top surface 252 of the fluid heating device 200 (See FIG. 7) when the round basin portion 610 is pressed down into a round basin 202.

The round basin portion 610 may be top loaded into an appropriately sized opening in flat portion 604 with the flange 618 resting on the top of the flat portion 604. The flange 618 may be attached to flat portion 604 by heat seals or other appropriate methods. As the basin vents 614 are open to the outside of the round basin portion 610, air will be vented up the side of the basin 202 as the round basin portion 610 is put into position and this air will vent under flat portion 604 of drape 600.

FIG. 30 through FIG. 40 provide additional views of the round basin portion 610 of drape 600. Element 610 may alternatively be called a sterile vented barrier for use in a round basin.

Figure 28:
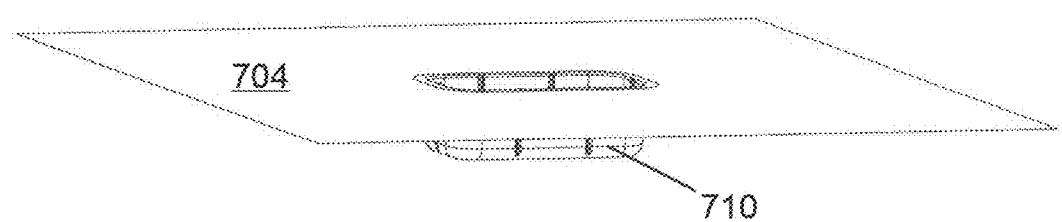
FIG. 28 shows an alternative drape 700 for use in rectangular basin 402 instead of drape 450 discussed above.

FIG. 28 shows an alternative drape 700 for use in rectangular basin 402 instead of drape 450 discussed above. Drape 700 has a flat portion 704 and a rectangular basin portion 710 that is thermal formed. The rectangular basin portion 710 forms a sterile vented barrier for use in covering the basin. Both the flat portion 704 and the rectangular basin portion 710 may be made of polyurethane. Those of skill in the art will appreciate that the thickness of the drape material needs to be sufficient to allow the thermal forming of the rectangular basin portion 710.

As there will be significant thinning of material during the forming of the basin portion (whether round or rectangular) the initial starting thickness of the drape material may be 30 mils in order to ensure that the formed basin portion is at least 5 mil in the thinnest portion. Additional control over the forming process may allow for a thinner drape material to be used.

Figure 29:
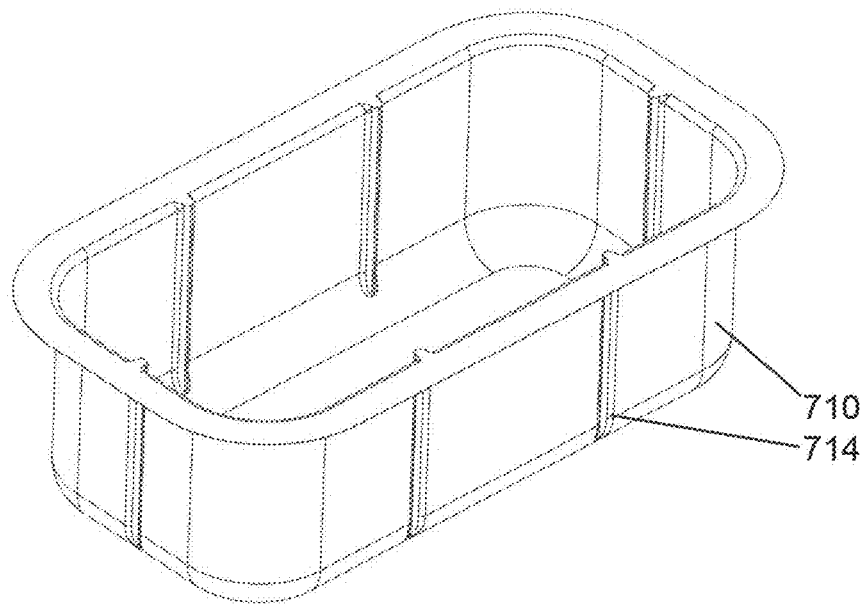
FIG. 29 shows a top perspective view of just the rectangular basin portion 710 seen in FIG. 28.
Figure 30:
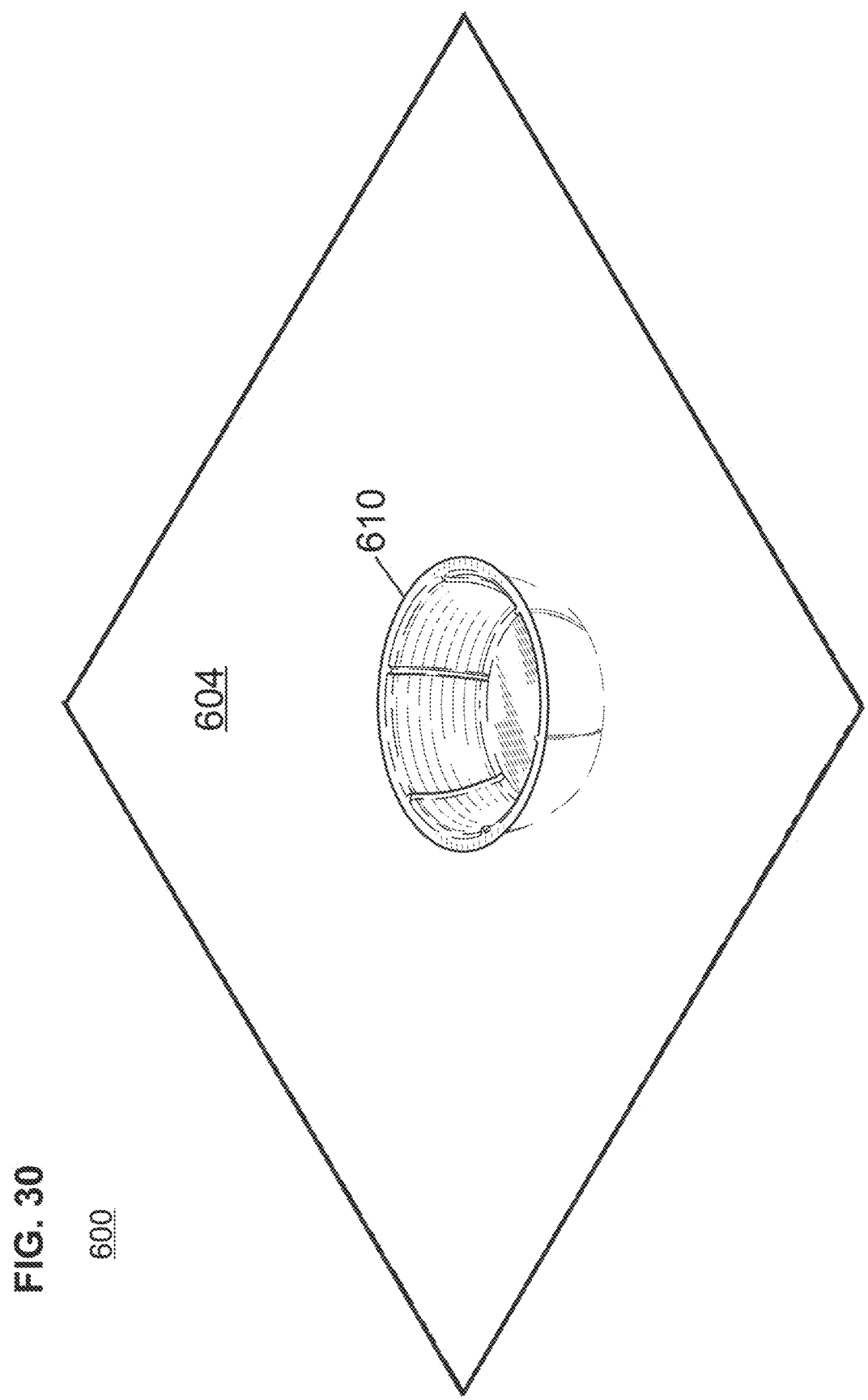
FIG. 30 is a top perspective view of the round basin portion 610 of drape 600. Element 610 may be called a sterile vented barrier for use in a round basin.
Figure 31:
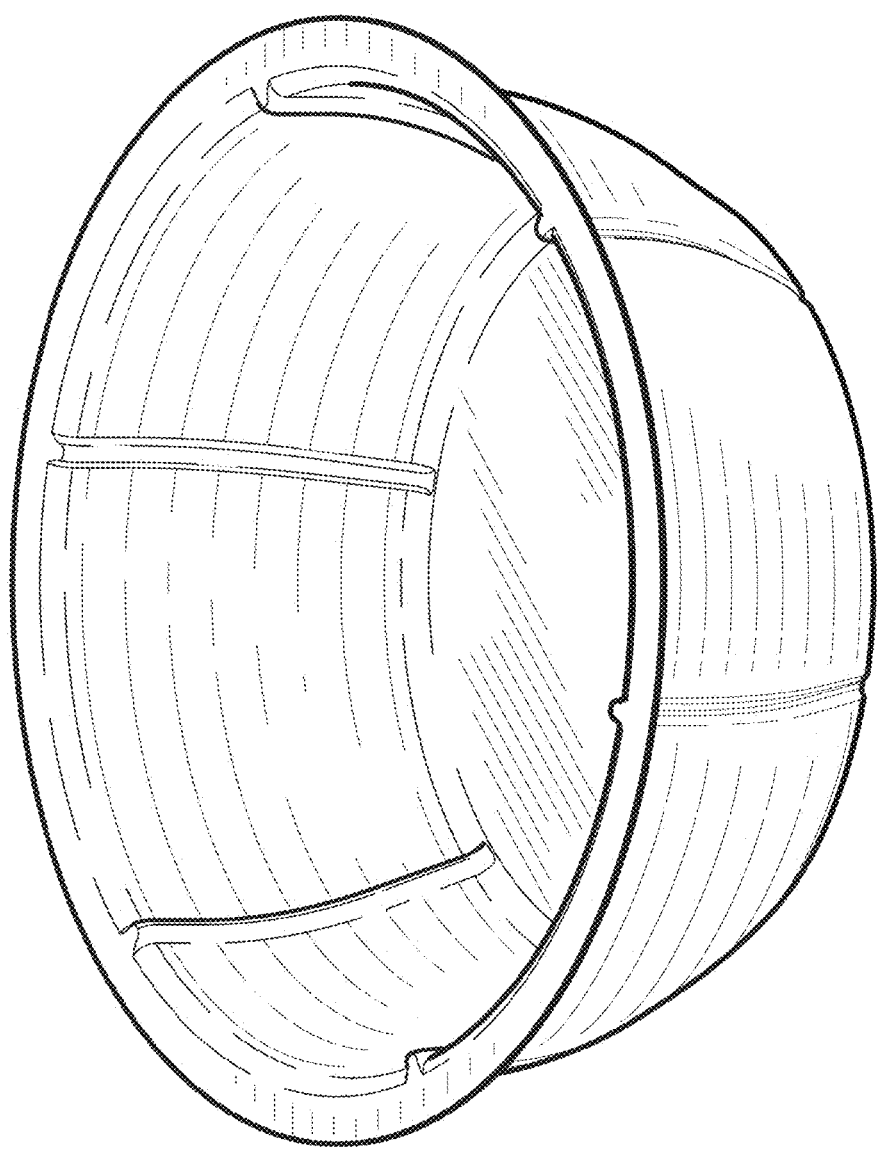
FIG. 31 is an enlarged view of the round basin portion 610 shown in FIG. 30.
Figure 32:
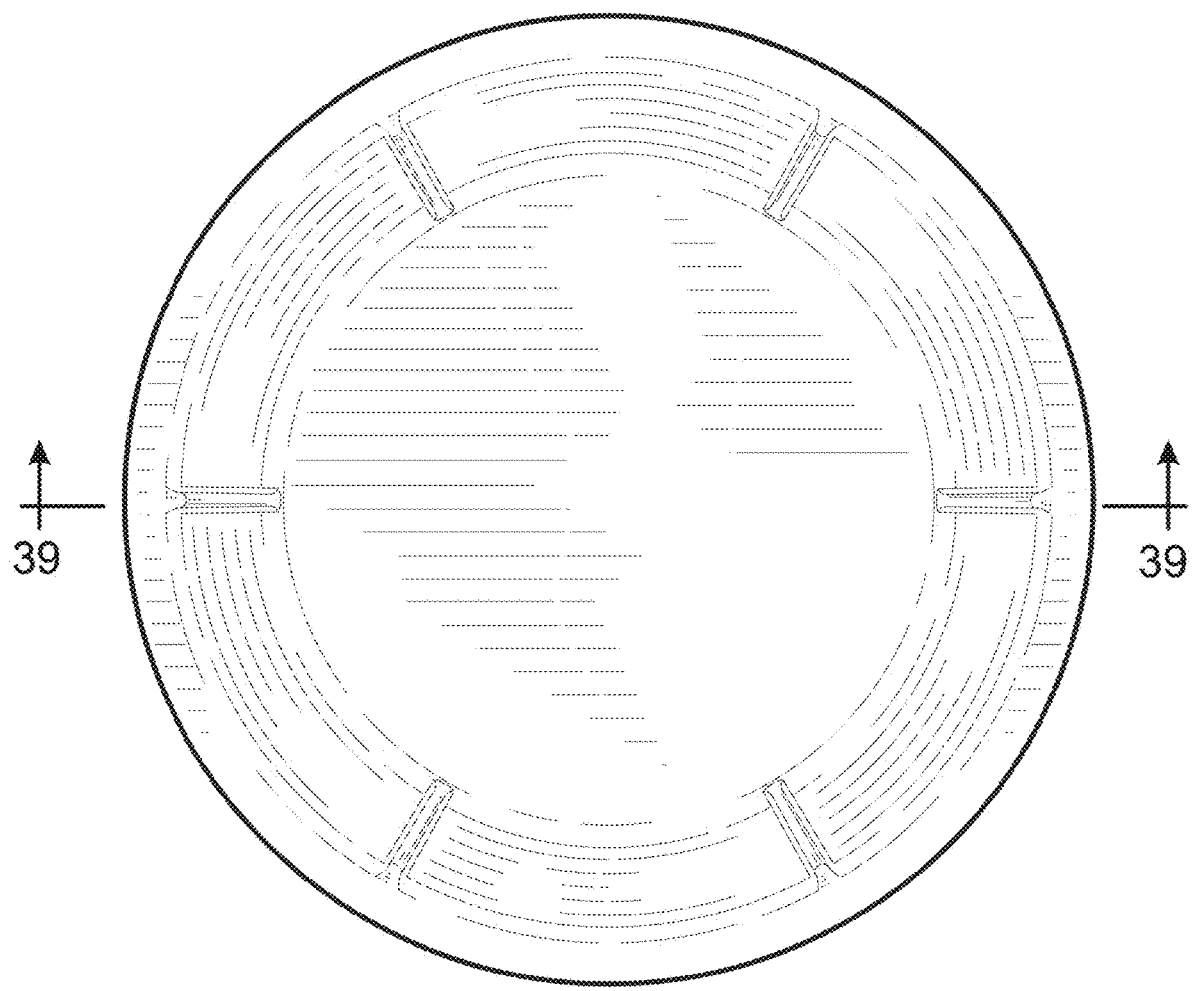
FIG. 32 is a top plan view of the round basin portion 610.
Figure 33:
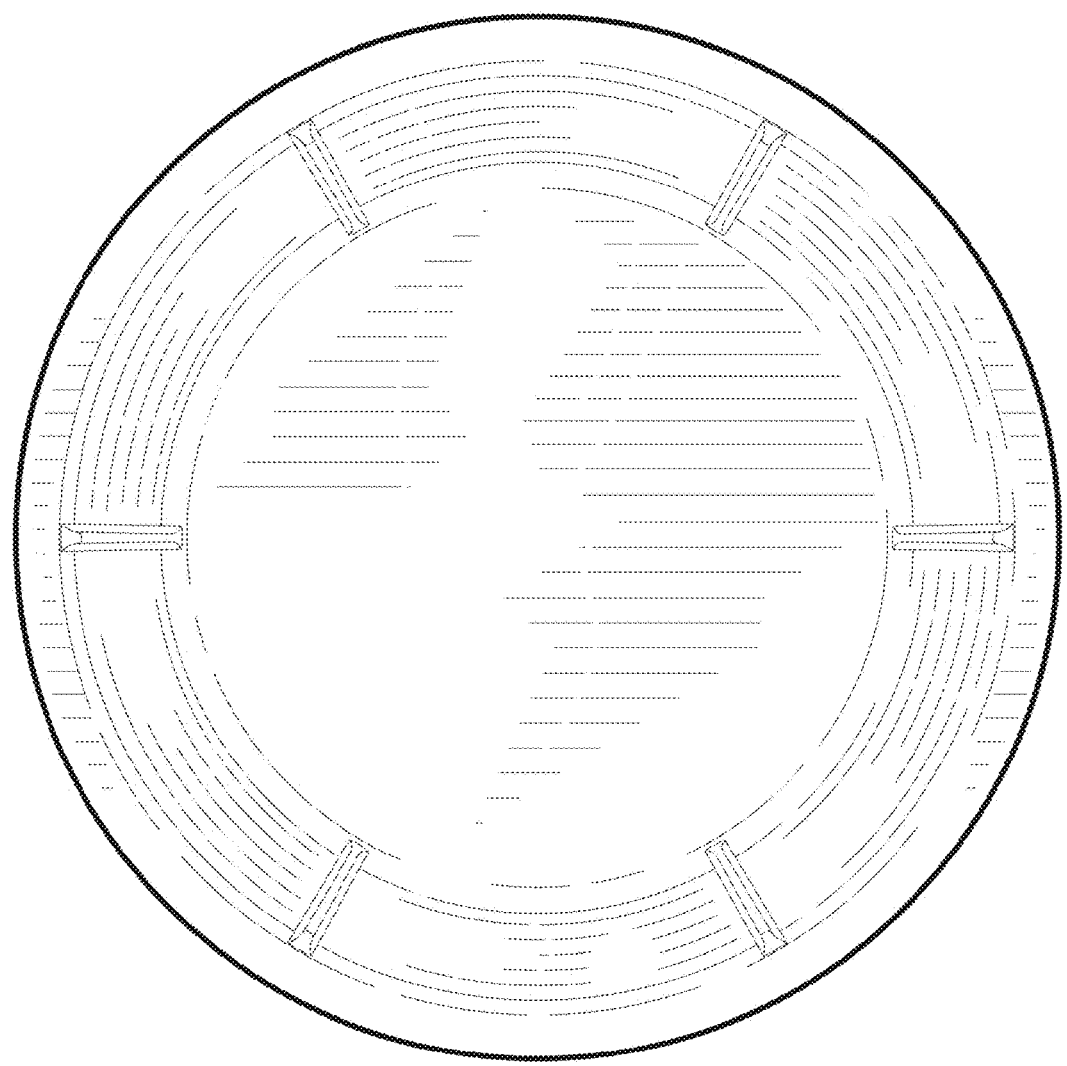
FIG. 33 is a bottom plan view of the round basin portion 610.
Figure 34:
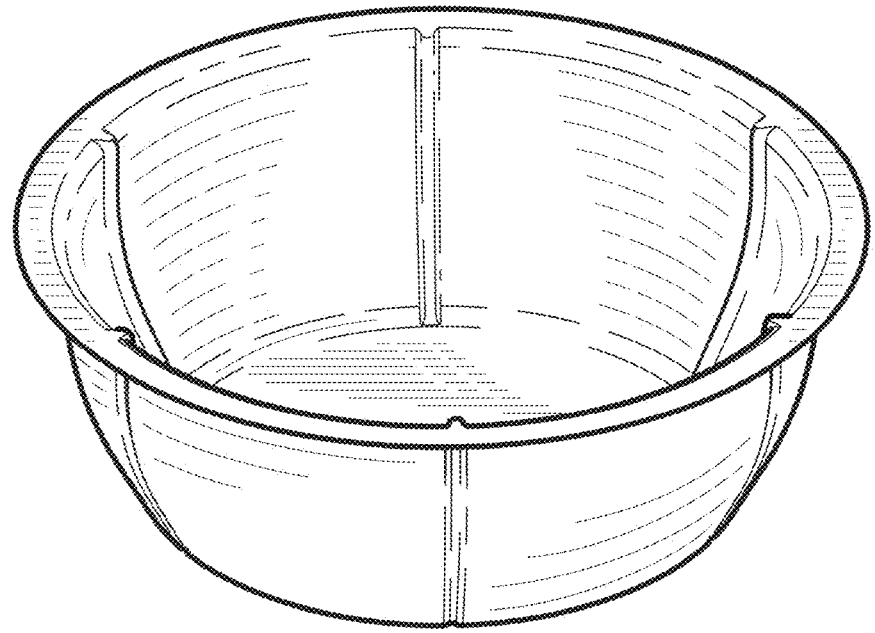
FIG. 34 is a top side perspective view perspective view of the round basin portion 610.
Figure 35:
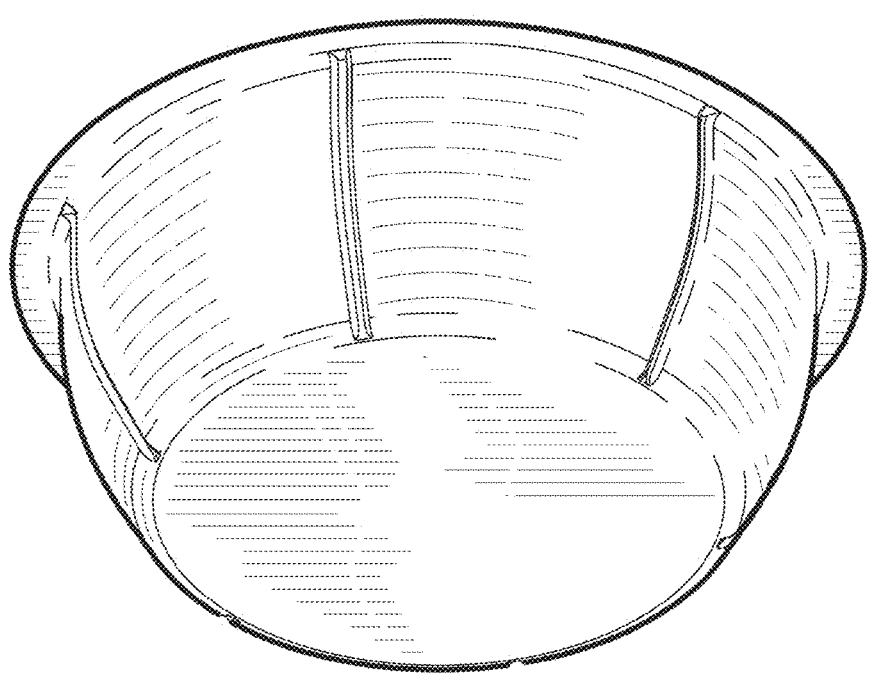
FIG. 35 is a bottom side perspective view perspective view of the round basin portion 610.
Figure 36:
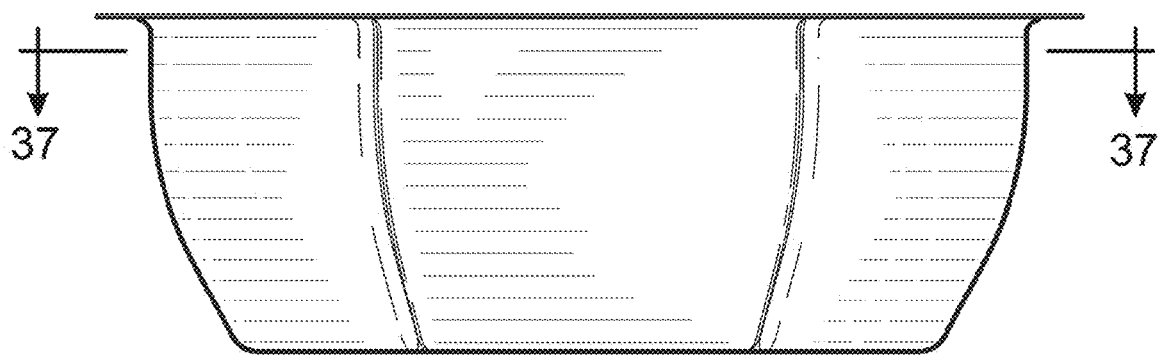
FIG. 36 is a side plan view of the round basin portion.
Figure 37:
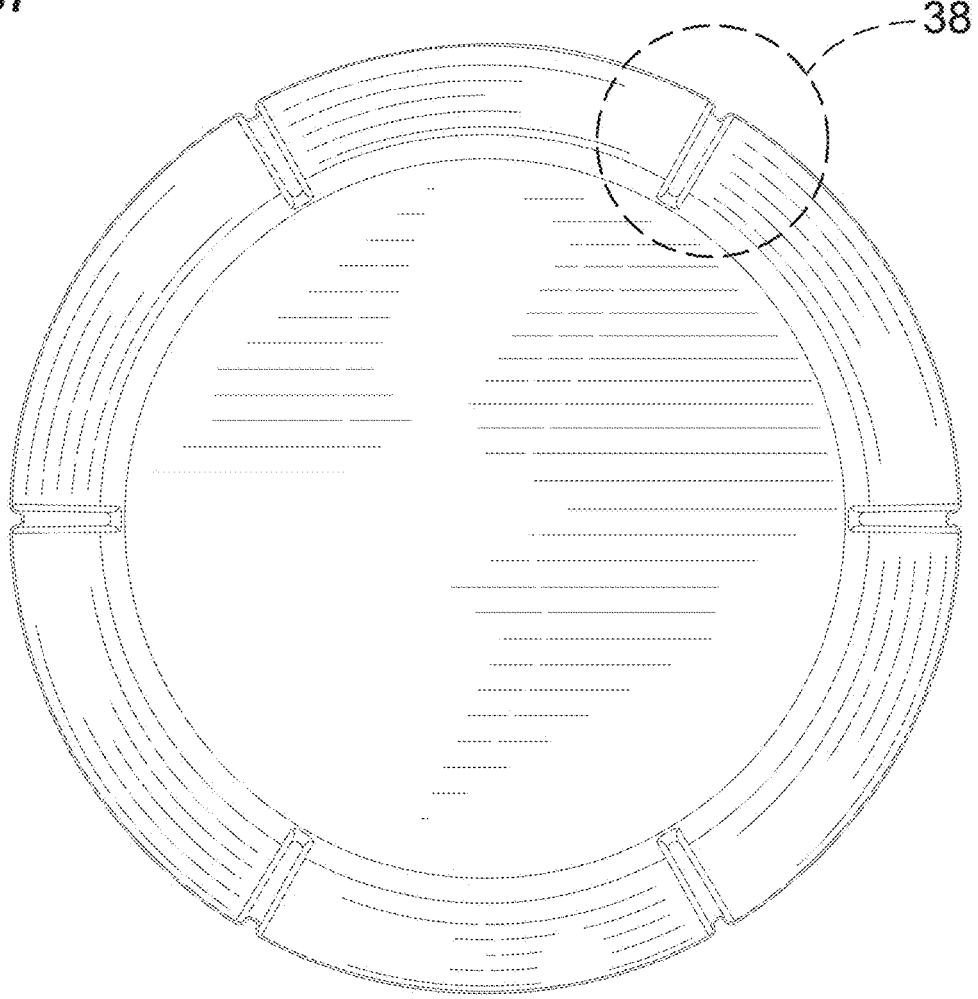
FIG. 37 is a downward view of the cross-section shown in FIG. 36 taken below the rim.
Figure 38:
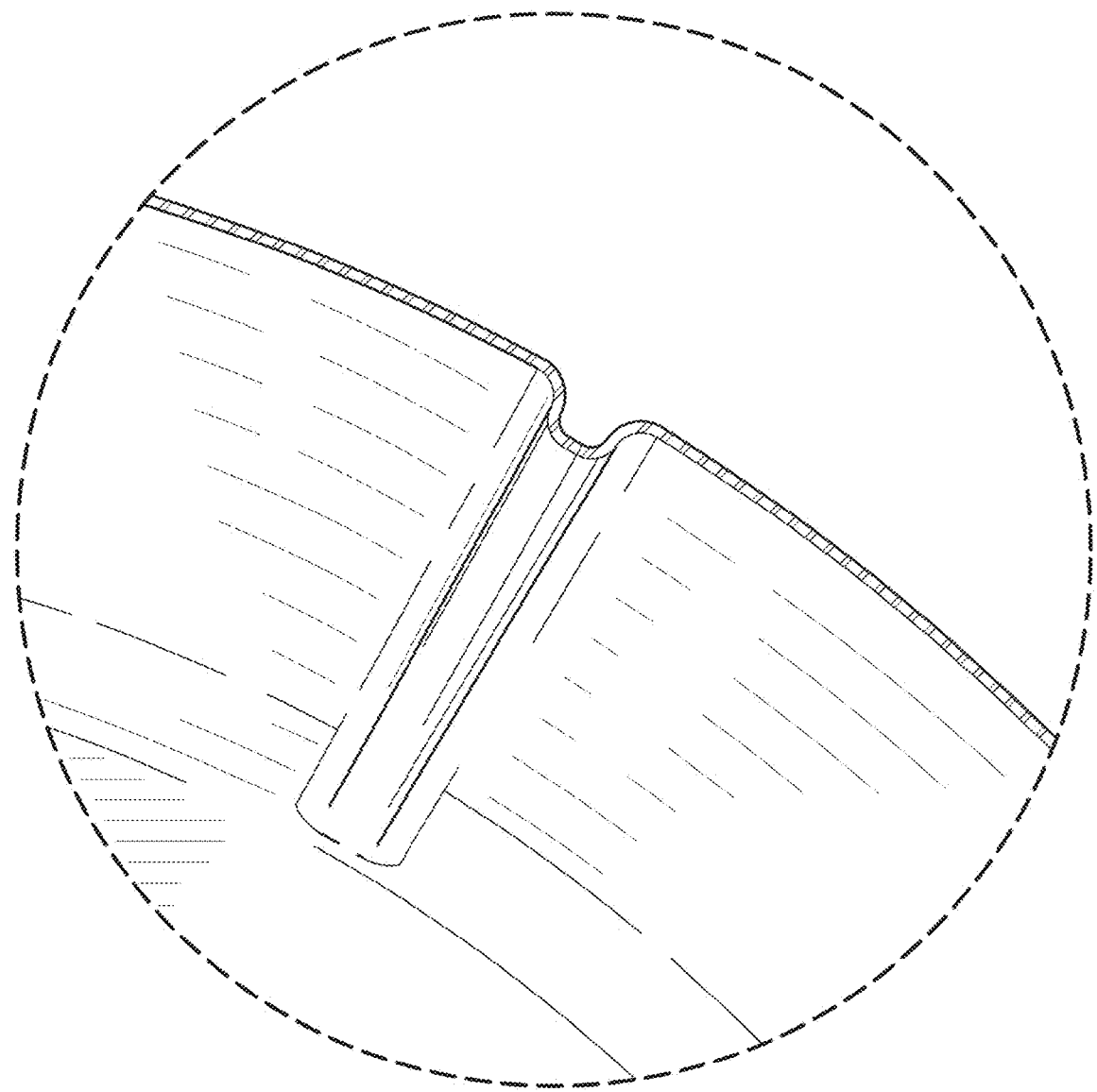
FIG. 38 is an enlarged section from FIG. 37 showing the shape of a vent.
Figure 39:
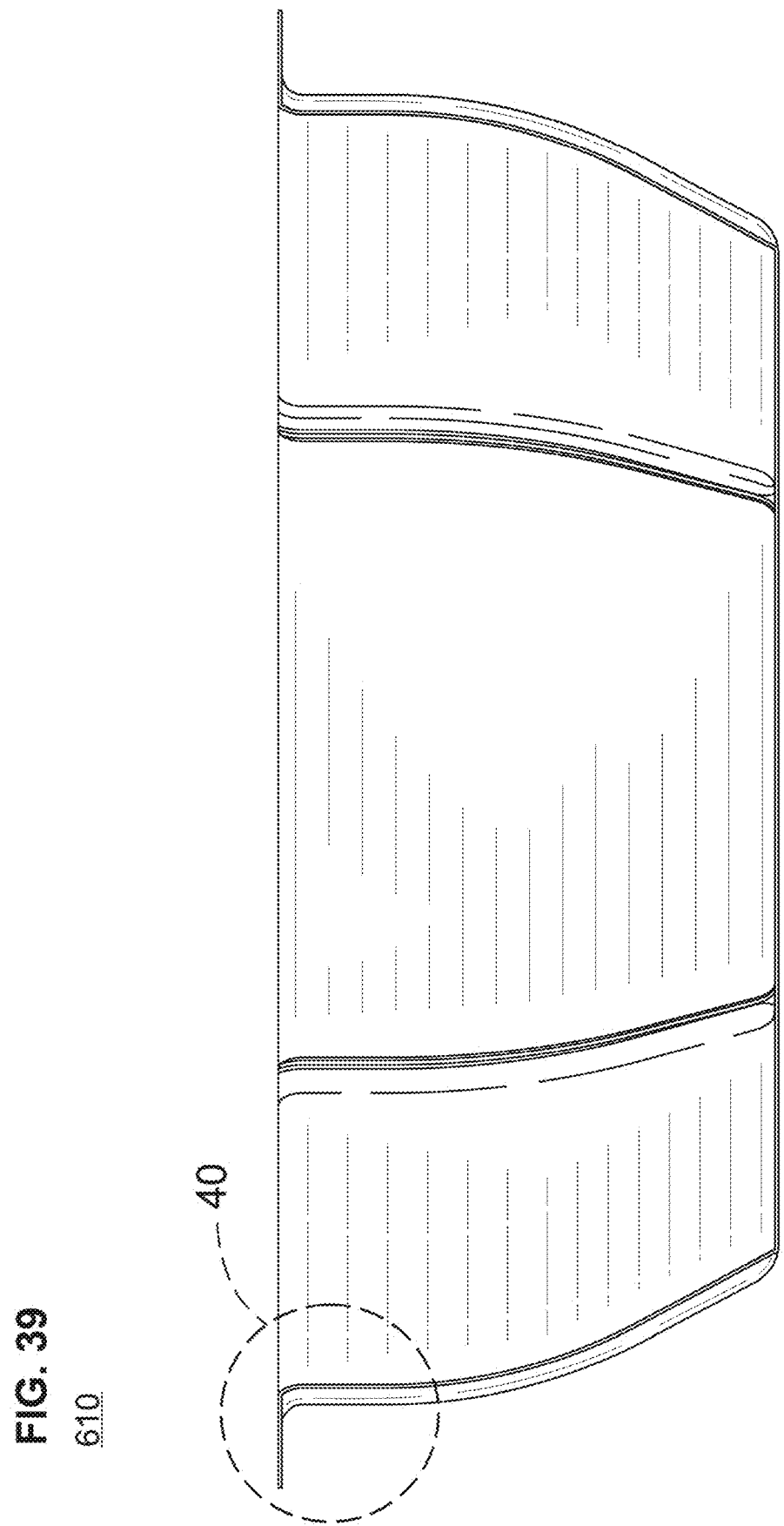
FIG. 39 is a side view of a cross-section indicated on FIG. 32.
Figure 40:
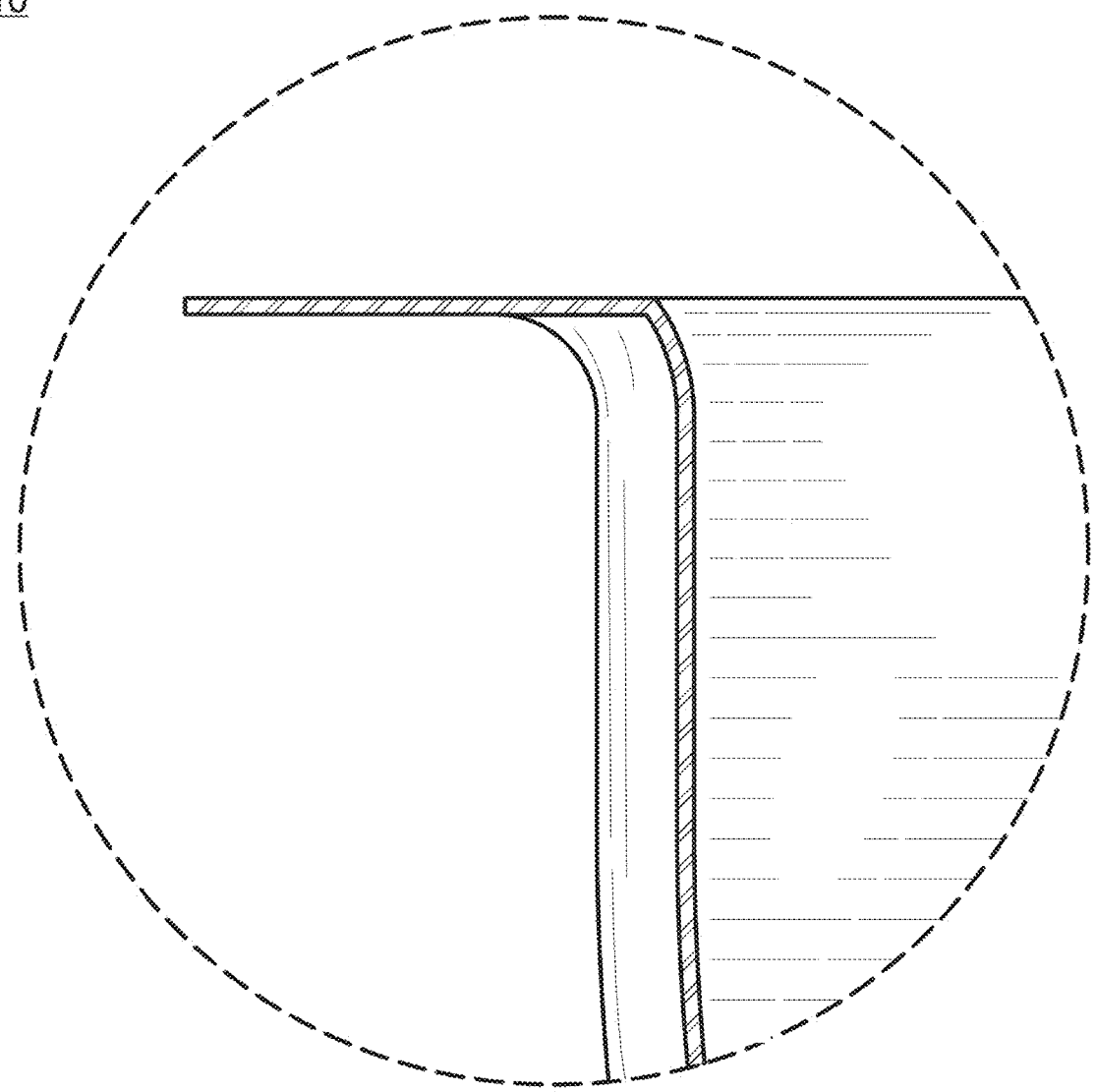
FIG. 40 in an enlarged portion of FIG. 39 showing a cross section of a vent.
Figure 41:
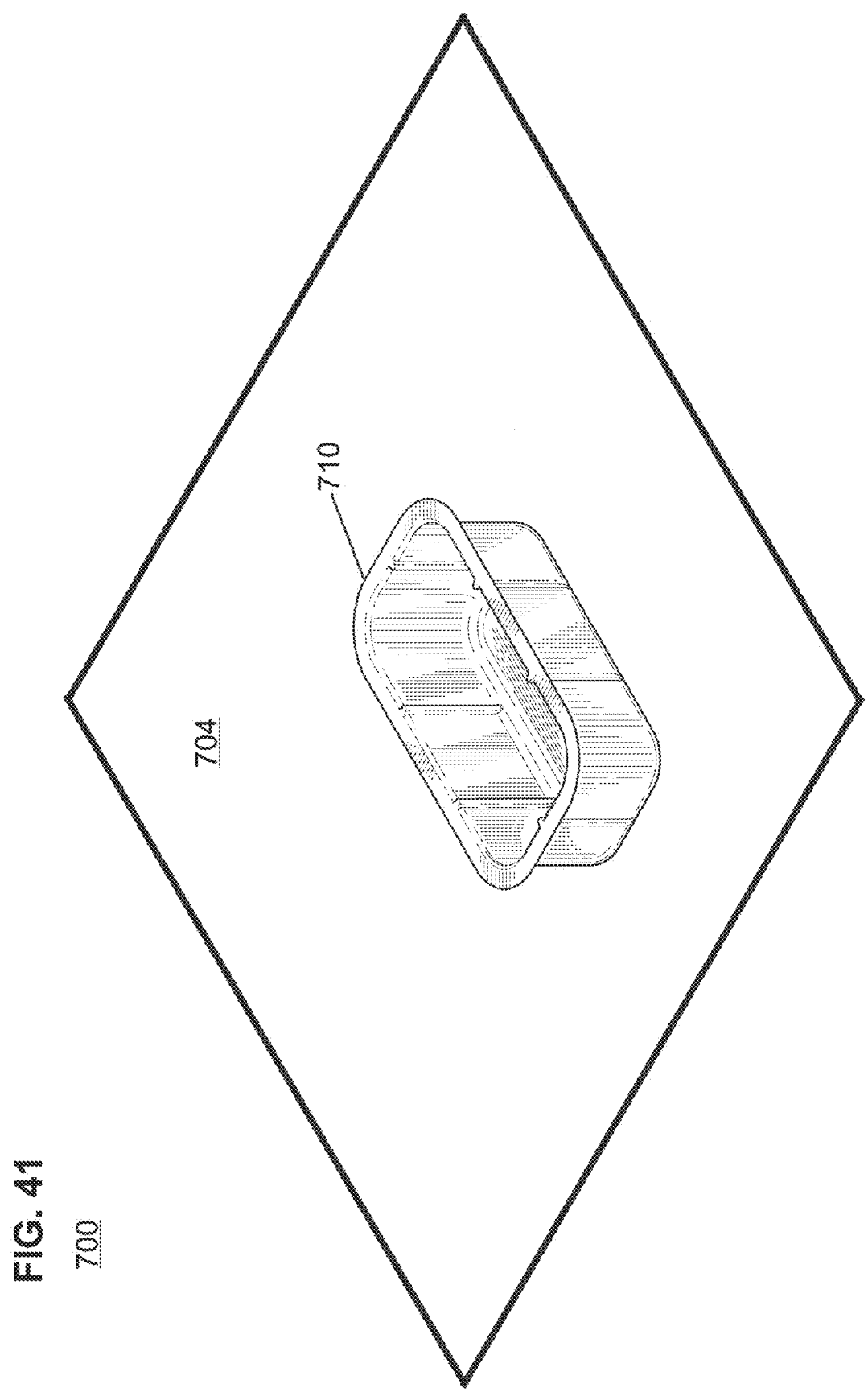
FIG. 41 is a top perspective view of the rectangular basin portion 710 of drape 700. Element 710 may be called a sterile vented barrier for use in a rectangular basin.
Figure 42:
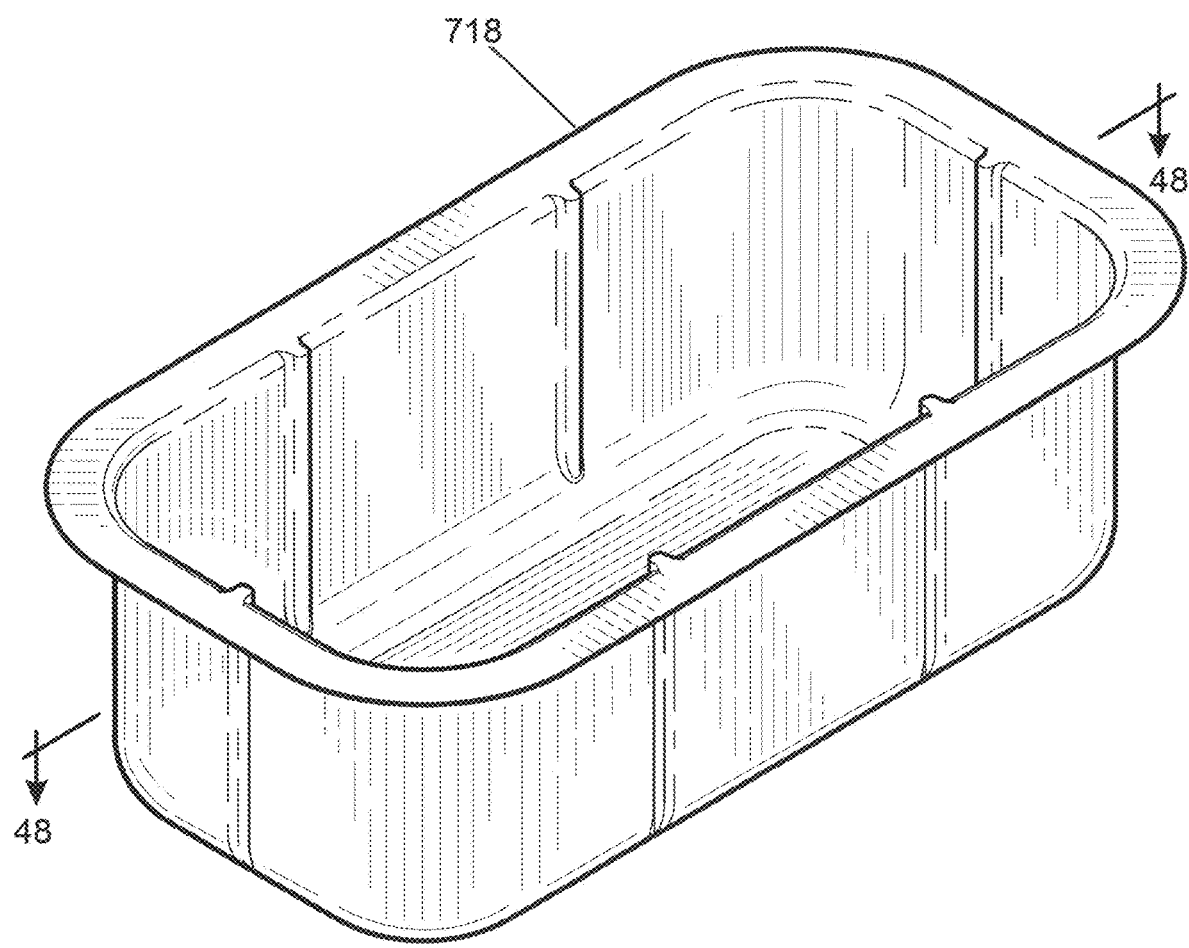
FIG. 42 is an enlarged view of the rectangular basin portion 710 from FIG. 41.
Figure 43:
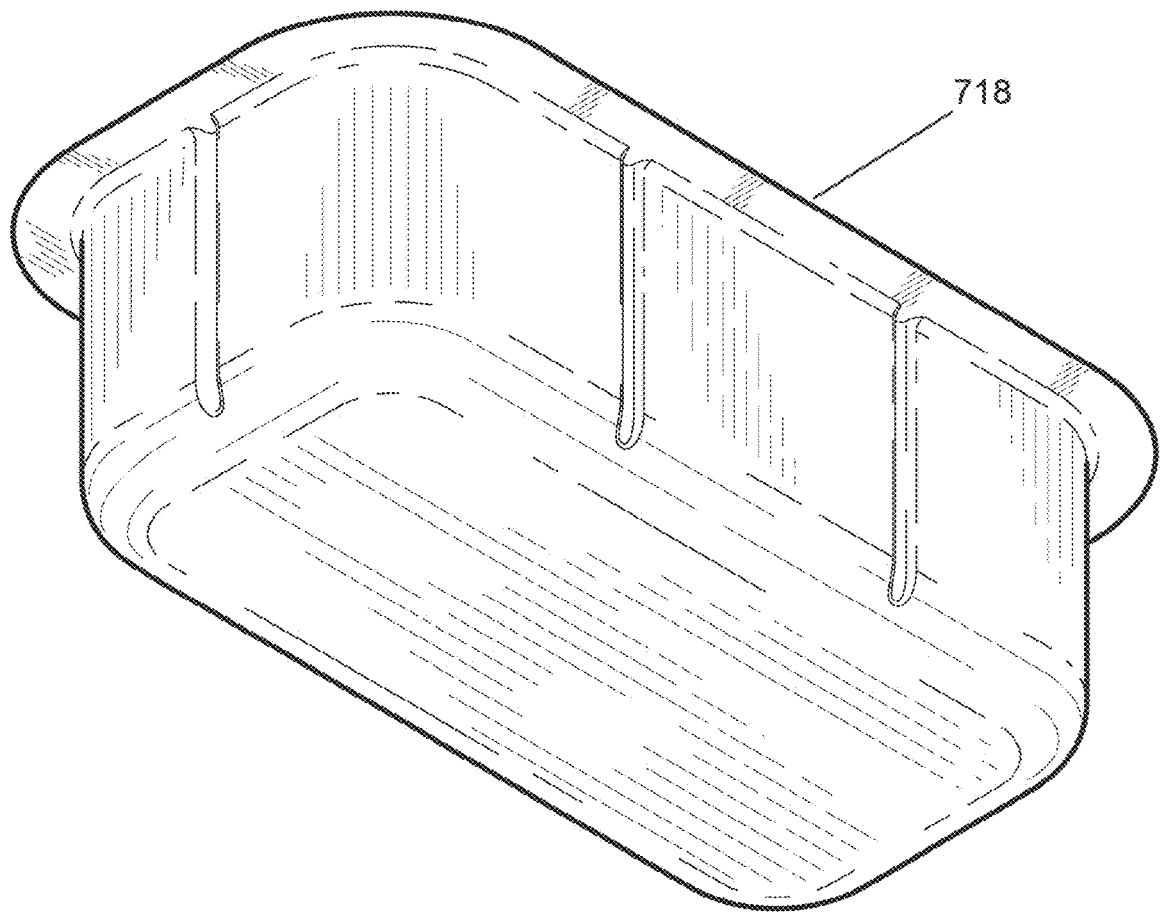
FIG. 43 is a bottom side perspective view of the rectangular basin portion 710.
Figure 44:
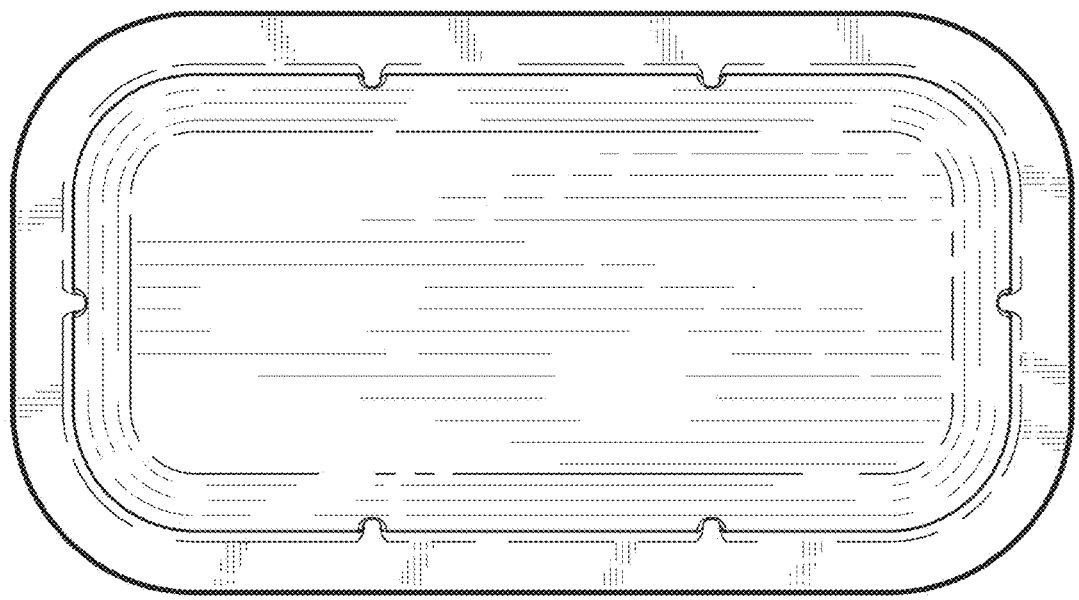
FIG. 44 is a top plan view of the rectangular basin portion 710.
Figure 45:
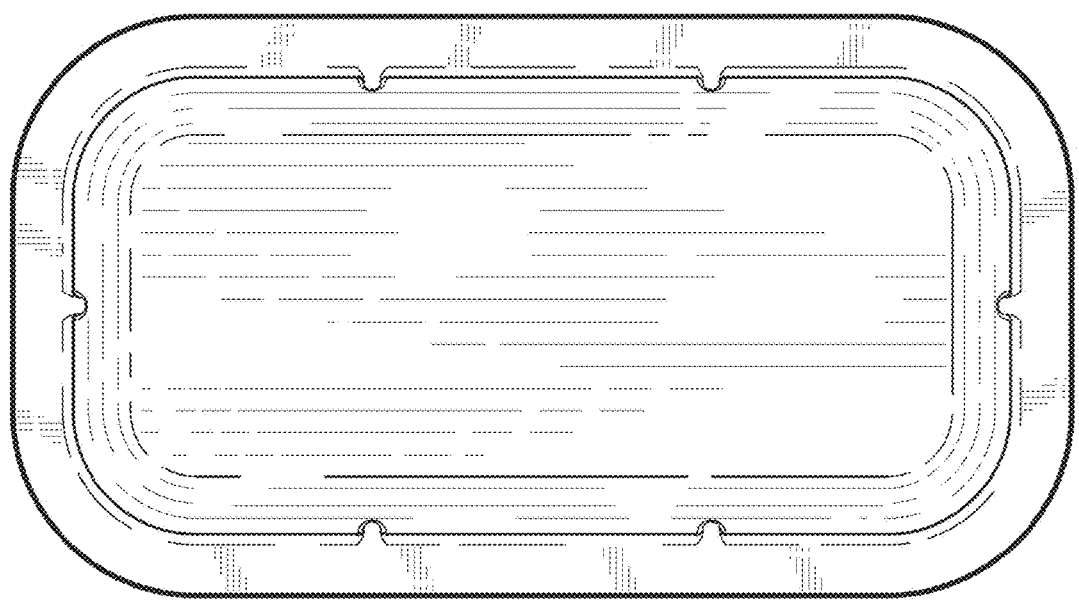
FIG. 45 is a bottom plan view of the rectangular basin portion 710.
Figure 46:
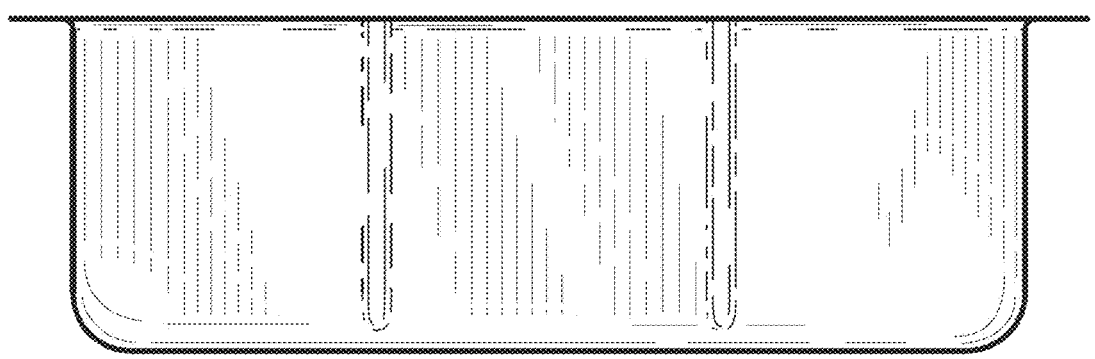
FIG. 46 is a right side elevation view of the rectangular basin portion 710. The left side elevation view being the same as this side elevation view.
Figure 47:
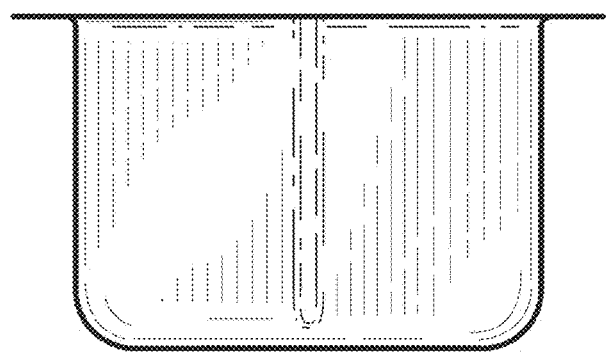
FIG. 47 is a front elevation view of the rectangular basin portion 710. The rear elevation view being the same as this front elevation view.
Figure 48:
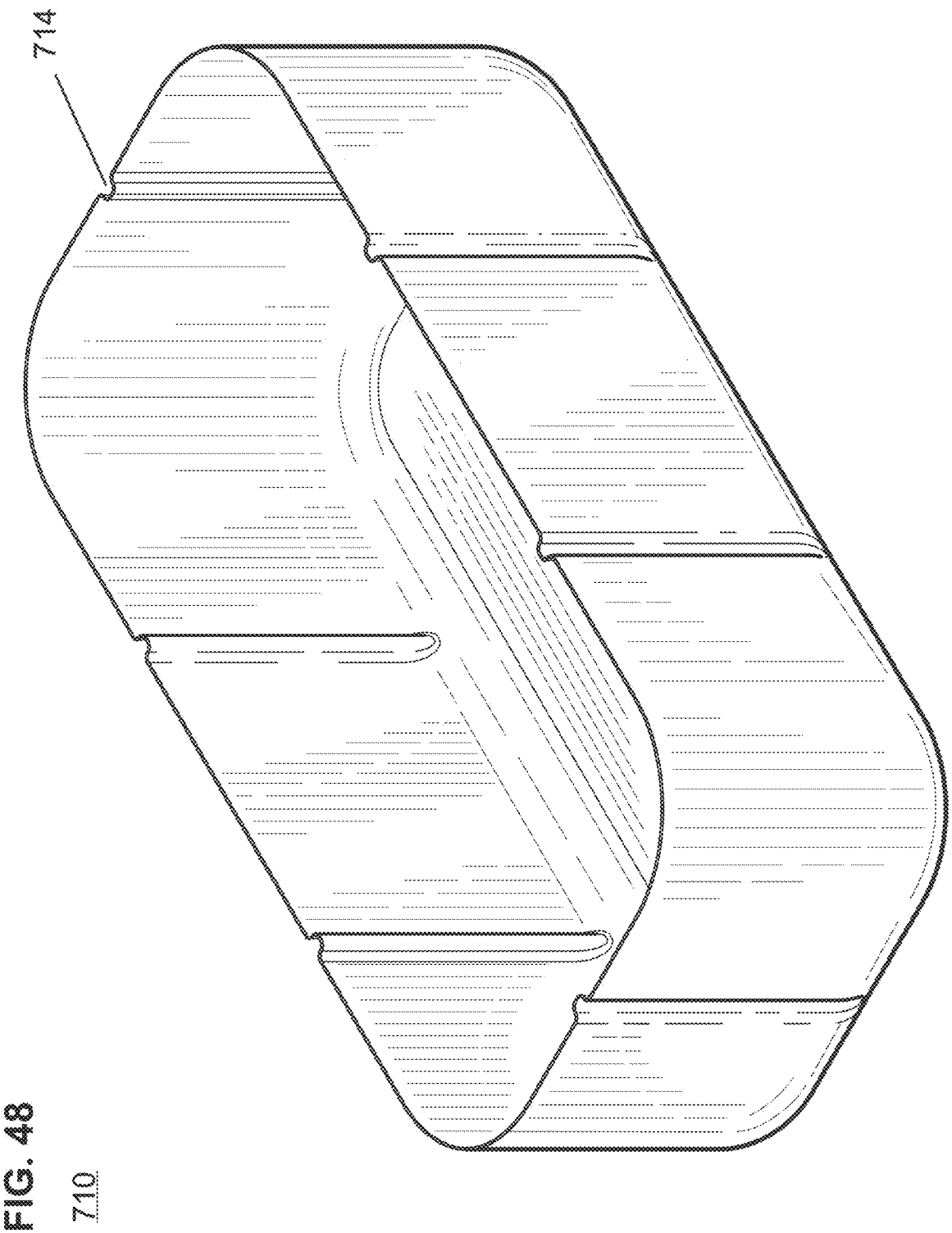
FIG. 48 shows the same view as FIG. 42 but of a cross section taken below the flange 718 to show details of vents 714.

FIG. 29 shows a top perspective view of just the rectangular basin portion 710. The rectangular basin portion 710 may be top loaded into an appropriately sized hold in flat portion 704 with the flange 718 resting on the flat portion 704. The flange 718 may be connected to flat portion 704 by heat seals or other appropriate methods.

In FIG. 29 the rectangular basin vents 714 are visible. These rectangular basin vents 714 allow air to flow up from the rectangular basin 402 to above the top portion 410 of the fluid heating device 400 (See FIG. 18) and below the flat portion 704 of the drape 700 when the rectangular basin portion 710 is pressed down into a rectangular basin 402.

FIG. 41 through FIG. 48 provide additional views of the rectangular basin portion 710 of drape 700. Element 710 may alternatively be called a sterile vented barrier for use in a rectangular basin.

Monitoring In Proximity to the Air Gap Detector.

The application as originally filed noted—The first air gap detector monitoring heat on a portion of the underside of the basin in proximity to the first air gap detector. The first air gap detector responding to a temperature above a first high setpoint temperature by interrupting the flow of electricity sent to the first heating element. The first air gap detector continuing the interruption of the flow of electricity sent to the first heating element until detecting a temperature below a first reset setpoint temperature which is less than the first high setpoint temperature.

This level of abstraction was accurate. Thus while the original application had a focus on air gaps above the air gap detector and below the drape, the system would actually respond to air gaps in proximity to the air gap detector including air gaps formed above the drape even if the air gap was not directly above the air gap detector. While it may seem counter-intuitive for an air gap to form above the drape, this is a common occurrence when a pitcher or other object with a perimeter rim and an inner raised portion is placed upon a drape covering a heating element. An air gap can form within an enclosed perimeter above the drape. As with other air gaps, this air gap above the drape is more of an insulator than a conductor and blocks the transfer of heat. Thus, the air gap above the drape can cause a localized hotspot which might endanger the integrity of the drape.

Thus, when fully appreciated, an air gap detector can detect a hotspot caused by an air gap above or proximal to the air gap detector. Further, an air gap detector detects an impingement on heat transfer from both air gaps below the drape or air gaps above the drape.

Continuation-in-Part Material.

In order to enhance the ability of the application to convey the inventive concepts and the value of an additional component, a series of figures and some additional text augments the prior application material.

Figure 50:
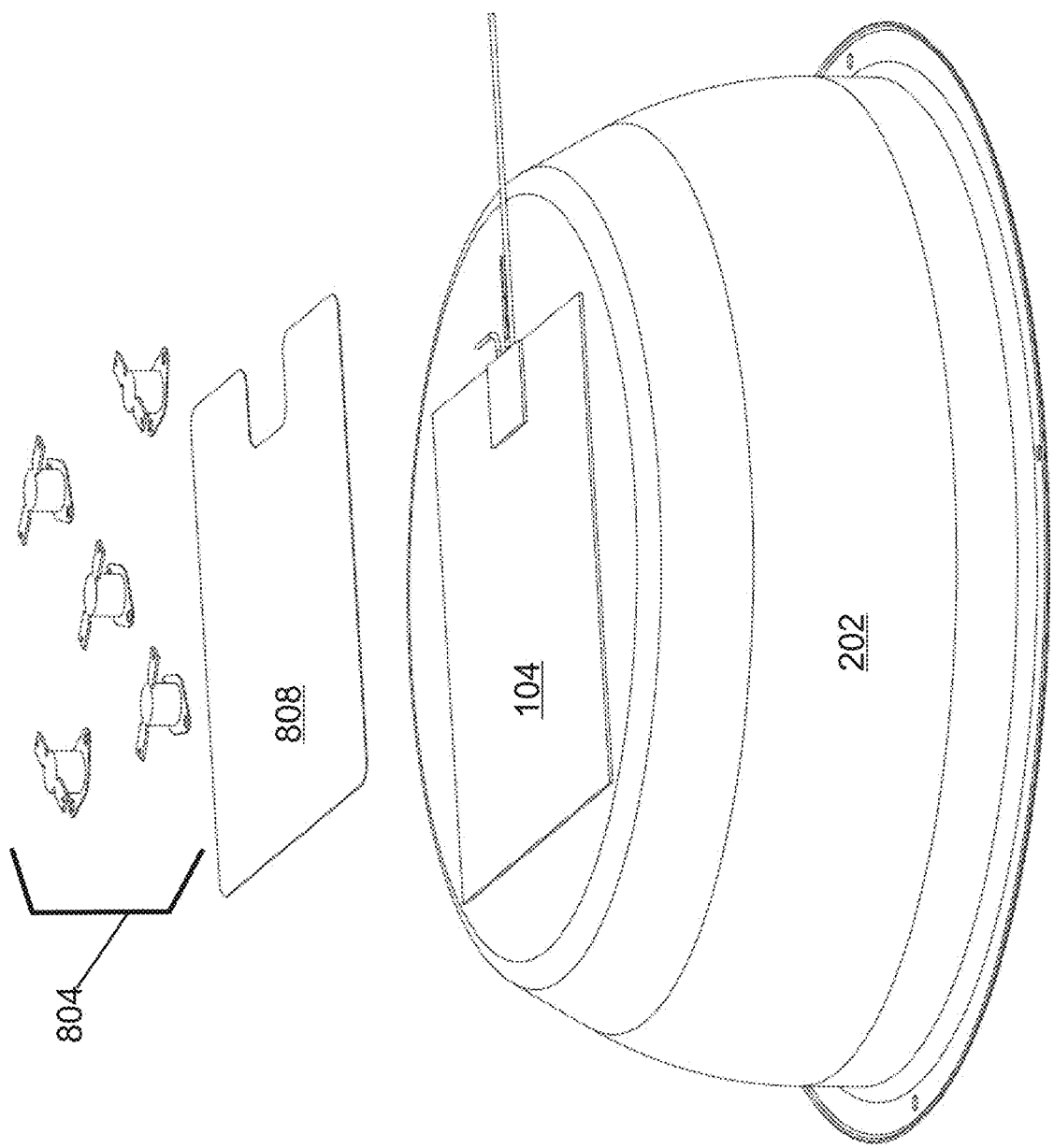
FIG. 50 shows a bottom perspective view of basin 202 with various components in an exploded view to facilitate discussion.

FIG. 50 is much like FIG. 15 discussed above. FIG. 50 shows a bottom perspective view of basin 202 with various components in an exploded view to facilitate discussion. In FIG. 50 there is a first arrangement of a set of air gap detectors 804 positioned below heating element 104. As discussed below, the set of air detectors are in series. If any of the air gap detectors within the set of air gap detectors 804 senses a temperature in excess of the interrupt setpoint, the air gap detector will open the circuit and stop the flow of energy to the heating element 104. Thus, the set of air gap detectors 804 provide redundancy to temperature sensor 108 but also interrupts power to the heating element in the event that the drape 300 (not shown here) is not positioned in a manner that avoids an air gap (such as 128 in FIG. 6). The use of the set of air gap detectors 804 provides a system that will periodically interrupt the flow of power to the heating element 104 so that the temperature of the basin 202 below the air gap will not rise to temperatures that are above the melting temperature for the drape 300.

A difference between FIG. 15 and FIG. 50 is the addition of heat dispersion plate 808 between the heating element 104 and the set of air gap detectors 804. One of skill in the art can select a suitable material for use in heat dispersion plate 808 that has sufficient thermal conductivity so that a each of the members of the set of air gap detectors 808 is able to discern air gaps above the heating element 104 that are somewhat distal from that air gap detector. In other words, the use of the heat dispersion plate 808 helps individual members of the set of air gap detectors 804 react more quickly to hot spots caused by air gaps when the hot spots are not directly above any of the set of air gap detectors 804. One of skill in the art can make the design choices for the number of air gap detectors and the thermal conductivity of the heat dispersion plate 808 to provide suitable air gap monitoring for a particular size and particular size basin. The example in FIG. 50 of five air gap detectors in the set of air gap detectors 804 for this round basin should be understood as illustrative and not limiting. The number of air gap detectors could be something other than five and the basin bottom does not need to be round.

Figure 51:
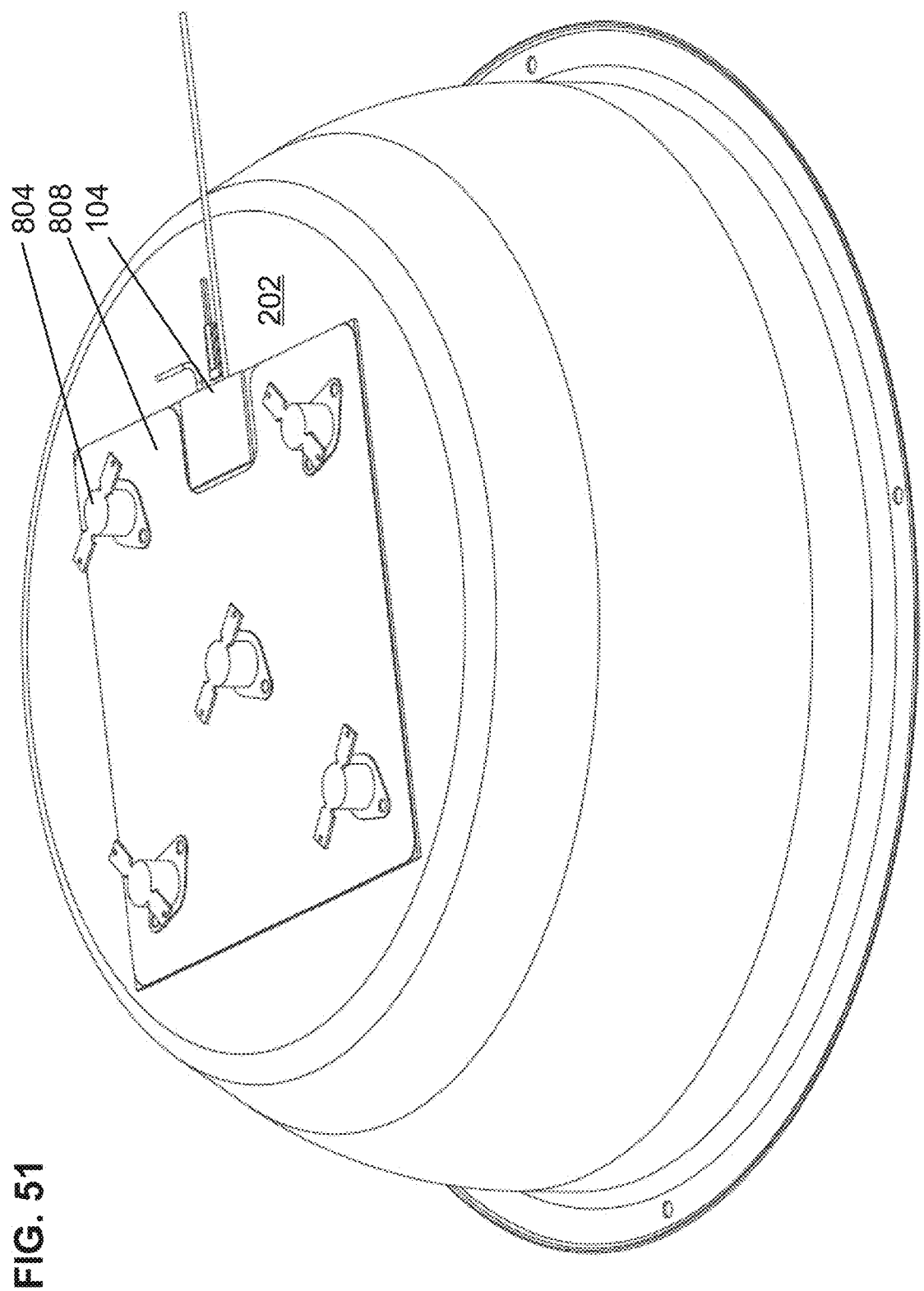
FIG. 51 is the same view as FIG. 50 of the bottom of a basin 202, but the components are shown the assembled positions.

FIG. 51 is the same view as FIG. 50 of the bottom of a basin 202, but the components are shown the assembled positions. The heating element 104 may be adhered to the basin 202. The heat dispersion plate 808 may be adhered to the heating element 104. The set of air gap detectors 804 may be adhered to the heat dispersion plate 808 so that direct thermal contact is established between the set of air gap detectors 804 through the heat dispersion plate 808 to monitor for hot spots in the heating element 104. The heat dispersion plate 808 may be made with a sheet of copper that is 0.01 inches thick as this provides excellent thermal conductivity. A thicker sheet of copper would conduct heat better, but would also add additional thermal mass which could slow heating and control responses. Thus, one of skill the art may choose a material for the heat dispersion plate 808 that is something other than 0.01-inch-thick copper sheet. Those of skill in the art can access data on thermal conductivity of materials to select a material that approaches or exceeds the thermal conductivity of commercial grade copper. Thermal conductivity of commercial grade copper has been measured to be as low as 311 watts per meter-kelvin. (See https://en.wikipedia.org/wiki/List_of_thermal_conductivities) A material with a thermal conductivity below that of copper that is a fairly good thermal conductor may be used to make the heat dispersion plate 808 if part of a design with an adequate number of air gaps detectors to provide adequate monitoring of the draped basin.

Figure 52:
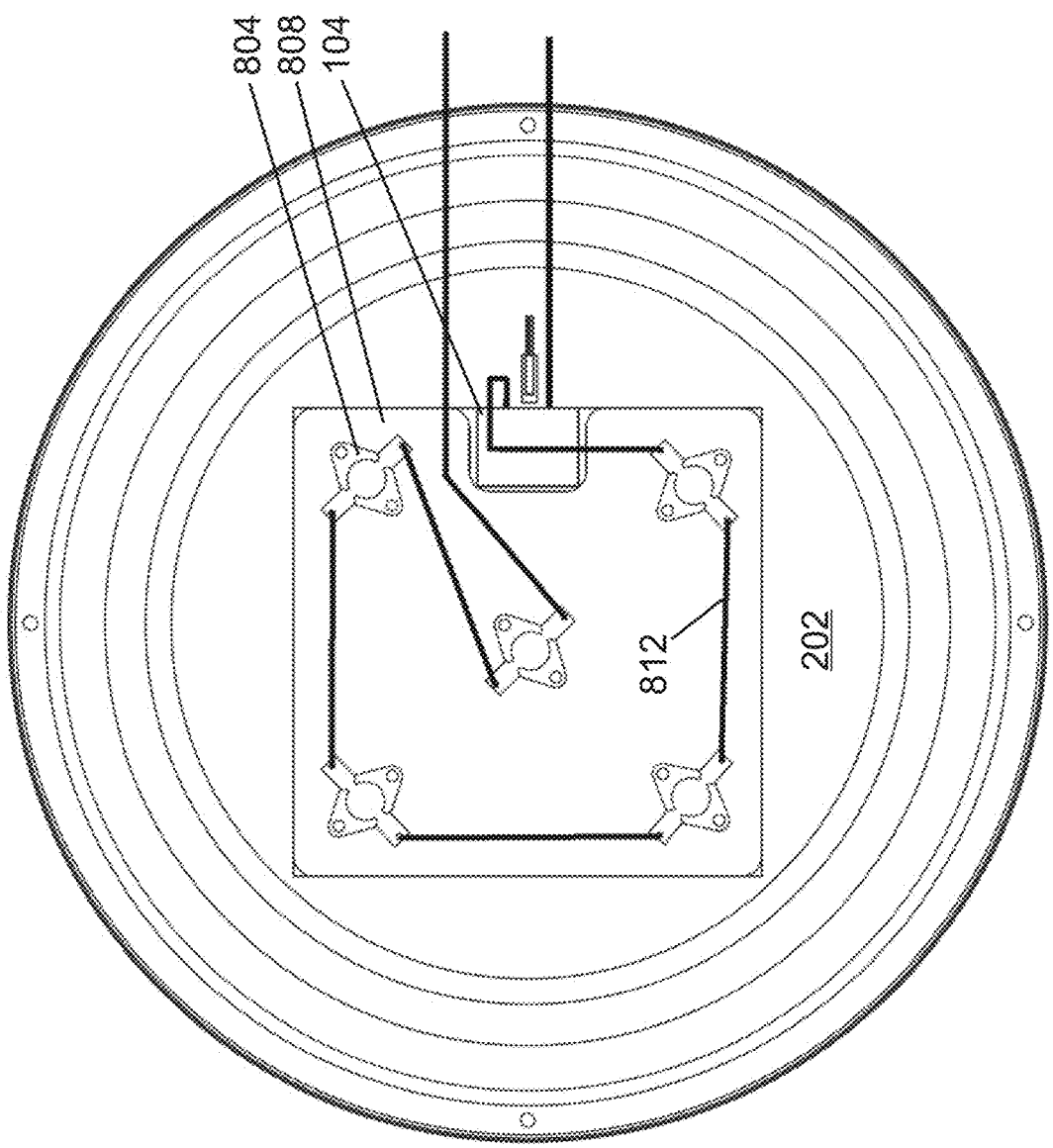
FIG. 52 shows an example of serial connections of the air gap detectors in the set of air gap detectors 804.

FIG. 52 shows an example of serial connections of the air gap detectors in the set of air gap detectors 804. Other patterns may be used. A serial wiring pattern has the benefit that if any of the air gap detectors breaks the electrical connection due to a high temperature excursion, power to the heating element 104 is interrupted FIG. 53 is a cross section of a basin 202 with a hypothetical perfectly fitting drape 300 that leaves no separation between the basin 202 and the drape 300 so that they appear as one item.

In order to discuss components, this is a gap between the heating element 104 and the bottom of the basin 202. Likewise there is a gap between the lower side of the heating element 104 and the heat dispersion plate 808. In operation there would be good thermal contact rather than these two gaps.

Figure 53:
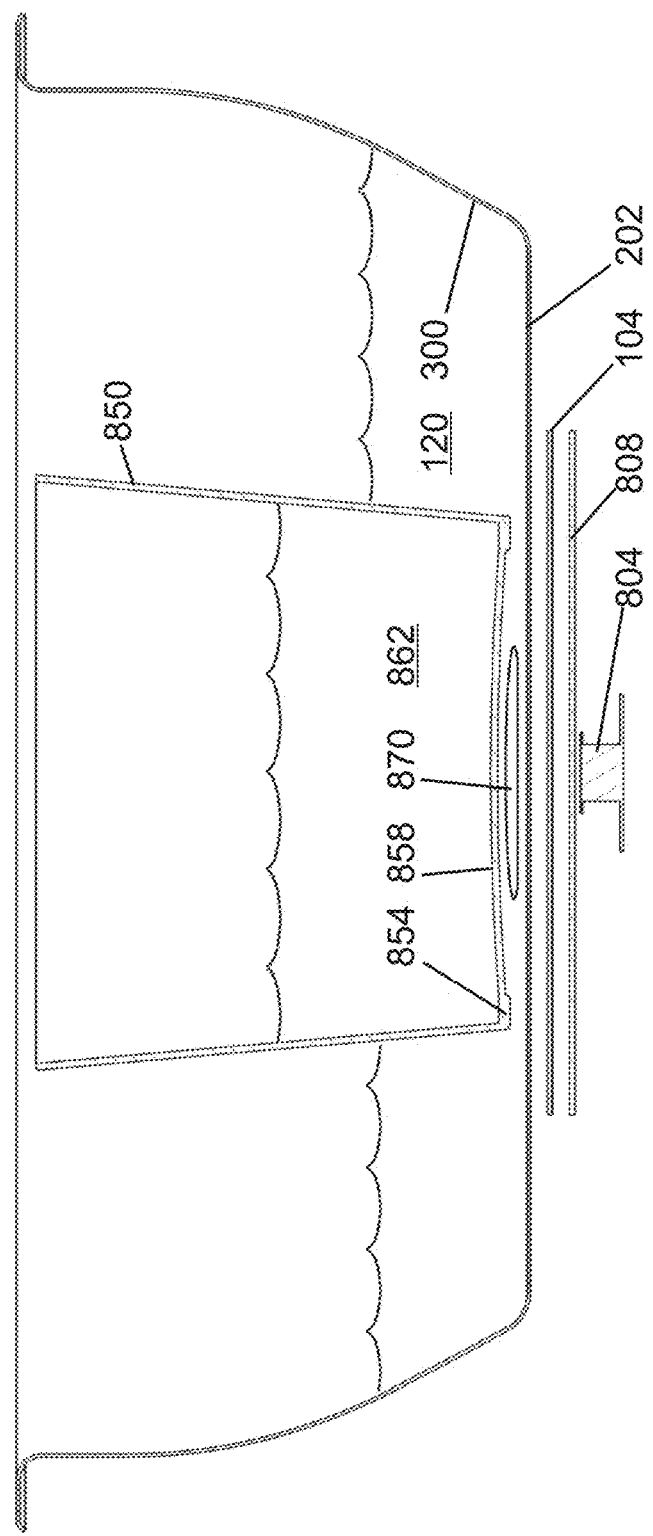
FIG. 53 is a cross section of a basin 202 with a cup 850 holding fluid 862 within the liquid 120 contained in the draped basin 202.

FIG. 53 has a cup 850 with fluid 862 above the drape 300 lining basin 202. The liquid 120 that partially fills the basin drape 300 is likely to be sterile saline or an analogous liquid. Sometimes a fluid 862 such as a medicine or other liquid to be used in a procedure is heated by placing a cup 850 with the fluid 862 into the warm liquid 120 above the drape 300.

Not all cups have flat bottoms. The outer rim 854 of the cup 850 is shown hovering above the drape 300 so that the shape of the cup 850 is easy to see but one of skill in the art recognizes that the outer rim 854 would normally be in contact with the drape 300 to substantially isolate the volume under cup 850 from the bulk of the liquid 120 in the drape 300.

The majority of the bottom of the cup 850 is a slightly curved raised surface 858 running between the sides of the outer rim 854. This raised surface 858 is apt to capture some volume of air and form a trapped bubble in an air gap 870 between the raised surface 858 and the drape 300. The air gap 870 will significantly inhibit heat transfer from the heating element 104 to the cup 850 and the fluid 862. Thus the air gap 870 that will cause a local hot spot for the heating element 104 and possibly damage the drape 300 would be an air gap 870 above the drape 300 not an air gap 128 between the drape 300 and the basin 202 as previously discussed in both FIG. 6 and in concern about wrinkles.

FIG. 53 shows the air gap 870 directly above one of air gap detectors 804 but as described above, the use of the heat dispersion plate 808 helps the set of air gap detectors 804 detect air gaps 870 or 128 a distance laterally from the closest air gap detector 804.

Figure 54:
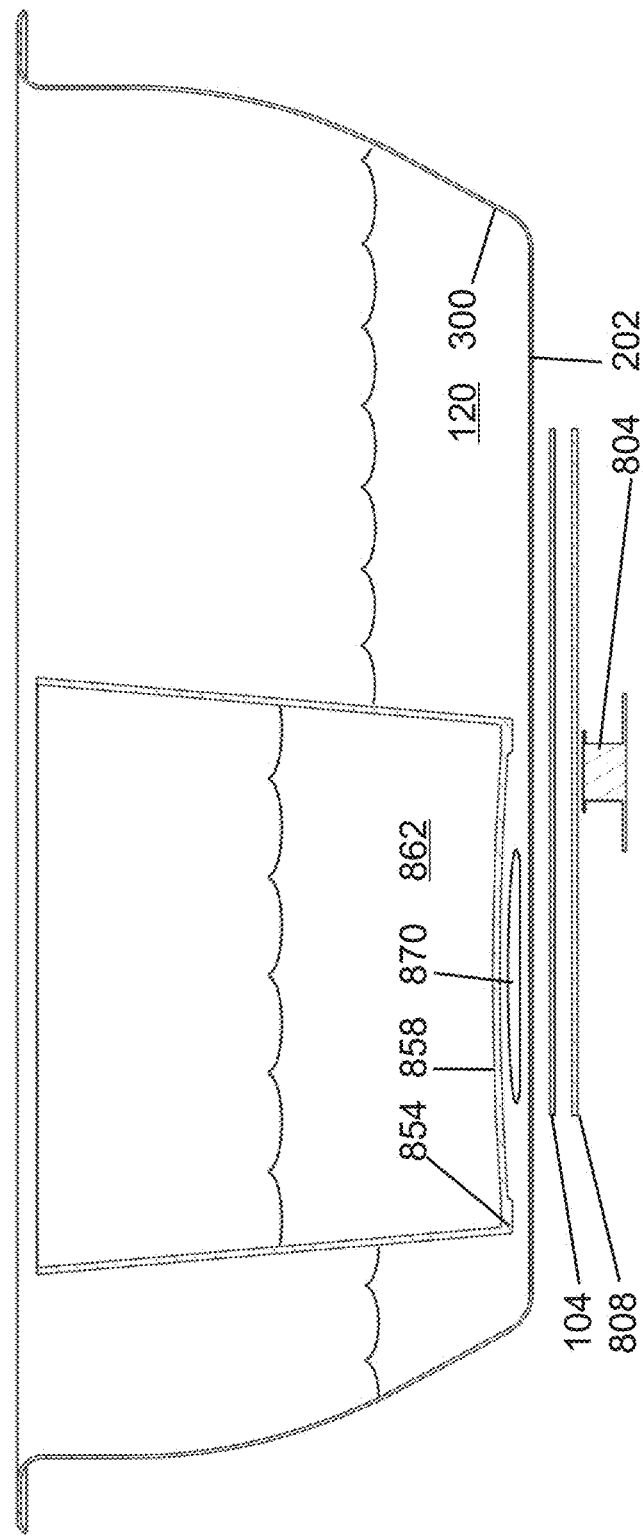
FIG. 54 is a cross section of a basin 202 with a cup 850 holding fluid 862 within the draped basin 202 with the cup 850 not directly over any of the set of air gap detectors 804.

FIG. 54 shows the cup 850 and air gap 870 offset from the closest air gap detector 804. The use of the heat dispersion plate 808 in thermal contact with the heating element 104 allows the temperature of the air gap detector 804 to be influenced by the local hot spot in the heating element 104 caused by the air gap 870.

One of skill in the art will recognize that some of the alternative implementations set forth above are not universally mutually exclusive and that in some cases additional implementations can be created that employ aspects of two or more of the variations described above. Likewise, the present disclosure is not limited to the specific examples or particular embodiments provided to promote understanding of the various teachings of the present disclosure. Moreover, the scope of the claims which follow covers the range of variations, modifications, and substitutes for the components described herein as would be known to those of skill in the art.

Where methods and/or events described above indicate certain events and/or procedures occurring in a certain order, the ordering of certain events and/or procedures may be modified. Additionally, certain events and/or procedures may be performed concurrently in a parallel process when possible, as well as performed sequentially as described above.

The legal limitations of the scope of the claimed invention are set forth in the claims that follow and extend to cover their legal equivalents. Those unfamiliar with the legal tests for equivalency should consult a person registered to practice before the patent authority which granted this patent such as the United States Patent and Trademark Office or its counterpart.

What is claimed is:

1. A heating system for providing heat to a draped basin containing liquid above a drape, the heating system comprising:
 a set of at least one at least one heating element including a first heating element in thermal contact with an underside of the draped basin;
 at least one temperature sensor monitored by a controller that regulates a first flow of electricity sent to the first heating element for use in providing heat;
 a first set of at least one air gap detector including a first air gap detector located in thermal contact with the first heating element:

the first air gap detector monitoring temperature on a portion of the underside of the draped basin in proximity to the first air gap detector;

the first air gap detector responding to a temperature above a first high setpoint temperature by interrupting the first flow of electricity sent to the first heating element;

the first air gap detector continuing the interruption of the first flow of electricity sent to the first heating element until detecting that the temperature is below a first reset setpoint temperature which is less than the first high setpoint temperature; and wherein an air gap in proximity to the first air gap detector is prevented from causing a severe temperature excursion in a portion of the draped basin by the interruption of the first flow of electricity sent to the first heating element.

2. The heating system for applying heat to the draped basin containing liquid above the drape of claim 1, wherein the air gap is between the draped basin and the drape.

3. The heating system for applying heat to the draped basin containing liquid above the drape of claim 1, wherein the air gap is above both the draped basin and the drape.

4. The heating system for applying heat to the draped basin containing liquid above the drape of claim 1, wherein the air gap is not directly above the first air gap detector but is sufficiently proximal to the first air gap detector to allow the first air gap detector to respond to the temperature above the first high setpoint temperature by interrupting the first flow of electricity sent to the first heating element.

5. The heating system for applying heat to the draped basin containing liquid above the drape of claim 1, the first air gap detector in thermal contact with the first heating element is in indirect thermal contact with the first heating element as a heat dispersion plate is located between the first heating element and the first air gap detector to enhance an ability of the first air gap detector to react to an air gap that is not directly above the first air gap detector by conducting thermal energy through the heat dispersion plate.

6. The heating system for applying heat to the draped basin containing liquid above the drape of claim 5, wherein the heat dispersion plate comprises copper.

7. The heating system for applying heat to the draped basin containing liquid above the drape of claim 5, wherein the heat dispersion plate has a thermal conductivity of at least 311 watts per meter-kelvin.

8. The heating system for applying heat to the draped basin containing liquid above the drape of claim 5, wherein the heat dispersion plate is adhered to the first heating element and the first air gap detector is adhered to the heat dispersion plate.

9. The heating system for applying heat to the draped basin containing liquid above the drape of claim 5, wherein the heating system further comprises:

a second heating element with a second set of air gap detectors including an additional air gap detector and the additional air gap detector is adapted to interrupt a second flow of electricity sent to the second heating element for use in creating heat while the first heating element with the first air gap detector continues to receive the first flow of electricity send to the first heating element.

10. The heating system for applying heat to the draped basin containing liquid above the drape of claim 1, wherein the heating system further comprises:

a second air gap detector on the first heating element located away from the first air gap detector;

the second air gap detector monitoring a second portion of the underside of the draped basin in proximity to the second air gap detector;

the second air gap detector responding to a temperature above a second high setpoint temperature by interrupting the first flow of electricity sent to the first heating element;

the second air gap detector continuing the interruption of the first flow of electricity sent to the first heating element until detecting that the temperature is below a second reset setpoint temperature which is less than the second high setpoint temperature; and wherein the first flow of electricity sent to the first heating element may be interrupted by the first air gap detector or by the second air gap detector.

11. The heating system for applying heat to the draped basin containing liquid above the drape of claim 10, wherein the first high setpoint temperature is different from the second high setpoint temperature.

12. The heating system for applying heat to the draped basin containing liquid above the drape of claim 10, wherein the first reset setpoint temperature is different from the second reset setpoint temperature.

13. A method for preventing a temperature excursion on a portion of a draped basin containing a liquid above a drape covering the draped basin, the method comprising:

obtaining a heating system for providing heat to the draped basin containing liquid above the drape in accordance with claim 1;

adding the liquid to the draped basin;

using an output from a temperature sensor to determine an amount of electricity provided to a heating element in thermal connection with at least a portion of an underside of the draped basin; and causing an interruption of electricity provided to the heating element when a temperature sensed at an air gap detector within a set of at least two air gap detectors exceeds a high temperature setpoint for that air gap detector.

14. The method for preventing the temperature excursion on the portion of the draped basin containing the liquid above the drape covering the draped basin of claim 13, wherein the air gap detector is responding to an air gap is between the draped basin and the drape.

15. The method for preventing the temperature excursion on the portion of the draped basin containing the liquid above the drape covering the draped basin of claim 13, wherein the air gap detector is responding to an air gap above both the draped basin and the drape.

16. The method for preventing the temperature excursion on the portion of the draped basin containing the liquid above the drape covering the draped basin of claim 13, wherein then air gap is not directly above the first air gap detector but is sufficiently proximal to the first air gap detector to allow the first air gap detector to respond to the temperature above the high temperature setpoint by interrupting the amount of electricity sent to the heating element.

17. The method for preventing the temperature excursion on the portion of the draped basin containing the liquid above the drape covering the draped basin of claim 13, wherein the interruption of electricity provided to the heating element continues until a new temperature sensed at the air gap detector falls below a reset temperature setpoint for that air gap detector which is below the high temperature setpoint for that air gap detector.

18. The method for preventing the temperature excursion on the portion of the draped basin containing the liquid above the drape covering the draped basin of claim 13, wherein a single heating element has at least two air gap detectors and any of the at least two air gap detectors can interrupt electricity provided to the single heating element when the temperature sensed at any of the at least two air gap detectors exceeds the high temperature setpoint for that air gap detector.

19. The method for preventing the temperature excursion on the portion of the draped basin containing the liquid above the drape covering the draped basin of claim 18, wherein the single heating element has at least two air gap detectors and each of the at least two air gap detectors have a same high temperature set point.

20. The method for preventing the temperature excursion on the portion of the draped basin containing the liquid above the drape covering the draped basin of claim 18, wherein the single heating element has at least two air gap detectors and a first air gap detector within the set of at least two air gap detectors has a different high temperature set point than a second air gap detector within the set of at least two air gap detectors.

21. A heating system for providing heat to a draped basin containing liquid above a drape, the heating system comprising:
   a set of at least one at least one heating element including a first heating element in thermal contact with an underside of the draped basin;
   at least one temperature sensor monitored by a controller that regulates a first flow of electricity sent to the first heating element for use in providing heat;
   a first set of at least one air gap detector including a first air gap detector located in thermal contact with the first heating element:
   the first set of at least one air gap detector located near a perimeter of the basin bottom;
   the first air gap detector monitoring temperature on a portion of the underside of the draped basin in proximity to the first air gap detector;
   the first air gap detector responding to a temperature above a first high setpoint temperature by interrupting the first flow of electricity sent to the first heating element;
   the first air gap detector continuing the interruption of the first flow of electricity sent to the first heating element until detecting that the temperature is below a first reset setpoint temperature which is less than the first high setpoint temperature; and
   wherein an air gap between the draped basin and the drape that is in proximity to the first air gap detector is prevented from causing a severe temperature excursion in a portion of the draped basin by the interruption of the first flow of electricity sent to the first heating element.

22. The heating system for applying heat to the draped basin containing liquid above the drape of claim 21 further comprising:
   a second set of at least one air gap detector including a specific air gap detector located in thermal contact with the first heating element:
   the second set of at least one air gap detector located in an interior portion of the draped basin away from the perimeter of the basin bottom;
   the specific air gap detector monitoring temperature on the portion of the underside of the draped basin in proximity to the specific air gap detector;
   the specific air gap detector responding to a temperature above a specific high setpoint temperature by interrupting the first flow of electricity sent to the first heating element;
   the specific air gap detector continuing the interruption of the first flow of electricity sent to the first heating element until detecting that the temperature is below a specific reset setpoint temperature which is less than the specific high setpoint temperature; and
   wherein an interior air gap between the draped basin and the drape that is in proximity to the specific air gap detector is prevented from causing a severe temperature excursion in the interior portion of the draped basin by the interruption of the first flow of electricity sent to the first heating element.

23. The heating system for providing heat to a draped basin of claim 22, wherein an air bubble trapped by an object placed above the draped basin causes the specific air gap detector responding to a temperature above the specific high setpoint temperature by interrupting the first flow of electricity sent to the first heating element to interrupt the first flow of electricity for the air bubble trapped by the object placed above the draped basin.

* * * * *

UNITED STATES PATENT AND TRADEMARK OFFICE
CERTIFICATE OF CORRECTION

PATENT NO. : 12,290,332 B2
APPLICATION NO. : 17/229813
DATED : May 6, 2025
INVENTOR(S) : Rackers et al.

Page 1 of 1

It is certified that error appears in the above-identified patent and that said Letters Patent is hereby corrected as shown below:

In the Claims

| | |
|---|---|
| Column 24, Line 59, Claim 1 | 'at least one at least one' should read -at least one-; |
| Column 25, Line 63, Claim 9 | 'send' should read -sent-; and |
| Column 27, Line 27, Claim 21 | 'at least one at least one' should read -at least one-. |

Signed and Sealed this
Tenth Day of June, 2025

Coke Morgan Stewart
*Acting Director of the United States Patent and Trademark Office*